US008716280B2

(12) United States Patent
Gaucher et al.

(10) Patent No.: US 8,716,280 B2
(45) Date of Patent: May 6, 2014

(54) BICYCLIC ANTIBIOTICS

(75) Inventors: Berangere Gaucher, Mulhouse (FR); Franck Hubert Danel, Bruebach (FR); Patrick Roussel, Mulhouse (FR)

(73) Assignee: Basilea Pharmaceutica AG, Basel (CH)

( * ) Notice: Subject to any disclaimer, the term of this patent is extended or adjusted under 35 U.S.C. 154(b) by 201 days.

(21) Appl. No.: 13/145,323

(22) PCT Filed: Jan. 21, 2010

(86) PCT No.: PCT/EP2010/050684
§ 371 (c)(1),
(2), (4) Date: Aug. 4, 2011

(87) PCT Pub. No.: WO2010/084152
PCT Pub. Date: Jul. 29, 2010

(65) Prior Publication Data
US 2012/0040957 A1    Feb. 16, 2012

(30) Foreign Application Priority Data
Jan. 21, 2009  (EP) .................................... 09151027

(51) Int. Cl.
C07D 498/04    (2006.01)
C07D 413/04    (2006.01)
A61K 31/5415   (2006.01)
A61K 31/5383   (2006.01)

(52) U.S. Cl.
USPC ............................. 514/224.2; 544/51; 544/52

(58) Field of Classification Search
USPC .................................... 544/51, 52; 514/224.2
See application file for complete search history.

(56) References Cited

U.S. PATENT DOCUMENTS

| | | | |
|---|---|---|---|
| 5,442,065 A | 8/1995 | Magnus et al. | |
| 6,602,884 B2 | 8/2003 | Bacque et al. | |
| 7,223,776 B2 | 5/2007 | Surivet et al. | |

FOREIGN PATENT DOCUMENTS

| | | |
|---|---|---|
| EP | 0293071 | 11/1988 |
| WO | 9500511 | 1/1995 |
| WO | 0234754 | 5/2002 |
| WO | 2004002992 | 1/2004 |
| WO | 2004014871 | 2/2004 |
| WO | 2004058144 | 7/2004 |
| WO | 2006002047 | 1/2006 |
| WO | 2006004949 | 1/2006 |
| WO | 2006014580 | 2/2006 |
| WO | 2006021448 | 3/2006 |
| WO | 2006032466 | 3/2006 |
| WO | 2006038734 | 4/2006 |
| WO | 2006099884 | 9/2006 |
| WO | 2006105289 | 10/2006 |
| WO | 2007052843 | 5/2007 |
| WO | 2007086016 | 8/2007 |
| WO | 2007093507 | 8/2007 |

OTHER PUBLICATIONS

The International Search Report and Written Opinion by the International Searching Authority, issued on Feb. 18, 2010, in the PCT application No. PCT/EP2010/050684.
Mitsunobu, "The Use of Diethyl Azodicarboxylate and Triphenylphosphine in Synthesis and Transformation of Natural Products," Synthesis 1981, 1-28. (Review).
Hutchins et al., Comprehensive Organic Synthesis, B.M. Trost, I. Fleming, Eds; Pergamon Press: New York (1991), vol. 8, p. 25-78.
Singh et al., Regioselective Activation of Aminothlazole (iminoxyacetic acid)acetic Acid: an Efficient Synthesis of the Monobactam Aztreonam, Org. Process Res. & Dev., 2002, 863-868.
Ishikawa et al., Journal of Antibiotics, "Studies on anti-MRSA parenteral cephalosporins. II. Synthesis and antibacterial activity of 7:beta-12-(5-amino-1,2,4-thiadiazol-3-yl)          -2(Z)-a[koxyiminoacetamido]-3-(substituted          imidazo[1,2-b] pyridazinium-1-yl)methyl-3-cephem-4-carboxylates and related compounds", 2000, vol. 53, No. 10, pp. 1071-1085.
Hazeldine et al., "Design, Synthesis, and Biological Evaluation of Analogues of the Antitumor Agent, 2-{4-[(7-Chloro-2-quinoxalinyl)oxy]phenoxy}propionic Acid (XK469)," J. Med. Chem., 2001, 44, 1758-1776.
Curd et al., "275. Synthetic antimalarials. Part XL. The effect of variation of substituents in 2-chloro-3-β-diethylaminoethylaminoquinoxaline," J. Chem. Soc., 1949, 1271.
Protective Groups in Organic Synthesis, 3rd Edition, by T.W. Greene and P.G.M. Wuts, published by John Wiley & Sons, 1999, cited on p. 17 of the present application. (only pp. 495-615 are enclosed.).
Hazeldine et al., "II. Synthesis and Biological Evaluation of Some Bioisosteres and Congeners of the Antitumor Agent, 2-{4-[(7-Chloro-2-quinoxalinyl) oxy] phenoxy}propionic Acid (XK469)," J. Med. Chem., 2002, 45, 3130.

*Primary Examiner* — Kahsay Habte

(57) ABSTRACT

The antibacterial compound of formula I wherein
X1, X3; X4 and X6, each independently of the others, represents a nitrogen atom or CR2, with the proviso that at least one of X1, X3; X4 and X6 represents a nitrogen atom;
X2 represents C—H, C—(C1-C6alkyl), C—(C1-C6alkoxy), C-halogen, C—COOH;
X5 represents C—H or C—(C1-C6alkyl), C-halogen; A1, A2, A3, R1 and R4 represent various substituents, G represents aryl or heteroaryl, which is unsubstituted or substituted which compounds show good activity against pathogenic bacteria.

29 Claims, No Drawings

BICYCLIC ANTIBIOTICS

The present invention relates to antibacterial compounds of a formula:

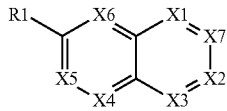

wherein X1, X2, X3; X4, X5, X6, and X7, each independently of the others, represent nitrogen or CR2 wherein at least one of all groups X1, X2, X3; X4, X5, X6, and X7 but not more than two of either X4, X5 and X6 or X1, X2, X3 and X7 represent nitrogen and wherein R1 and R2 are selected from hydrogen and certain substituents which substituents also include more complex molecular side chains.

Many of such antibacterial compounds are already known in the art. These known compounds have in common that X1 represents CR2 wherein R2 represents such a molecular side chain like e.g. corresponding quinolines, quinoxalines or naphthyridines, which are known from WO2002/072572, WO2004/035569, WO2006/002047, WO2006/014580, WO2006/021448, WO2006/032466, and WO2007/086016.

By way of example, WO2006/021448 discloses antibacterial compounds with the general structure

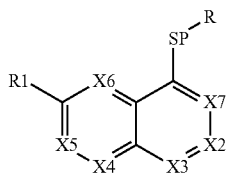

wherein
X2, X3, X4, X5, X6 and X7 independently represent N or CR2,
wherein R2 represents hydrogen or a substituent;
SP represents linear two-atomic spacer group like in particular —NHCO—; —CH$_2$CO—; —COCH$_2$—, —CH$_2$SO$_2$—; —NHSO$_2$—; —CH$_2$CH(OH)—; —CH$_2$CH$_2$—; —CH(OH)CH$_2$—; —CONH—; —CH$_2$N(C$_1$-C$_4$alkyl)-; —CH$_2$O— or —CH$_2$S— and
R represents a group selected from C6-C8cycloalkylene groups; saturated and unsaturated 4 to 8-membered heterocyclodiyl with 1, 2 or 3 heteroatoms selected from nitrogen and oxygen, which group is unsubstituted or substituted.

The numerous exemplified compounds are said to exhibit a MIC (µg/ml) against at least one of the following microorganisms: *Acinetobacter baumannii; Enterobacter cloacae; Escherichia coli; Klebsiella pneumoniae; Proteus mirabilis; Pseudomonas aeruginosa; Stenotrophomonas maltophilia; Staphylococcus aureus; Enterococcus faecalis; Staphylococcus epidermidis; Streptococcus pneumoniae* and *Enterococcus faecium* of less or equal to 8 µg/ml.

In view of the increasing resistance development of pathogenic bacteria against known antibacterial agents, including multiple resistances, there is an ongoing need to find novel antibacterial substances, in particular compounds having a different chemical structure.

The present invention relates to such antibacterial compounds of novel chemical structure. In particular, it relates to compounds of formula (I)

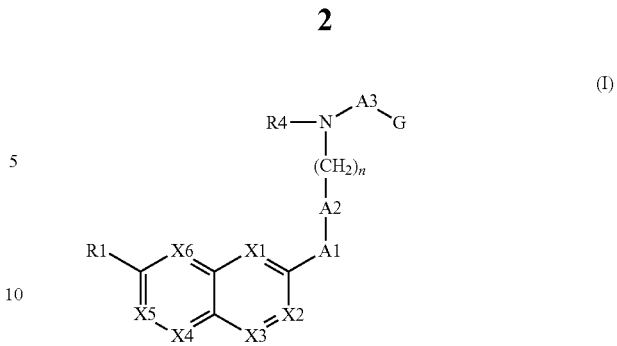

wherein
X1, X3; X4 and X6, each independently of the others, represents a nitrogen atom or CR2, with the proviso that at least one of X1, X3; X4 and X6 represents a nitrogen atom;
X2 represents C—H, C—(C1-C6alkyl), C—(C1-C6alkoxy), C-halogen, C—COOH;
X5 represents C—H or C—(C1-C6alkyl), C-halogen;
R1 and R2, independently of one another, represent hydrogen or a substituent selected from hydroxy, halogen, carboxy, amino, C1-C6alkylamino, di(C1-C6alkyl)amino, mercapto (SH), cyano, nitro, C1-C6alkyl, C1-C6alkoxy, C1-C6alkylthio, C1-C6alkylaminocarbonyloxy, C2-C6alkenyl, C2-C6alkynyl, C1-C6alkylcarbonyloxy, C1-C6 alkylsulfonyloxy, C1-C6heteroalkylcarbonyloxy, C5-C6heterocyclylcarbonyloxy, C1-C6heteroalkyl, C1-C6heteroalkoxy, wherein heteroalkyl, heteroalkoxy groups or heterocyclyl comprise 1, 2 or 3 heteroatoms selected from nitrogen, oxygen and sulphur, in which substituents the alkyl moieties are unsubstituted or further substituted by halogeno, cyano, hydroxy, C1-C4alkoxy, C1-C4alkylcarbonyl, C1-C4alkoxycarbonyl, unsubstituted or substituted phenoxy or phenylcarbonyl, unsubstituted or substituted C5-C6heterocyclyl or carboxy;

A1 represents a divalent group of one of the formulae
—O—(CH$_2$)$_m$—(CH$_2$)—, —S—(CH$_2$)$_m$—(CH$_2$)— or —(C=O)O—(CH$_2$)$_m$—(CH$_2$)—, wherein the (CH$_2$)$_m$ moiety is optionally substituted by C1-C4alkyl, C2-C4alkenyl, C3-C6cycloalkyl, C3-C6cycloalkylmethyl, morpholinomethyl, halogen, carboxy, hydroxy, C1-C4alkoxy;
C1-C4alkoxyC1-C4alkyl, C1-C4alkoxy(C1-C4alkylenoxy)C1-C4alkyl, benzyloxyC1-C4alkyl, amino, mono- or di-(C1-C4alkyl)amino or acylamino, in which substituents the alkyl moieties can be further substituted by 1 or more fluoro atoms
m is 0, 1 or 2, provided that the number of atoms in the direct chain between the two terminal valencies of A1 is at least 3,
which group A1 is linked to A2 via the terminal (CH$_2$)-moiety;
A2 is a group selected from C3-C8cycloalkylene; saturated and unsaturated 4 to 8-membered heterocyclodiyl with 1, 2 or 3 heteroatoms selected from nitrogen, oxygen and sulphur, which group A2 is unsubstituted or substituted;
R4 represents hydrogen or C1-C4alkyl;
A3 represents C1-C4alkylene, C2-C4alkenylene, >C=O, —C(O)C1-C3alkylene-, —C(=O)NH—, or a group selected from —C$_2$H$_4$NH—, —C$_2$H$_4$O—, and —C$_2$H$_4$S— being linked to the adjacent NR4-group via the carbon atom; and
G represents aryl or heteroaryl, which is unsubstituted or substituted and
n is 0, 1 or 2;
or a pharmaceutically acceptable salt, a hydrate or solvate thereof.

The compounds of the invention show good activity against pathogenic bacteria, in particular against at least one of the following Gram-positive pathogenic bacteria like *staphylococci, streptococci* and Gram-negative bacteria such as for example *Escherichia coli*, as shown in the Examples. Furthermore they are active against enterococci, and *Haemophilus influenzae*.

The antibacterial activity found is particularly surprising because it has been found that the compounds of WO2006/021448 loose their antibacterial activity when the side chain is shifted from the position disclosed in WO2006/021448 to that of the present invention as shown in the following table.

Comparison of the C4 and C3 position of the methoxyquinoline using the same side chain (especially one) triple bond(s). Groups having one double and one triple bond are also covered like e.g. pent-3-en-1-yne. The alkenyl and alkynyl groups may also be further substituted by carboxy, amino, mono- or di(C1-C4alkyl)amino, halogeno, e.g. by fluorine, chlorine, bromine or iodine, cyano, hydroxy, mercapto, C1-C4alkoxy, C1-C4alkylcarbonyl, C1-C4alkoxycarbonyl, unsubstituted or substituted phenoxy or phenylcarbonyl, unsubstituted or substituted C5-C6heterocyclyl or by =O, =S, =NH or NO₂ groups and the like, in which alkyl substituents the C1-C4alkyl or C1-C4alkoxy groups are unsubstituted.

The expression "C3-C6heteroalkyl" preferably refers to an alkyl, alkenyl or alkynyl group (for example heteroalkenyl, heteroalkynyl) in which one or more (preferably 1, 2 or 3)

| | MIC (mg/L) | | | |
|---|---|---|---|---|
| | C4 position according to WO2006/021448 | | C3 position according to present invention | |
| | 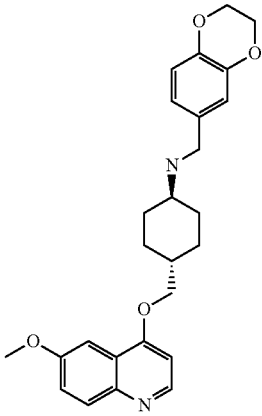 [SMILES: COc1ccc2nccc(OC[C@H]3CC[C@H](NCc4ccc5c(c4)OCCO5)CC3)c2c1] | 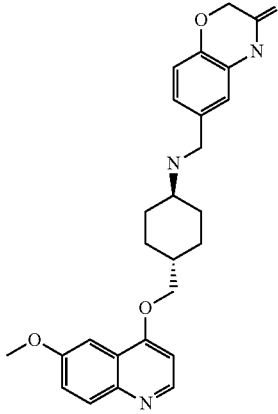 | 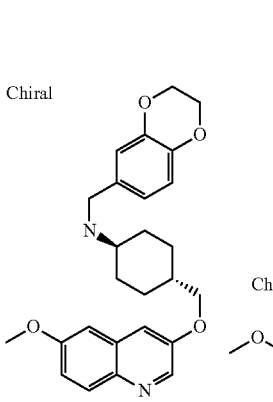 | 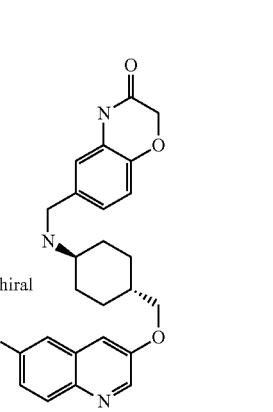 |
| *S. aureus* ATCC29213 | 0.5 | 1 | >32 | >32 |
| *S. pneumoniae* ATCC49619 | 0.5 | 2 | 32 | 32 |
| *E. coli* UB1005 | 16 | 1 | >32 | >32 |

The expression "C1-C6alkyl" preferably refers to saturated, straight-chain or branched hydrocarbon groups having from 1 to 6 carbon atoms like, for example methyl, ethyl, propyl, iso-propyl, n-butyl, iso-butyl, tert-butyl, n-pentyl, n-hexyl or 2,2-dimethylbutyl. C1-C4 alkyl is generally preferred. In composed expressions, like e.g. C1-C6alkoxy, C1-C6alkylamino or di(C1-C6alkyl)amino, aralkyl or heteroaralkyl or the like"C1-C6alkyl" is understood in the same way. Alkyl groups may also be further substituted by carboxy, amino, mono- or di(C1-C4alkyl)amino, halogeno, e.g. by fluorine, chlorine, bromine or iodine, cyano, hydroxy, mercapto, C1-C4alkoxy, C1-C4alkylcarbonyl, C1-C4alkoxycarbonyl, unsubstituted or substituted phenoxy or phenylcarbonyl, unsubstituted or substituted C5-C6heterocyclyl or by =O, =S, =NH or NO₂ groups and the like, in which alkyl substituents the C1-C4alkyl or C1-C4alkoxy groups are unsubstituted.

The expressions "C2-C6alkenyl" and "C2-C6alkynyl" preferably refer to at least partially unsaturated, straight-chain or branched hydrocarbon groups that contain from 2 to 6 carbon atoms, preferably from 2 to 4 carbon atoms like, for example, ethenyl, allyl, propargyl, isoprenyl or hex-2-enyl group. Preferably, alkenyl groups have one or two (especially one) double bond(s) and alkynyl groups have one or two carbon atoms have been replaced each independently of the others by an oxygen, nitrogen, silicon or sulphur atom, preferably an oxygen, sulphur or nitrogen atom. Specific examples of heteroalkyl groups are methoxymethyl, ethoxymethyl, methoxyethyl, methylaminomethyl, ethylaminomethyl, diisopropyl-aminoethyl, enol ether, dimethylaminomethyl, dimethylaminoethyl. The alkyl part(s) of "C3-C6heteroalkyl" can be further substituted as defined for C1-C6alkyl.

The expression "C3-C8cycloalkylene" preferably refers to a bivalent saturated or partially unsaturated (for example a cyclic group having one, two or more double bonds, such as a cycloalkenylene group), cyclic group containing from 3 to 8 carbon atoms, especially 3, 4, 5, 6 or 7, preferably 5 or 6 ring carbon atoms. For the purposes of the present invention the expression cycloalkylene refers furthermore to groups in which one or more hydrogen atoms have been replaced each independently of the others by carboxy, amino, mono- or di(C1-C4alkyl)amino, halogeno, e.g. by fluorine, chlorine, bromine or iodine, cyano, hydroxy, mercapto, C1-C4alkoxy, C1-C4alkylcarbonyl, C1-C4alkoxycarbonyl, unsubstituted or substituted phenoxy or phenylcarbonyl, unsubstituted or substituted C5-C6heterocyclyl or by =O, =S, =NH or NO₂ groups and the like, in which alkyl substituents the C1-C4alkyl or C1-C4alkoxy groups are unsubstituted, thus, for example, to bivalent residues of cyclic ketones such as, for example, cyclohexanone, 2-cyclohexenone or cyclopentanone. Further specific examples of cycloalkylene groups are cyclobutylene, cyclopentylene, cyclohexylene, cyclopentenylene and cyclohexadienylene.

The expression "heterocyclodiyl" as used herein preferably refers to a saturated or unsaturated bivalent 4 to 8-membered cyclic group as defined above in connection with the definition of cycloalkylene (including divalent heteroaromatic groups), in which one or more (preferably 1, 2 or 3) ring carbon atoms have been replaced each independently of the other by an oxygen, nitrogen, silicon, or sulphur atom, preferably by an oxygen, sulphur or most preferably nitrogen atom. The expression heterocyclodiyl refers furthermore to groups in which one or more hydrogen atoms have been replaced each independently of the others by carboxy, amino, mono- or di(C1-C4alkyl)amino, halogeno, e.g. by fluorine, chlorine, bromine or iodine, cyano, hydroxy, mercapto, C1-C4alkoxy, C1-C4alkylcarbonyl, C1-C4alkoxycarbonyl, unsubstituted or substituted phenoxy or phenylcarbonyl, unsubstituted or substituted C5-C6heterocyclyl or by =O, =S, =NH or $NO_2$ groups and the like, in which alkyl substituents the C1-C4alkyl or C1-C4alkoxy groups are unsubstituted. Preferred substituents of heterocyclodiyl groups, in particular of A2 in the meaning "heterocyclodiyl" are hydroxy, C1-C4alkyl and carboxy. Suitable examples of heterocyclodiyl groups include piperidin-diyl, piperazin-diyl, morpholin-diyl, pyrrolidin-diyl, tetrahydro-thiophenyl-diyl, tetrahydropyran-diyl, tetrahydrofuran-diyl or 2-pyrazolin-diyl. Particularly preferred are saturated or unsaturated 4 to 6-membered heterocyclodiyl groups with one or two nitrogen atoms as the heteroatom(s), in particular saturated 4 to 6-membered heterocyclodiyl with one nitrogen atom as the heteroatom.

The expression "aryl" as used herein preferably refers to an aromatic group that contains one or more rings and from 6 to 14 ring carbon atoms, preferably from 6 to 10 (especially 6) ring carbon atoms. The expression aryl preferably refers furthermore to such groups in which one or more hydrogen atoms have been replaced each independently of the others by alkyl, fluorine, chlorine, bromine or iodine atoms or by carboxy, alkoxy, mono- or di(C1-C4alkyl)amino, OH, $NH_2$, cyano or $NO_2$ groups. Examples are phenyl, 4-methyl-phenyl, 4-tert-butyl-phenyl; 3-fluoro-4-methyl-phenyl, 3-fluoro-4-(trifluoromethyl)-phenyl; naphthyl, biphenyl, 2-fluorophenyl, anilinyl, 3-nitro-phenyl or 4-hydroxyphenyl.

The expression "heteroaryl" as used herein preferably refers to an aromatic group that contains one or more rings and from 5 to 14 ring atoms, preferably from 5 to 10 (especially 5, 6, 8, 9 or 10) ring atoms, and contains one or more (preferably 1, 2, 3 or 4) oxygen, nitrogen or sulphur ring atoms, preferably oxygen, sulfur or nitrogen atoms. The expression heteroaryl preferably refers furthermore to groups in which one or more hydrogen atoms have been replaced each independently of the others by fluorine, chlorine, bromine or iodine atoms or by carboxy, alkyl, alkoxy, mono- or di(C1-C4alkyl)amino, OH, mercapto, $NH_2$, cyano, $NO_2$ or unsubstituted heteroaryl groups. Examples are pyridyl, imidazolyl, thiophenyl, thieno[3,2-b]thiophenyl, benzo[b]thiophenyl, furanyl, benzofuranyl, imidazolyl, benzimidazolyl, pyrrolyl, indolyl, oxazolyl, isoxazolyl, indazolyl, indolyl, pyridazinyl, quinolinyl, purinyl, carbazolyl, acridinyl, pyrimidyl, pyrazolyl and isoquinolinyl groups.

Further rings can be fused to the aryl and heteroaryl groups as defined above, in particular further cycloalkane and/or in particular heterocycloalkane groups.

For the purposes of this invention the term "cycloalkane" preferably refers to a saturated or partially unsaturated cyclic group which contains one or more, e.g. one or two rings and from 3 to 14 ring carbon atoms, preferably from 3 to 10, most preferably 5 or 6 ring carbon atoms. The term cycloalkane preferably refers furthermore to such groups in which one or more hydrogen atoms have been replaced each independently of the others by fluorine, chlorine, bromine or iodine atoms or by carboxy, alkyl, alkoxy, mono- or di(C1-C4alkyl)amino or by OH, =O, SH, =S, $NH_2$, =NH, cyano or $NO_2$ groups, thus, for example, cyclic ketones such as, for example, cyclohexanone or cyclopentanone. Further specific examples of cycloalkane groups are a cyclopropane, cyclobutane, cyclopentane, cyclohexane, cyclopentene, cyclohexadiene.

The expression "heterocycloalkane" as used herein preferably refers to cycloalkane groups as defined above in which one or more, preferably 1, 2 or 3 ring carbon atoms have been replaced each independently of the others by an oxygen, nitrogen, silicon or sulphur atom, preferably an oxygen, sulphur or nitrogen atom. A heterocycloalkane group has preferably 1 or 2 ring(s) containing from 3 to 10, most preferably 5 or 6 ring atoms. The expression heterocycloalkane preferably refers furthermore to groups in which one or more hydrogen atoms have been replaced each independently of the others by fluorine, chlorine, bromine or iodine atoms or by carboxy, alkyl alkoxy, mono- or di(C1-C4alkyl)amino or by OH, =O, SH, =S, $NH_2$, =NH, cyano or $NO_2$ groups. Examples are a piperidine, piperazine, morpholine, pyrrolidine, thiomorpholine, tetrahydrothiophene, [1,4]dioxane, tetrahydropyrane, tetrahydrofurane or pyrazoline and also lactams, lactones, cyclic imides and cyclic anhydrides, like e.g., morpholin-3-one or thiomorpholin-3-one.

The expression halogen refers to fluorine, chlorine bromine and iodine.

Certain compounds of formula (I) may contain one, two or more centres of chirality. The present invention therefore includes both all pure enantiomers and all pure diastereoisomers and also mixtures thereof in any mixing ratio. The present invention moreover also includes all cis/trans-isomers of the compounds of the general formula (I) and mixtures thereof. The present invention moreover includes all tautomeric forms of the compounds of formula (I).

Preferred are compounds of formula (I) wherein either X3 alone represents a nitrogen atom (corresponding quinoline derivatives) or X3 and X1 represent a nitrogen atom (corresponding quinoxaline derivatives) or X3 and X6 represent a nitrogen atom (corresponding [1,5]-naphthyridine derivatives). Especially preferred are the compounds wherein X3 and X1 or X3 and X6 represent nitrogen. Those groups X which do not represent a nitrogen atom are preferably a CH group.

Particularly preferred are furthermore the compounds according to the invention, wherein R1 is selected from halogen and C1-C6alkoxy, preferably C1-C4alkoxy, in particular from fluoro and methoxy.

Another preferred group of the compounds according to the present invention are those, wherein A2 represents a group selected from C5-C6cycloalkylene and saturated or unsaturated 4 to 6-membered heterocyclodiyl with one or two nitrogen atoms as the heteroatom(s), in particular unsubstituted C5-C6cycloalkylene and saturated 4 to 6-membered heterocyclodiyl with one nitrogen atom as the heteroatom, in particular the compounds of formula (I) wherein A2 is selected from:

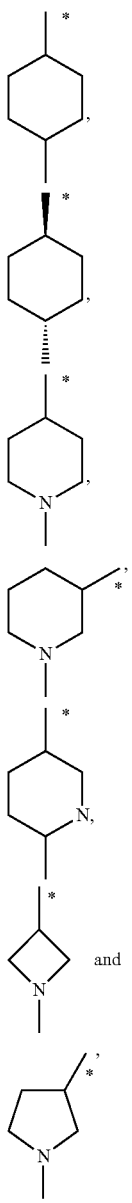

wherein
* indicates the bond to the $(CH_2)_n$ group in formula (I).

The group G in formula (I) represents preferably a C6-C10aryl group which is unsubstituted or further substituted by one or more halogen atoms, in particular chloro or fluoro, and/or straight-chain or branched C1-C4alkyl groups which may optionally be further substituted by fluoro, like e.g. trifluoromethyl; or a phenyl group or a 5- or 6-membered heteroaryl group comprising heteroatoms selected from oxygen, sulphur or nitrogen, which phenyl group or 5- or 6-membered heteroaryl group are unsubstituted or substituted by one or more halogen atoms, in particular chloro or fluoro, and/or straight-chain or branched C1-C4alkyl groups which may optionally be further substituted by fluoro, like e.g. trifluoromethyl, or by an unsubstituted 5- or 6-membered heteroaryl group, to which phenyl group or 5- or 6-membered heteroaryl group further optionally a benzene ring or a 5- or 6-membered heteroarene ring, which is unsubstituted or substituted by one or more halogen atoms, in particular chloro or fluoro, and/or straight-chain or branched C1-C4alkyl groups which may optionally be further substituted by fluoro, like e.g. trifluoromethyl, or a heterocycloalkane ring may be fused which comprises five to six ring atoms and heteroatoms selected from oxygen, sulphur or nitrogen and optionally a =O group as substituent.

Particularly preferred as group G are the following groups:

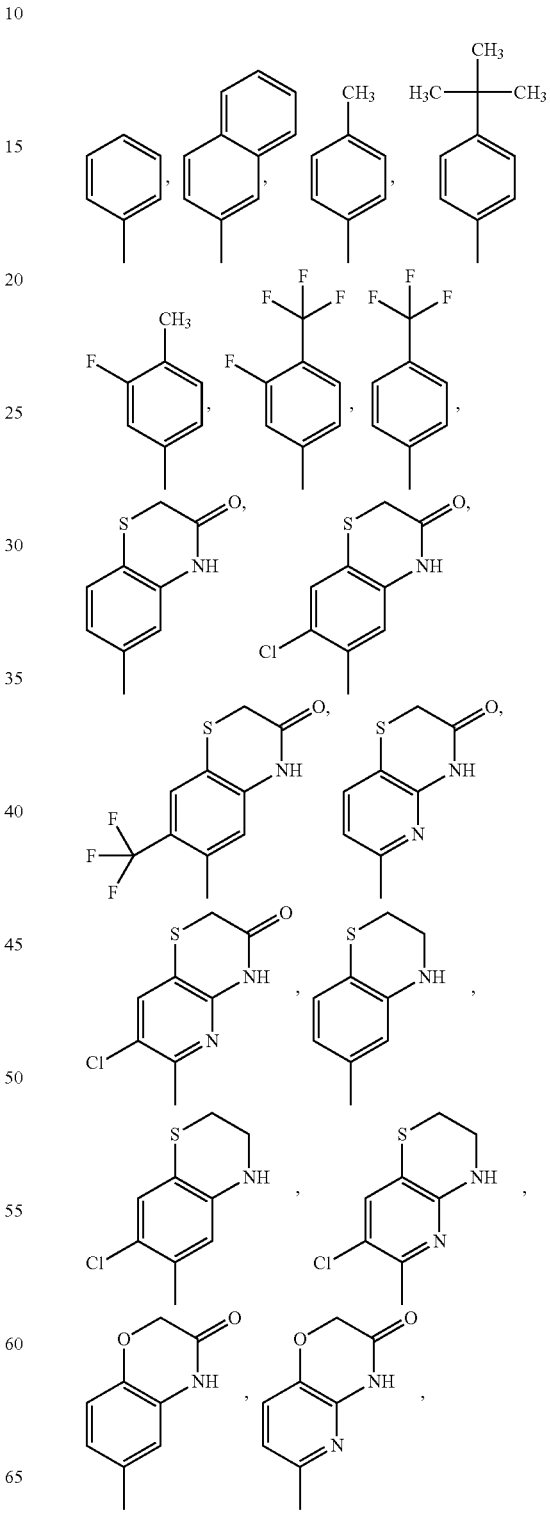

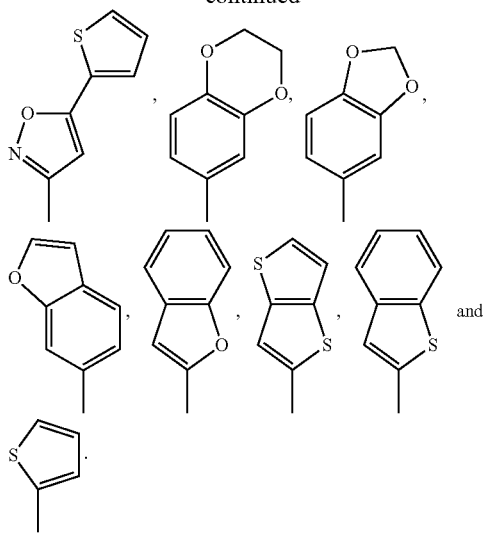

Particularly preferred in view of antibacterial activity are the compounds of formula (I) wherein A1 represents —O—$(CH_2)_m$—$(CH_2)$— or, even more preferred, —S—$(CH_2)_m$—$(CH_2)$—.

Especially preferred are these compounds when m is 1.

The compounds of formula (I) wherein n is 0 or 1 are yet a further preferred group of the compounds of the present invention.

Further specific embodiments of the present invention are:
compounds according to the invention, wherein X3 and X1 are nitrogen;
compounds according to the invention, wherein R2 is selected from hydrogen, hydroxy, halogen, C1-C6alkyl, C1-C6alkoxy, carboxy;
compounds according to the invention, wherein A2 is unsubstituted or substituted with a group selected from hydroxy, C1-C4alkyl and carboxy; and
compounds according to the invention, wherein $(CH_2)_m$ is unsubstituted or substituted with groups selected from C1-C6alkyl and C1-C6alkenyl.

All aforementioned specific embodiments or preferences can also be combined in any possible manner, and all these combinations are considered to be further embodiments of the present invention.

Examples of pharmacologically acceptable salts of the compounds of formula (I) are salts of physiologically acceptable mineral acids, such as hydrochloric acid, sulphuric acid and phosphoric acid, or salts of organic acids, such as methane-sulphonic acid, p-toluenesulphonic acid, lactic acid, acetic acid, trifluoroacetic acid, citric acid, succinic acid, fumaric acid, maleic acid and salicylic acid. Further examples of pharmacologically acceptable salts of the compounds of formula (I) are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts.

The compounds of formula (I) may also be solvated, especially hydrated. Solvation and hydration may take place, for example, during the preparation process.

The compounds according to the present invention, pharmaceutically acceptable salts, solvates or hydrates thereof can be prepared e.g. by one of the processes (a), (b) or (c) described below; followed, if necessary, by:
removing any protecting groups;
forming a pharmaceutically acceptable salt;
forming a pharmaceutically acceptable solvate or hydrate.

Process (a):
A compound of the formula II

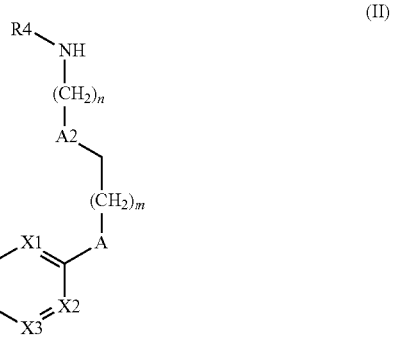

(II)

is reacted with a compound of formula (III)

G-A3b-L0          (III):

in which formulae
X1, X2, X3, X4, X5, X6, R1, A2, G, R4, m and n are as in formula I,
A represents a group selected from —O—; —S—; and —C(=O)O—, which —C(=O)O— group is linked to the adjacent $(CH_2)_m$ group via the oxygen atom,
L0 is selected from —$CH_2Y$, —CHO, —COOH and —COCl,
Y is a leaving group like methylsulfonyl, tolylsulfonyl, trifluoromethylsulfonyl or halogen,
A3b is absent or represents $C_1$-$C_3$alkylene, $C_1$-$C_3$alkenylene, or a group selected from —$CH_2NH$—, —$CH_2O$—, and —$CH_2S$—, said group being linked to G via the nitrogen, oxygen or sulfur atom, In certain cases L0 may require appropriate activation to allow a reaction of compounds of formulae II and III as described in more detail below.

Process (b):
A compound of the formula IV

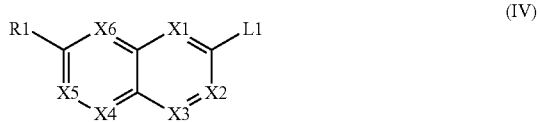

(IV)

is reacted with a compound of formula V

(V)

in which formulae
X1, X2, X3, X4, X5, X6, R1, A2, R4, m and n are as in formula I, L1 is C(=O)OH or a corresponding acid halide or otherwise activated acyl derivative, anhydride or mixed anhydride, OH, SH, Br, Cl or a group $OSO_2R$ in which R is $CH_3$, $CF_3$, or tolyl, and L2 is a halogen atom, SH, OH or a group $OSO_2R$ in which R is $CH_3$, $CF_3$, or tolyl, and L1 and L2 are selected such that the reaction results in the formation of a compound of formula VIII

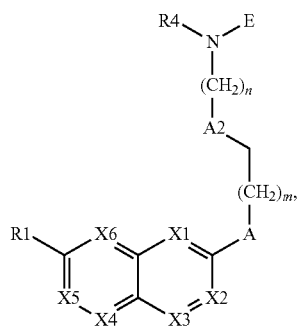
(VIII)

wherein A is as defined above,

E is -A3-G (A3 and G being as defined in formula I) or an amino protecting group, such as allyloxycarbonyl, benzyloxycarbonyl, 9-fluorenylmethylcarbonyl tert-butoxycarbonyl or benzyl, and when E is a protecting group, said protecting group is removed and the deprotected intermediate is reacted with a compound of formula III G-A3b-L0 (III):

wherein G, A3b and L0 are as defined above.

Again L0 may, in certain cases, require appropriate activation to allow connection of the deprotected intermediate and the compound of formula (III).

Process (c):

A compound of formula VI

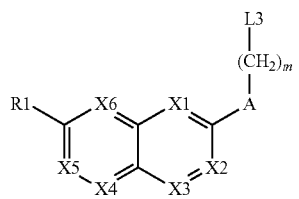
(VI)

is reacted with a compound of formula VII

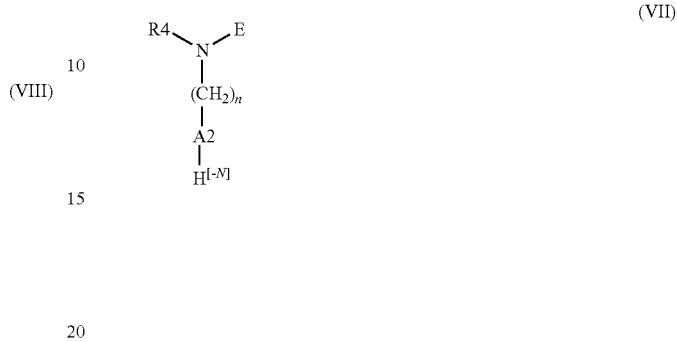
(VII)

wherein in formulae (VI) and (VII)

X1, X2, X3, X4, X5, X6, R1, R4, m and n are as in formula I,

A represents a group selected from —O—; —S—; and —C(=O)O—, the —C(=O)O— group being linked to the adjacent $(CH_2)_m$ group via the oxygen atom, A2 is an unsubstituted or substituted, saturated or unsaturated 4 to 8-membered heterocyclodiyl group with 1, 2 or 3 heteroatoms selected from nitrogen, oxygen and sulphur, at least one of which heteroatoms is nitrogen atom and $H^{[-N]}$ represents a hydrogen atom bound to bound to a nitrogen ring atom of A2, L3 is —CHO, and E is an amino protecting group or a group of formula -A3-G, wherein A3 and G have the same meaning as in formula I, and wherein when E is a protecting group, said protecting group is removed and the deprotected intermediate is reacted with a compound of formula III G-A3b-L0 (III):

wherein G, A3 and L0 are as defined above

Again L0 may, in certain cases, require appropriate activation to allow connection of the deprotected intermediate and the compound of formula (III).

The necessary starting materials for the synthetic methods as described herein, if not commercially available, may be made by procedures which are described in the scientific literature, or could be made from commercially available compounds using adaptations of processes reported in the scientific literature. The reader is further referred to *Advanced Organic Chemistry*, 5th Edition, by J. March and M. Smith, published by John Wiley & Sons, 2001, for general guidance on reaction conditions and reagents.

Furthermore in some of the reactions mentioned herein it may be necessary or desirable to protect any sensitive groups in compounds. Conventional protecting groups may be used in accordance with standard practice (for illustration see *Protective Groups in Organic Synthesis*, 3rd Edition, by T. W. Greene and P. G. M. Wuts, published by John Wiley & Sons, 1999).

The protecting groups may be removed at any convenient stage in the synthesis using conventional techniques well known in the art, or they may be removed during a later reaction step or work-up.

Scheme 1

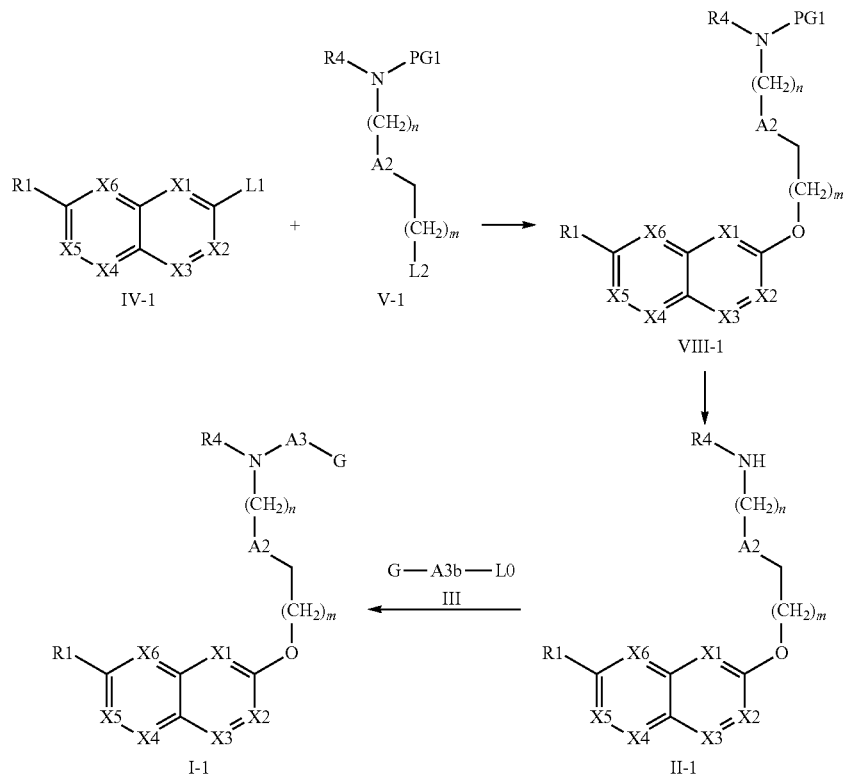

In Scheme 1, PG1 is a protecting group (such as allyloxycarbonyl (Alloc), benzyloxycarbonyl, 9-fluorenylmethylcarbonyl (Fmoc), tert-butoxycarbonyl (Boc) or benzyl), L1 and L2 are halogen, in particular Br, Cl, or OH, and the other symbols have the same meanings as previously described.

Compounds of formula V-1 are usually obtained by reacting the corresponding free amine with allyl, fluorenylmethyl or benzyl chloroformate or with di tert-butyl dicarbonate in presence of a base such as sodium hydroxide, sodium hydrogencarbonate, triethylamine, 4-dimethylaminopyridine or imidazole. They can also be protected as N-benzyl derivatives by reaction with benzyl bromide or chloride in presence of a base such as sodium carbonate or triethylamine. Alternatively, N-benzyl derivatives can be obtained through reductive amination in presence of benzaldehyde. Further strategies to introduce other amine protecting groups have been described in *Protective Groups in Organic Synthesis*, 3$^{rd}$ Edition, by T. W. Greene and P. G. M. Wuts, published by John Wiley & Sons, 1999.

Compounds of formula VIII-1 (Scheme 1) can be obtained from compounds of formula V-1 wherein L2 is —OH via a Mitsunobu coupling (as reviewed in O. Mitsunobu, Synthesis 1981, 1) with compounds of formula IV-1 for which L1 is a hydroxy group. The reaction is for example performed in the presence of diethyl or diisopropyl azodicarboxylate and triphenylphosphine, in a wide range of solvents such as N,N-dimethylformamide, tetrahydrofuran, 1,2-dimethoxyethane or dichloromethane and within a wide range of temperatures (between −20° C. and 60° C.). The reaction might also be performed using polymer-supported triphenylphosphine.

An alternative route to form compounds of formula VIII-1 consists of reacting compounds of formula V-1 wherein L2 is —OH with compounds of formula IV-1 for which L1 is a hydroxy group, which needs to be activated prior to the reaction as described below or a halogen atom in presence of an inorganic base such as sodium hydride or the like in a solvent such as dichloromethane or N,N-dimethylformamide at a temperature ranging between −20° C. and 80° C. Activation of the hydroxy group of compounds of formula V-1 wherein L1 is —OH as for example a mesylate, a tosylate or a triflate can be achieved by reacting the compound of formula V-1 wherein L1 is —OH with methanesulfonyl chloride or methanesulfonic anhydride, p-toluenesulfonyl chloride, trifluoromethanesulfonyl chloride or trifluoromethanesulfonic anhydride, respectively, in presence of a base such as triethylamine or the like in a dry aprotic solvent such as pyridine, acetonitrile, tetrahydrofuran or dichloromethane between −30° C. and 60° C.

Finally, compounds of formula VIII-1 can be generated by reacting compound of formula IV-1 wherein L1 is a hydroxy group with a compound of formula V-1 wherein L2 is a halogen atom or a hydroxyl group which needs to be activated prior to the reaction as for example a mesylate, tosylate or triflate as described above. The coupling is performed in presence of an inorganic base such as sodium hydride in a solvent such as dichloromethane or N,N-dimethylformamide at a temperature ranging between −20° C. and 80° C.

Removal of the protecting group PG1 in compounds of formula VIII-1 is carried out under standard conditions to generate compounds of formula II-1. For example the benzyl carbamates are deprotected by hydrogenolysis over a noble catalyst (e.g. palladium on activated carbon). The Boc group is removed under acidic conditions such as hydrochloric acid in an organic solvent such as ethyl acetate, or trifluoroacetic acid neat or diluted in a solvent such as dichloromethane. The Alloc group is removed in presence of a palladium salt such as palladium acetate or tetrakis(triphenylphosphine)palladium (0) and an allyl cation scavenger such as morpholine, pyrrolidine, dimedone or tributylstannane between 0° C. and 70° C. in a solvent such as tetrahydrofuran. The N-benzyl protected amines are deprotected by hydrogenolysis over a noble catalyst (e.g. palladium dihydroxide). The Fmoc protecting group is removed under mild basic conditions such as diluted morpholine or piperidine in N,N-dimethylformamide. Further general methods to remove amine protecting groups have been described in *Protective Groups in Organic Synthesis*, 3$^{rd}$ Edition, by T.W. Greene and P.G.M. Wuts, published by John Wiley & Sons, 1999.

Compounds of formula I-1 wherein A3 is $CH_2$ can be obtained from intermediate II-1 (Scheme 1) by reaction with a compound of formula III wherein L0 is —CHO either in the presence of or followed by a reaction with a suitable reducing agent. The reaction between the amine and the aldehyde to form an intermediate imine is conducted in a solvent system allowing the removal of the formed water through physical or chemical means (e.g. distillation of the solvent-water azeotrope or presence of drying agents such as molecular sieves, magnesium sulfate or sodium sulfate). Such solvents are typically toluene, n-hexane, tetrahydrofuran, dichloromethane, N,N-dimethylformamide, N,N-dimethylacetamide, acetonitrile, 1,2-dichloroethane or mixture of solvents such as methanol:1,2-dichloroethane. The reaction can be catalyzed by traces of acid (usually acetic acid). The imine is reduced subsequently or simultaneously with a suitable reagent such as sodium borohydride, sodium triacetoxyborohydride or sodium cyanoborohydride (R. O. and M. K. Hutchins, *Comprehensive Organic Synthesis*, B. M. Trost, I. Fleming, Eds; Pergamon Press: New York (1991), vol. 8, p. 25-78). The reaction is preferably carried out between 0° C. and 60° C.

Compounds of formula I-1 wherein A3 is >C(=O) can be obtained from intermediate II-1 (Scheme 1) through reaction with a carboxylic acid derivative III (L0=COOH), in the presence of an activating agent such as N,N'-dicyclohexylcarbodiimide or N-(3-dimethylaminopropyl)-N'-ethylcarbodiimide hydrochloride, with the optional addition of 1-hydroxybenzotriazole. Other suitable coupling agents may be utilized such as, O-(7-azabenzotriazol-1-yl)-N,N,N',N'-tetramethyluronium hexafluorophosphate, 2-ethoxy-1-ethoxycarbonyl-1,2-dihydroquinoline, carbonyldiimidazole or diethylphosphorylcyanide. Optionally, a base like triethylamine, N,N-diisopropylethylamine or pyridine can be added to perform the coupling. The peptidic coupling is conducted at a temperature comprised between −20° C. and 80° C., in an inert solvent, preferably a dry aprotic solvent like dichloromethane, acetonitrile or N,N-dimethylformamide and chloroform. Alternatively, the carboxylic acid can be activated by conversion into its corresponding acid chloride or its corresponding activated ester, such as the N-hydroxysuccinimidyl ester (Org. Process Res. & Dev., 2002, 863) or the benzothiazolyl thioester (J. Antibiotics, 2000, 1071). The generated activated entity can react at a temperature comprised between −20° C. and 80° C. with compound of formula II-1 in an aprotic solvent like dichloromethane, chloroform, acetonitrile, N,N-dimethylformamide and tetrahydrofuran to generate compound of formula I-1. Optionally, a base like triethylamine, N,N-diisopropylethylamine, pyridine, sodium hydroxide, sodium carbonate, potassium carbonate can be added to perform the coupling.

Alternatively, compounds of formula I-1 wherein A3 is —$CH_2$— can be obtained from intermediate II-1 by reaction with a compound of formula III wherein L0 is —$CH_2$Y and Y is a leaving group like methylsulfonyl, tolylsulfonyl, trifluoromethylsulfonyl or halogen at a temperature between −20° C. and 100° C. in a dry aprotic solvent like dichloromethane, acetonitrile, N,N-dimethylformamide or tetrahydrofuran without or with a base such as potassium carbonate or N,N-diisopropylethylamine.

In Scheme 1, coupling of compounds of general formulae IV-1 and V-1, followed by a deprotection step and finally introduction of the A3-G substituent allowed the generation of compounds of formula I-1. Alternatively, the protecting group PG1 of compounds of formula V-1 can be removed according to the methods described above and the product of this reaction can then be reacted with one of the compounds of formula III as defined above. Subsequently, these intermediates are converted into compounds of formula I-1 following the methods described above for the synthesis of compounds of formula VIII-1.

Scheme 2

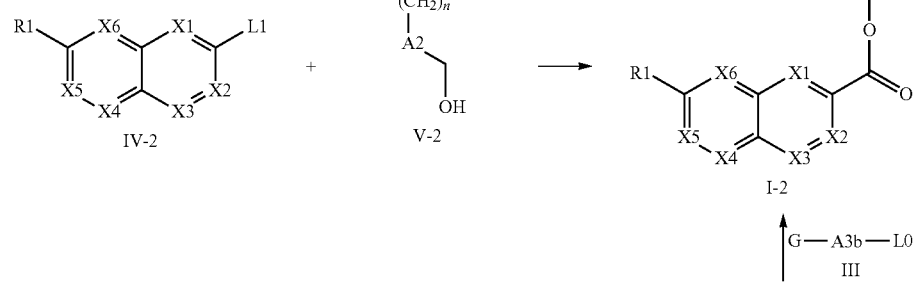

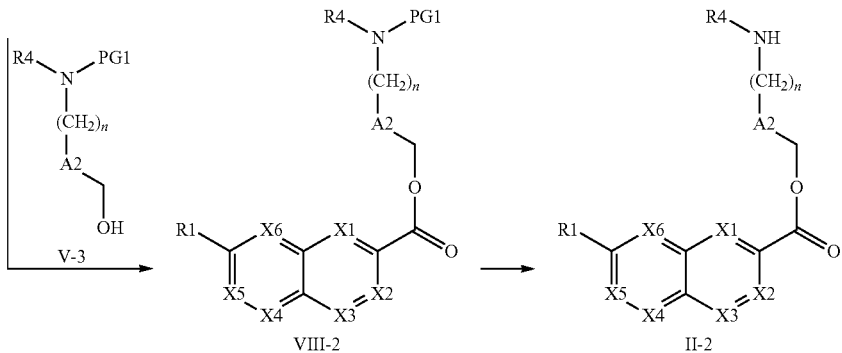

In Scheme 2, L1 is a carboxylic acid C(O)—OH or its corresponding acid halide or other activated acyl derivatives, anhydride or mixed anhydride. All the other symbols have the same meanings as in formula I or in Scheme 1.

The reaction between compounds of formulae IV-2 wherein L1 is COOH and V-2 to generate compounds of formula I-2 is performed with the addition of a coupling agent such as N,N'-dicyclohexylcarbodiimide or the like, and optionally with the addition of 4-dimethylaminopyridine, imidazole or the like. The reaction between compounds of formula IV-2 wherein L1 is an acid halide, or any other activated acyl derivative and V-2 to generate compounds of formula I-2 is performed in the presence of a base such as triethylamine or sodium hydride and optionally 4-dimethylaminopyridine. The acylation is conducted at a temperature comprised between −20° C. and 60° C., in an inert solvent, preferably a dry aprotic solvent like dichloromethane, acetonitrile, N,N-dimethylformamide or chloroform.

Alternatively, compounds of formula I-2 can be generated by first coupling compounds of formulae IV-2 and V-3 according to the methods described above to generate the intermediate VIII-2 and subsequent removal of the protecting group PG1 and introduction of the substituent A3-G following procedures previously described for Scheme 1.

Scheme 3

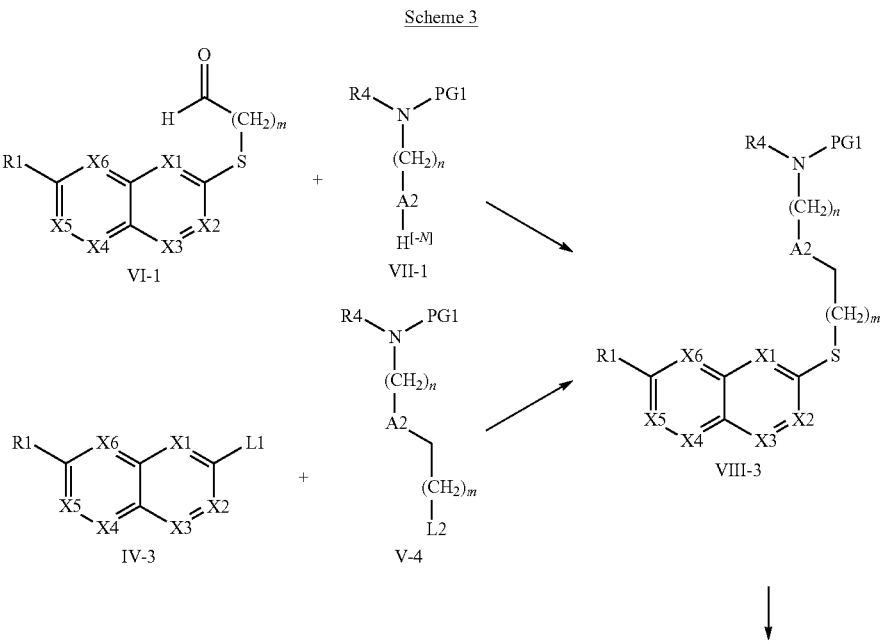

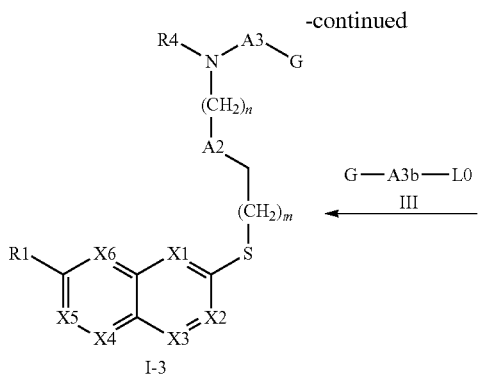

I-3

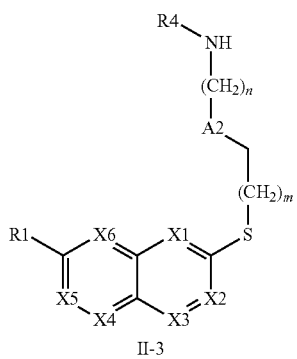

II-3

In Scheme 3, L1 and L2 are SH, Br, Cl or the group $OSO_2R$ in which R is $CH_3$, $CF_3$, or tolyl and all the other symbols have the same meanings as in formula I or in Scheme 1.

In the case where A2 in compound VIII-3 is a saturated or unsaturated 4 to 8-membered heterocyclodiyl group, which is linked to the $—CH_2—(CH_2)_m—S—$ group via a ring nitrogen atom, the compounds of formula VIII-3 can be obtained via reductive amination between VI-1 and VII-1 following procedures previously described in conjunction with Scheme 1 for the preparation of compounds of formula I-1 wherein A3 is $CH_2$ by reaction of an intermediate II-1 with a compound of formula III wherein L0 is —CHO.

Alternatively, compounds of formula VIII-3 can be obtained by reacting compounds of formula IV-3 for which L1 is SH with compounds of formula V-4 for which L2 is Br, Cl or the group $OSO_2R$ in which R is $CH_3$, $CF_3$, or tolyl in presence of a base such as sodium hydroxide, sodium hydride, sodium carbonate, potassium hydroxide, potassium carbonate, triethylamine in a solvent such as acetone, acetonitrile, ethanol, isopropanol or N,N-dimethylformamide at a temperature ranging between 0° C. and 120° C. In this procedure, the mesylate, tosylate or triflate derivatives are generated from the corresponding alcohol following procedures previously described for Scheme 1.

Alternatively, compounds of formula VIII-3 can be obtained by reacting compounds of formula IV-3 for which L1 is Br, Cl or the group $OSO_2R$ in which R is $CH_3$, $CF_3$, or tolyl with compounds of formula V-4 where L2 is SH. In that case, the reaction can be performed in presence of a palladium salt such as palladium acetate or tetrakis(triphenylphosphine)palladium(0) with the optional addition of a base such as sodium tert-butylate in a solvent such as toluene, N,N-dimethylformamide, dioxane at a temperature ranging from 0° C. and 150° C.

The intermediates VIII-3 are further transformed into compounds of formula I-3 using synthetic routes previously described for Scheme 1.

Alternatively, the protecting group PG1 of compounds of formula V-4 can be removed and the product of this reaction can then be reacted with a compound of formula III according to the methods described above. Subsequently, these intermediates are reacted with compounds of formula IV-3 to give the compounds of formula I-3 following the methods described above for the synthesis of compounds of formula VIII-1.

Starting Materials:

Unless otherwise stated the required starting compounds of formulae IV and VI are commercially available or prepared following literature procedures. For example, quinoxalines (IV; X2=X4=X5=X6=CH, X1=X3=N) may be prepared from the corresponding anilines following standard routes as described in J. Med. Chem., 2001, 44, 1758, J. Chem. Soc., 1949, 1271 and PCT Pub. No. WO2004/014871; [1,5]-naphthyridines (IV; X1=X2=X4=X5=CH, X3=X6=N) and quinolines (IV; X3=N, X1=X2=X4=X5=X6=CH) can be prepared from the corresponding aminopyridines or anilines, respectively, by applying standard procedures as described in J. Med. Chem., 2002, 45, 3130 and the patent literature, such as PCT Pub. No. WO2004/058144, WO95/00511, U.S. Pat. No. 5,442,065, EP0293071.

Unless otherwise stated the required starting derivatives of formulae V and VII are prepared following or adapting synthetic procedures described in the patent literature, such as PCT Pub. No. WO2006/099884 and WO2006/004949.

Unless otherwise stated compounds of formula III-1, III-2 and III-3 are commercially available or may be obtained by procedures described in the patent literature, such as PCT Pub. No. WO2007/093507, WO2007/052843, WO2006/105289, WO2006/038734, WO2006/021448, WO2004/058144, WO2004/002992, WO02/34754.

When an optically active form of a compound of the invention is required, it may be obtained by carrying out one of the above procedures using a pure enantiomer or diastereomer as a starting material, or by resolution of a mixture of the enantiomers or diastereomers of the final product or intermediate using a standard procedure. The resolution of enantiomers may be achieved by chromatography on a chiral stationary phase, such as REGIS PIRKLE COVALENT (R-R) WHELK-02, 10 μm, 100 Å, 250×21.1 mm column. Alternatively, resolution of stereoisomers may be obtained by preparation and selective crystallization of a diastereomeric salt of a chiral intermediate or chiral product with a chiral acid, such as camphorsulfonic acid. Alternatively a method of stereoselective synthesis may be employed, for example by using a chiral variant of a protecting group, a chiral catalyst or a chiral reagent where appropriate in the reaction sequence.

Enzymatic techniques may also be useful for the preparation of optically active compounds and/or intermediates.

Further aspects of the invention include pharmaceutical compositions comprising a compound of formula (I) or a pharmaceutically acceptable salt, a hydrate or solvate thereof and a pharmaceutically acceptable carrier;

the compounds of formula (I) or a pharmaceutically acceptable salt, a hydrate or solvate thereof for use as a medicament, in particular a medicament for the treatment of bacterial infections; and the use of a compound of formula (I) or a pharmaceutically acceptable salt, a hydrate or solvate thereof for the preparation of medicaments for the treatment of infectious diseases caused by bacteria.

The compounds of number 1, 2, 3, 4, 5, 6, 7, 8, 9, 14, 15, 16, 17, 18, 19, 20, 28, 29, 30, 31, 35, 36, 37, 38, 39, 40, 41, 42, 43, 44, 45, 46, 47, 48, 49, 50, 51, 52, 53, 54, 55 and 56 indicated in Table 1 below are particularly advantageous for the treatment of infections by *Staphylococcus aureus* and/or *Staphylococcus epidermidis* and exhibit a MIC for said strains of generally ≤2 mg/L.

The compounds of number 2, 5, 9, 35, 36, 37, 38, 39, 40, 41, 42, 43, 45, 46, 47, 48, 49, 50, 52, 53 and 55 indicated in Table 1 below are particularly advantageous for the treatment of infections by *Staphylococcus aureus* and/or *Staphylococcus epidermidis* and/or *Streptococcus pneumoniae* and exhibit a MIC for said strains of generally ≤2 mg/L.

The compounds of number 9, 36, 37, 40, 44, 45, 46, 48, 49, 50, 51, 53 and 54 indicated in Table 1 below are particularly advantageous for the treatment of infections by *Staphylococcus aureus* and/or *Staphylococcus epidermidis* and/or *Streptococcus pneumoniae* and/or *Escherichia coli* and exhibit a MIC for said strains of generally ≤4 mg/L, in most case of less than 2 mg/L.

Furthermore, the compounds selected from the compounds of number 58, 62, 63, 67, 71, 73, 76, 78, 79, 80, 81, 94, 95, 101, 102, 103, 104, 105, 113, 114, and 122 are particularly useful for the treatment of infections by *Staphylococcus aureus* and/or *Staphylococcus epidermidis*, the compounds of number 67, 78, 81, 95, 102, 103, 104, 105 and 122 for the treatment of infections by *Staphylococcus aureus* and/or *Staphylococcus epidermidis* and/or *Streptococcus pneumoniae* and the compounds of number 102 and 103 for use as a medicament against infections by *Staphylococcus aureus* and/or *Staphylococcus epidermidis* and/or *Streptococcus pneumoniae* and/or *Escherichia coli*.

In general, compounds of formula (I) are administered either individually, or optionally also in combination with another desired therapeutic agent, using the known and acceptable methods. Such therapeutically useful agents may be administered, for example, by one of the following routes: orally, for example in the form of dragees, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or a spray; transdermally or intranasally.

For the preparation of such tablets, pills, semi-solid substances, coated tablets, dragees and hard gelatine capsules, the therapeutically usable product may be mixed with pharmacologically inert, inorganic or organic pharmaceutical carrier substances, for example with lactose, sucrose, glucose, gelatine, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat and polyols may be used.

For the preparation of liquid solutions and syrups, pharmaceutical carrier substances such as, for example, water, alcohols, aqueous saline solution, aqueous dextrose, polyols, glycerol, vegetable oils, petroleum and animal or synthetic oils may be used.

For suppositories, pharmaceutical carrier substances such as, for example, vegetable oils, petroleum, animal or synthetic oils, wax, fat and polyols may be used.

For aerosol formulations, compressed gases that are suitable for this purpose, such as, for example, oxygen, nitrogen and carbon dioxide may be used. The pharmaceutically acceptable agents may also comprise additives for preserving and stabilising, emulsifiers, sweeteners, flavourings, salts for altering the osmotic pressure, buffers, encapsulation additives and antioxidants.

Combinations with other therapeutic agents which are also encompassed by the present invention may comprise one, two or more other antimicrobial and anti-fungal active ingredients.

For the prevention and/or treatment of bacterial infections, the dose of the biologically active compound according to the invention may vary within wide limits and may be adjusted to individual requirements. Generally, a dose of 10 mg to 4000 mg per day is suitable, a preferred dose being from 50 to 3 000 mg per day. In suitable cases, the dose may also be below or above the stated values. The daily dose may be administered as a single dose or in a plurality of doses. A typical individual dose contains approximately 50 mg, 100 mg, 250 mg, 500 mg, 1 g or 2 g of the active ingredient.

EXAMPLES

Particular embodiments of the invention are described in the following Examples, which serve to illustrate the invention in more detail:

All reagents and anhydrous solvents are generally used as received from the commercial supplier;

reactions are routinely performed in well-dried glassware under an argon or nitrogen atmosphere;

evaporations are carried out by rotary evaporation in vacuo and work-up procedures are carried out after removal of residual solids by filtration;

all temperatures are given in ° C.; operations are carried at room temperature, that is typically in the range 18-25° C.;

column chromatography (by the flash procedure) is used to purify compounds and is performed using Merck silica gel 60 (70-230 mesh ASTM) unless otherwise stated; in general, the course of reactions is followed by TLC, HPLC, or LC/MS and reaction times are given for illustration only; yields are given for illustration only and are not necessarily the maximum attainable;

the structure of the final products of the invention is generally confirmed by NMR and mass spectral techniques. Proton NMR spectra are recorded on a Brucker 400 MHz spectrometer. Chemical shifts (δ) are reported in ppm relative to $Me_4Si$ as internal standard, and J values are in Hertz (Hz). Each peak is denoted as a broad singlet (br), singlet (s), doublet (d), doublet of doublets (dd), triplet of doublets (td) or multiplet (m). Mass spectra are generated using a q-T of Ultima (Waters AG) mass spectrometer in the positive ESI mode. The system is equipped with the standard Lockspray interface; each intermediate is purified to the standard required for the subsequent stage and is characterized in sufficient detail to confirm that the assigned structure is correct;

all analytical and preparative HPLC investigations on non-chiral phases are performed using RP-C18 based columns;

the following abbreviations may be used:

Acetone-d6: Deuterated acetone $CDCl_3$: Deuterated chloroform

DMSO-d6: Deuterated dimethyl sulphoxide

ELSD: Evaporative light scattering detection

HPLC: High performance liquid chromatography

J: Coupling constant

LC/MS: Liquid chromatography coupled to mass spectoscopy

MeOH-d4: Deuterated methanol
Me₄Si: Tetramethylsilane
MS: Mass spectroscopy
NMR: Nuclear magnetic resonance
TLC: Thin layer chromatography The following Examples refer to the compounds of formula I as indicated in Table 1 (A in Table 1 is O when A1 in formula (I) is —O—$(CH_2)_m$—$(CH_2)$— or S when A1 is —S—$(CH_2)_m$—$(CH_2)$— or $CO_2$ when A1 is —(C=O)O—$(CH_2)_m$—$(CH_2)$—):

TABLE 1

Exemplified compounds

| Expl./Comp. | (ring) | A | A2 | A3 | R4 | m | n | G |
|---|---|---|---|---|---|---|---|---|
| 1 | 7-Methoxy-quinoxaline | O | piperidine | C=O | H | 1 | 0 | 6-methyl-2H-benzo[b][1,4]thiazin-3(4H)-one |
| 2 | 6-Methoxy-[1,5]naphthyridine | O | cyclohexyl (trans) | C=O | H | 1 | 0 | 6-methyl-2H-benzo[b][1,4]thiazin-3(4H)-one |
| 3 | 6-Methoxy-[1,5]naphthyridine | O | cyclohexyl (trans) | C=O | H | 1 | 0 | 6-methyl-pyrido[3,2-b][1,4]oxazin-3(4H)-one |
| 4 | 7-Methoxy-quinoxaline | O | cyclohexyl (trans) | C=O | H | 1 | 0 | 6-methyl-2H-benzo[b][1,4]thiazin-3(4H)-one |

TABLE 1-continued

Exemplified compounds

| Expl./Comp. | A | A2 | A3 | R4 | m | n | G |
|---|---|---|---|---|---|---|---|
| 5 | 7-Methoxy-quinoxaline | piperidine | C=O | H | 1 | 0 | 3-methyl-5-(thiophen-2-yl)isoxazole |
| 6 | 6-Methoxy-[1,5]naphthyridine | trans-cyclohexane | C=O | H | 1 | 0 | 6-methyl-2H-benzo[b][1,4]oxazin-3(4H)-one |
| 7 | 7-Fluoro-quinoxaline | trans-cyclohexane | C=O | H | 1 | 0 | 6-methyl-2H-benzo[b][1,4]thiazin-3(4H)-one |
| 8 | 7-Methoxy-quinoxaline | azetidine | C=O | H | 2 | 0 | 6-methyl-2H-benzo[b][1,4]thiazin-3(4H)-one |
| 9 | 7-Methoxy-quinoxaline | piperidine | CH$_2$ | H | 2 | 1 | 6-methyl-2H-pyrido[3,2-b][1,4]oxazin-3(4H)-one |

TABLE 1-continued

Exemplified compounds

| Expl./Comp. | A | A2 | A3 | R4 | m | n | G |
|---|---|---|---|---|---|---|---|
| 10 | 7-Methoxy-quinoxaline, O | piperidine (4-position) | CH₂ | Me | 1 | 0 | 6-methyl-2,3-dihydro-1,4-benzodioxine |
| 11 | 7-Methoxy-quinoxaline, O | 3,3-dimethyl piperidine | CH₂ | H | 2 | 0 | 6-methyl-4H-benzo[b][1,4]thiazin-3-one |
| 12 | 8-Methoxy-quinoxaline, O | piperidine (4-position) | C=O | H | 1 | 0 | 6-methyl-4H-benzo[b][1,4]thiazin-3-one |
| 13 | 7-Nitro-quinoxaline, O | piperidine (4-position) | C=O | H | 1 | 0 | 6-methyl-4H-benzo[b][1,4]thiazin-3-one |
| 14* | 7-Methoxy-quinoxaline, O | piperidine (4-position) | C=O | H | 1 | 0 | 6-methyl-4H-benzo[b][1,4]thiazin-3-one |

TABLE 1-continued

Exemplified compounds

| Expl./Comp. | A | A2 | A3 | R4 | m | n | G |
|---|---|---|---|---|---|---|---|
| 15 | 7-Methoxy-quinoxaline | O | piperidine (4-yl, N-) | C=O | H | 1 | 0 | 6-methyl-7-chloro-2H-1,4-benzothiazin-3(4H)-one |
| 16 | 6-Methoxy-[1,5]naphthyridine | O | piperidine (4-yl, N-) | C=O | H | 1 | 0 | 6-methyl-7-chloro-2H-1,4-benzothiazin-3(4H)-one |
| 17 | 7-Methoxy-quinoline | O | piperidine (4-yl, N-) | C=O | H | 1 | 0 | 6-methyl-pyrido[3,2-b][1,4]thiazin-3(4H)-one |
| 18 | 7-Methoxy-[1,5]naphthyridine | O | piperidine (4-yl, N-) | C=O | H | 1 | 0 | 6-methyl-2H-1,4-benzothiazin-3(4H)-one |
| 19 | 7-Methoxy-[1,5]naphthyridine | O | piperidine (4-yl, N-) | C=O | H | 1 | 0 | 6-methyl-7-chloro-2H-1,4-benzothiazin-3(4H)-one |

TABLE 1-continued

Exemplified compounds

| Expl./Comp. | A | A2 | A3 | R4 | m | n | G |
|---|---|---|---|---|---|---|---|
| 20 | 7-Methoxy-quinoxaline | O | piperidine (4-yl, N-linked) | C=O | H | 1 | 0 | 6-methyl pyrido-thiazinone |
| 21 | Quinoxaline | O | piperidine (4-yl, N-linked) | C=O | H | 1 | 0 | 6-methyl benzothiazinone |
| 22 | 7-Methoxy-quinoxaline | O | azetidine (3-yl, N-linked) | C=O | H | 1 | 0 | 6-methyl benzothiazinone |
| 23 | 7-Methoxy-quinoxaline | O | pyrrolidine (3-yl, N-methyl) | C=O | H | 2 | 0 | 6-methyl benzothiazinone |
| 24 | 7-Methoxy-quinoxaline | O | piperidine (4-yl, N-linked) | C=O | H | 1 | 1 | 6-methyl-7-chloro benzothiazinone |

TABLE 1-continued

Exemplified compounds

| Expl./Comp. | A | A | A2 | A3 | R4 | m | n | G |
|---|---|---|---|---|---|---|---|---|
| 25 | 7-Methoxy-quinoxaline | O | piperidine (4-yl, N-linked) | CH₂ | Me | 1 | 0 | 6-methyl-2H-benzo[b][1,4]thiazin-3(4H)-one |
| 26 | 7-Methoxy-quinoxaline | O | 3-pyrrolidinyl | C=O | H | 1 | 1 | 3-methyl-5-(thiophen-2-yl)isoxazole |
| 27 | 7-Methoxy-quinoxaline | O | 3-pyrrolidinyl | C=O | H | 2 | 1 | 7-chloro-6-methyl-3,4-dihydro-2H-benzo[b][1,4]thiazine |
| 28 | 6-Methoxy-quinoline | CO₂ | trans-cyclohexane-1,4-diyl | C=O | H | 0 | 0 | 6-methyl-2H-benzo[b][1,4]thiazin-3(4H)-one |
| 29 | 6-Methoxy-[1,5]naphthyridine | CO₂ | trans-cyclohexane-1,4-diyl | CH₂ | H | 0 | 0 | 6-methyl-2,3-dihydrobenzo[b][1,4]dioxine |

TABLE 1-continued

Exemplified compounds

| Expl./Comp. | A | A | A2 | A3 | R4 | m | n | G |
|---|---|---|---|---|---|---|---|---|
| 30 | 6-Methoxy-[1,5]naphthyridine | $CO_2$ | cyclohexyl | C=O | H | 0 | 0 | methyl-pyrido-oxazinone |
| 31 | 6-Methoxy-[1,5]naphthyridine | $CO_2$ | cyclohexyl | $C_2H_4-S$ | H | 0 | 0 | methyl-thiophene |
| 32 | 6-Methoxy-quinoline | $CO_2$ | cyclohexyl | $CH_2$ | Me | 0 | 0 | methyl-benzodioxine |
| 33 | 6-Methoxy-quinoline | $CO_2$ | cyclohexyl | $CH_2$ | H | 0 | 0 | methyl-benzodioxine |
| 34 | 6-Methoxy-quinoline | $CO_2$ | cyclohexyl | $CH_2$ | Et | 0 | 0 | methyl-benzodioxine |

TABLE 1-continued

Exemplified compounds

| Expl./Comp. | [R1-X6-X5-X4-X3-X2-X1 ring] | A | A2 | A3 | R4 | m | n | G |
|---|---|---|---|---|---|---|---|---|
| 35 | 7-Methoxy-quinoxaline | S | piperidine (4-yl, N-linked) | C=O | H | 1 | 0 | 3-methyl-5-(thiophen-2-yl)isoxazole |
| 36 | 7-Methoxy-quinoxaline | S | piperidine (4-yl, N-linked) | C=O | H | 1 | 0 | 6-methyl-2H-benzo[b][1,4]oxazin-3(4H)-one |
| 37 | 7-Methoxy-quinoxaline | S | piperidine (4-yl, N-linked) | C=O | H | 1 | 0 | 7-chloro-6-methyl-2H-benzo[b][1,4]thiazin-3(4H)-one |
| 38 | 7-Methoxy-quinoxaline | S | piperidine (4-yl, N-linked) | C$_2$H$_4$—S | H | 1 | 0 | 2-methylthiophene |
| 39 | 7-Methoxy-quinoxaline | S | piperidine (4-yl, N-linked) | C=O | H | 1 | 0 | 6-methyl-2,3-dihydrobenzo[b][1,4]dioxine |

TABLE 1-continued

Exemplified compounds

| Expl./Comp. | A | A2 | A3 | R4 | m | n | G |
|---|---|---|---|---|---|---|---|
| 40 | 7-Methoxy-quinoxaline | S | piperidin-4-yl | CH₂ | H | 1 | 0 | 6-methyl-2H-benzo[b][1,4]oxazin-3(4H)-one |
| 41 | 7-Methoxy-quinoxaline | S | piperidin-4-yl | CH₂ | H | 1 | 0 | 6-methyl-2,3-dihydrobenzo[b][1,4]dioxine |
| 42 | 7-Methoxy-quinoxaline | S | piperidin-4-yl | CH₂ | H | 1 | 0 | 3-methyl-5-(thiophen-2-yl)isoxazole |
| 43 | 7-Methoxy-quinoxaline | S | piperidin-4-yl | CH₂ | Me | 1 | 0 | 6-methyl-2,3-dihydrobenzo[b][1,4]dioxine |
| 44 | 7-Methoxy-quinoxaline | S | piperidin-4-yl | C=O | H | 1 | 0 | 7-chloro-6-methyl-3,4-dihydro-2H-benzo[b][1,4]thiazine |

TABLE 1-continued

Exemplified compounds

| Expl./Comp. | A | A2 | A3 | R4 | m | n | G |
|---|---|---|---|---|---|---|---|
| 45 | 7-Methoxy-quinoxaline | S | piperidine | CH₂ | H | 1 | 0 | 6-methyl-pyrido[3,2-b][1,4]oxazin-3(4H)-one |
| 46 | 7-Methoxy-quinoxaline | S | piperidine | CH₂ | H | 1 | 0 | 6-methyl-2H-benzo[b][1,4]thiazin-3(4H)-one |
| 47 | 7-Methoxy-quinoxaline | S | piperidine | CH₂ | Et | 1 | 0 | 6-methyl-2,3-dihydrobenzo[b][1,4]dioxine |
| 48 | 7-Methoxy-quinoxaline | S | piperidine | CH₂ | H | 1 | 0 | 7-chloro-6-methyl-2H-benzo[b][1,4]thiazin-3(4H)-one |
| 49 | 7-Methoxy-quinoxaline | S | piperidine | CH₂ | H | 1 | 0 | 7-chloro-6-methyl-3,4-dihydro-2H-benzo[b][1,4]thiazine |

TABLE 1-continued

Exemplified compounds

| Expl./Comp. | A | A2 | A3 | R4 | m | n | G |
|---|---|---|---|---|---|---|---|
| 50 | 7-Methoxy-quinoxaline | S | piperidine | C=O | H | 1 | 0 | 6-methyl-pyrido[3,2-b][1,4]thiazin-3(4H)-one |
| 51 | 7-Methoxy-quinoxaline | S | piperidine | C=O | H | 1 | 0 | 7-chloro-6-methyl-pyrido[3,2-b][1,4]thiazin-3(4H)-one |
| 52 | 7-Methoxy-quinoxaline | S | piperidine | C=O | Me | 1 | 0 | 6-methyl-2H-benzo[b][1,4]thiazin-3(4H)-one |
| 53 | 6-Methoxy-quinoline | S | piperidine | C=O | H | 1 | 0 | 6-methyl-2H-benzo[b][1,4]thiazin-3(4H)-one |
| 54 | 6-Methoxy-quinoline | S | piperidine | C=O | H | 1 | 0 | 7-chloro-6-methyl-2H-benzo[b][1,4]thiazin-3(4H)-one |

TABLE 1-continued

Exemplified compounds

| Expl./Comp. | (ring with R1, X1–X6) | A | A2 | A3 | R4 | m | n | G |
|---|---|---|---|---|---|---|---|---|
| 55 | 6-Methoxy-quinoline | S | piperidine | C=O | H | 1 | 0 | 6-methyl-pyrido[3,2-b][1,4]thiazin-3-one |
| 56 | 6-Methoxy-quinoline | S | piperidine | C=O | H | 1 | 0 | 7-chloro-6-methyl-pyrido[3,2-b][1,4]thiazin-3-one |
| 57 | 7-Hydroxy-quinoxaline | O | piperidine | C=O | H | 1 | 0 | 6-methyl-4H-benzo[1,4]thiazin-3-one |
| 58 | 7-Ethoxy-quinoxaline | O | piperidine | C=O | H | 1 | 0 | 6-methyl-4H-benzo[1,4]thiazin-3-one |
| 59 | Acetic acid-quinoxalin-6-yl ester | O | piperidine | C=O | H | 1 | 0 | 6-methyl-4H-benzo[1,4]thiazin-3-one |

TABLE 1-continued

Exemplified compounds

| Expl./Comp. | [quinoxaline core structure with R1, X1-X6] | A | A2 [piperidine] | A3 | R4 | m | n | G |
|---|---|---|---|---|---|---|---|---|
| 60 | Methanesulfonic acid-quinoxalin-6-yl ester | O | 4-piperidinyl | C=O | H | 1 | 0 | 6-methyl-2H-benzo[b][1,4]thiazin-3(4H)-one |
| 61 | (Quinoxalin-6-yloxy)-acetic acid methyl ester | O | 4-piperidinyl | C=O | H | 1 | 0 | 6-methyl-2H-benzo[b][1,4]thiazin-3(4H)-one |
| 62 | 7-Difluoromethoxy-quinoxaline | O | 4-piperidinyl | C=O | H | 1 | 0 | 6-methyl-2H-benzo[b][1,4]thiazin-3(4H)-one |
| 63* | 7-Methoxy-quinoxaline | O | 4-piperidinyl | C=O | H | 1 | 0 | 6-methyl-2H-benzo[b][1,4]thiazin-3(4H)-one |
| 64* | 7-Methoxy-quinoxaline | O | 4-piperidinyl | C=O | H | 1 | 0 | 6-methyl-2H-benzo[b][1,4]thiazin-3(4H)-one |

TABLE 1-continued

Exemplified compounds

| Expl./Comp. | A | A2 | A3 | R4 | m | n | G |
|---|---|---|---|---|---|---|---|
| 65* | 7-Methoxy-quinoxaline | S | piperidine | C=O | H | 1 | 0 | 6-methyl-benzothiazin-3-one |
| 66 | 7-Methoxy-quinoxaline | O | 4-methyl-3-(hydroxymethyl)piperidine | C=O | H | 1 | 0 | 6-methyl-benzothiazin-3-one |
| 67 | 7-Methoxy-quinoxaline | S | 4-methyl-3-(hydroxymethyl)piperidine | C=O | H | 1 | 0 | 6-methyl-benzothiazin-3-one |
| 68 | 7-Methoxy-3-methyl-quinoxaline | O | piperidine | C=O | H | 1 | 0 | 6-methyl-7-chloro-benzothiazin-3-one |
| 69 | 7-Methylsulfanyl-quinoxaline | O | piperidine | C=O | H | 1 | 0 | 6-methyl-benzothiazin-3-one |

TABLE 1-continued

Exemplified compounds

| Expl./Comp. | A | A2 | A3 | R4 | m | n | G |
|---|---|---|---|---|---|---|---|
| 70 | 3-Methoxy-quinoline | piperidine | C=O | H | 1 | 0 | 3-methyl-5-(thiophen-2-yl)isoxazole |
| 71 | 2-Methoxy-quinoline | piperidine | C=O | H | 1 | 0 | 6-methyl-2H-benzo[b][1,4]thiazin-3(4H)-one |
| 72 | 7-Cyano-quinoxaline | piperidine | C=O | H | 1 | 0 | 7-chloro-6-methyl-2H-benzo[b][1,4]thiazin-3(4H)-one |
| 73 | 7-Fluoro-6-methoxy-quinoline | piperidine | CH₂ | H | 1 | 0 | 6-methyl-2H-benzo[b][1,4]thiazin-3(4H)-one |
| 74 | 7-Methoxy-quinoline-3-carboxylic acid | trans-cyclohexane | C=O | H | 1 | 0 | 6-methyl-2H-benzo[b][1,4]thiazin-3(4H)-one |

TABLE 1-continued

Exemplified compounds

| Expl./Comp. | A (R1-X6-X1-...-X2-X3-X4-X5 ring) | A | A2 | A3 | R4 | m | n | G |
|---|---|---|---|---|---|---|---|---|
| 75* | 7-Methoxy-quinoxaline | O | piperidine (4,1-linked) | CH₂ | H | 1 | 0 | 6-substituted 4H-benzo[1,4]thiazin-3-one |
| 76 | 7,8-Dimethoxy-quinoxaline | S | piperidine (4,1-linked) | C=O | H | 1 | 0 | 6-substituted 4H-benzo[1,4]thiazin-3-one |
| 77 | 4-Ethoxy-6-methoxy-[1,5]naphthyridine | O | piperidine (4,1-linked) | C=O | H | 1 | 0 | 6-substituted 4H-benzo[1,4]thiazin-3-one |
| 78 | 7-Methoxy-quinoxaline | O | 3-hydroxy-piperidine (4,1-linked) | C=O | H | 1 | 0 | 6-substituted 4H-benzo[1,4]thiazin-3-one |
| 79* | 7-Methoxy-quinoxaline | O | 3-hydroxy-piperidine (4,1-linked) | C=O | H | 1 | 0 | 6-substituted 4H-benzo[1,4]thiazin-3-one |

TABLE 1-continued

Exemplified compounds

| Expl./Comp. | A | A2 | A3 | R4 | m | n | G |
|---|---|---|---|---|---|---|---|
| 80 | 7-Methoxy-quinoxaline | O | (3-hydroxy-4-tert-butyl-1-tert-butyl-piperidinyl) | C=O | H | 1 | 0 | 6-methyl-2H-benzo[b][1,4]thiazin-3(4H)-one |
| 81 | 7-Methoxy-quinoxaline | O | (3-hydroxy-4-tert-butyl-1-tert-butyl-piperidinyl, other stereochem) | C=O | H | 1 | 0 | 6-methyl-2H-benzo[b][1,4]thiazin-3(4H)-one |
| 82 | 7-(2-Methoxy-ethoxy)-quinoxaline | O | piperidin-4-yl | C=O | H | 1 | 0 | 6-methyl-2H-benzo[b][1,4]thiazin-3(4H)-one |
| 83 | Isoxazole-5-carboxylic acid-quinoxalin-6-yl ester | O | piperidin-4-yl | C=O | H | 1 | 0 | 6-methyl-2H-benzo[b][1,4]thiazin-3(4H)-one |
| 84 | Methoxy-acetic acid-quinoxalin-6-yl ester | O | piperidin-4-yl | C=O | H | 1 | 0 | 6-methyl-2H-benzo[b][1,4]thiazin-3(4H)-one |

TABLE 1-continued
Exemplified compounds
| Expl./Comp. | A | A2 | A3 | R4 | m | n | G |
|---|---|---|---|---|---|---|---|
| 85 | 7-[2-(4-Difluoromethoxy-phenyl)-2-oxo-ethoxy]-quinoxaline | O | 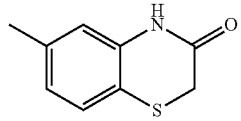 | C=O | H | 1 | 0 | 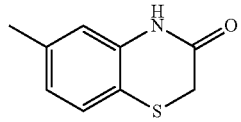 |
| 86 | (Quinoxalin-6-yloxy)-acetic acid tert-butyl ester | O | 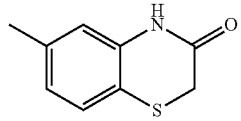 | C=O | H | 1 | 0 | 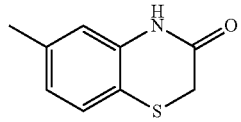 |
| 87 | 7-(2-Oxo-butoxy)-quinoxaline | O | 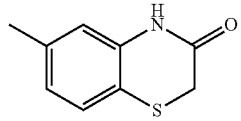 | C=O | H | 1 | 0 | 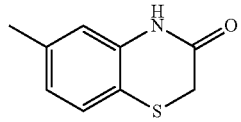 |
| 88 | 7-Isopropoxy-quinoxaline | O | 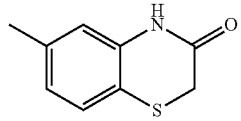 | C=O | H | 1 | 0 | 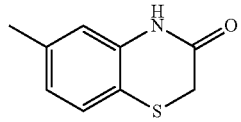 |
| 89 | 7-(2-Phenoxy-ethoxy)-quinoxaline | O | 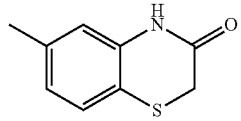 | C=O | H | 1 | 0 | 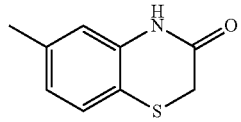 |

TABLE 1-continued

Exemplified compounds

| Expl./Comp. | A | A2 | A3 | R4 | m | n | G |
|---|---|---|---|---|---|---|---|
| 90 | 7-(2-[1,3]Dioxan-2-yl-ethoxy)-quinoxaline | O | piperidine | C=O | H | 1 | 0 | 6-methyl-2H-benzo[b][1,4]thiazin-3(4H)-one |
| 91 | 7-(3-Hydroxy-propoxy)-quinoxaline | O | piperidine | C=O | H | 1 | 0 | 6-methyl-2H-benzo[b][1,4]thiazin-3(4H)-one |
| 92 | 7-(3-Cyano-propoxy)-quinoxaline | O | piperidine | C=O | H | 1 | 0 | 6-methyl-2H-benzo[b][1,4]thiazin-3(4H)-one |
| 93 | 7-Propoxy-quinoxaline | O | piperidine | C=O | H | 1 | 0 | 6-methyl-2H-benzo[b][1,4]thiazin-3(4H)-one |
| 94* | 7-Methoxy-quinoxaline | O | piperidine | C=O | H | 1 | 0 | 6-methyl-2H-benzo[b][1,4]thiazin-3(4H)-one |

TABLE 1-continued

Exemplified compounds

| Expl./Comp. | A | A2 | A3 | R4 | m | n | G |
|---|---|---|---|---|---|---|---|
| 95* | 7-Methoxy-quinoxaline | piperidine (N-linked, 4-linked) | C=O | H | 1 | 0 | 6-methyl-2H-benzo[b][1,4]thiazin-3(4H)-one |
| 96* | 7-Methoxy-quinoxaline | piperidine (N-linked, 4-linked) | CH₂ | H | 1 | 0 | 6-methyl-2H-benzo[b][1,4]thiazin-3(4H)-one |
| 97* | 7-Methoxy-quinoxaline | piperidine (4-linked, N-linked) | C=O | H | 1 | 0 | 6-methyl-2H-benzo[b][1,4]thiazin-3(4H)-one |
| 98 | 7-Methoxy-quinoxaline | 3-methyl-1-benzyl-piperidine (2,5-linked) | CH₂ | H | 1 | 0 | 6-methyl-2H-benzo[b][1,4]thiazin-3(4H)-one |
| 99 | 7-Methoxy-quinoxaline | 4-methyl-3-(hydroxymethyl)-piperidine (N,4-linked) | C=O | H | 1 | 0 | 6-methyl-2H-benzo[b][1,4]thiazin-3(4H)-one |

TABLE 1-continued

Exemplified compounds

| Expl./Comp. | R1-X6-X1 / X5-X4-X3-X2 ring | A | A2 | A3 | R4 | m | n | G |
|---|---|---|---|---|---|---|---|---|
| 100 | 8-Hydroxy-quinoline | CO$_2$ | trans-cyclohexyl | C=O | H | 0 | 0 | 6-methyl-4H-benzo[1,4]thiazin-3-one |
| 101 | 2-Chloro-6-methoxy-quinoline | CO$_2$ | trans-cyclohexyl | C=O | H | 0 | 0 | 6-methyl-4H-benzo[1,4]thiazin-3-one |
| 102 | 6-Methoxy-[1,5]naphthyridine | S | piperidin-4-yl | CH$_2$ | H | 1 | 0 | 7-chloro-6-methyl-pyrido-thiazin-3-one |
| 103 | 6-Methoxy-[1,5]naphthyridine | S | piperidin-4-yl | C=O | H | 1 | 0 | 6-methyl-pyrido[1,4]oxazin-3-one |
| 104 | 7-Methoxy-quinoxaline | S | piperidin-3-yl | C=O | H | 1 | 1 | 6-methyl-4H-benzo[1,4]thiazin-3-one |

TABLE 1-continued

Exemplified compounds

| Expl./Comp. | A | A2 | A3 | R4 | m | n | G |
|---|---|---|---|---|---|---|---|
| 105 | 7-Methoxy-quinoxaline | 4-methyl-3-(hydroxymethyl)piperidine | CH₂ | H | 1 | 0 | 6-methyl-2H-benzo[b][1,4]thiazin-3(4H)-one |
| 106* | 7-Methoxy-quinoxaline | piperidin-4-yl | C=O | H | 1 | 0 | 6-methyl-2H-benzo[b][1,4]thiazin-3(4H)-one |
| 107* | 7-Methoxy-quinoxaline | piperidin-4-yl | C=O | H | 1 | 0 | 6-methyl-2H-benzo[b][1,4]thiazin-3(4H)-one |
| 108* | 7-Methoxy-quinoxaline | piperidin-4-yl | C=O | H | 1 | 0 | 6-methyl-2H-benzo[b][1,4]thiazin-3(4H)-one |
| 109* | 7-Methoxy-quinoxaline | piperidin-4-yl | C=O | H | 1 | 0 | 6-methyl-2H-benzo[b][1,4]thiazin-3(4H)-one |

TABLE 1-continued

Exemplified compounds

| Expl./Comp. | (ring) | A | A2 | A3 | R4 | m | n | G |
|---|---|---|---|---|---|---|---|---|
| 110 | 7-Methoxy-quinoxaline | O | piperidine (N-linked, 4-linked) | CH₂ | H | 1 | 0 | 4-tert-butylphenyl |
| 111 | 7-Methoxy-quinoxaline | O | piperidine (N-linked, 4-linked) | C=O | H | 1 | 0 | 6-methyl-7-trifluoromethyl-2H-1,4-benzothiazin-3(4H)-one |
| 112 | 7-Methoxy-quinoxaline | O | piperidine (N-linked, 4-linked) | C=O | H | 1 | 0 | 2-methylthieno[3,2-b]thiophene |
| 113 | 6-Methoxy-quinoline | CO₂ | trans-cyclohexane-1,4-diyl | CH₂ | H | 0 | 0 | 3-fluoro-4-methylphenyl (2,4-disubstituted) |
| 114 | 6-Methoxy-quinoline | CO₂ | trans-cyclohexane-1,4-diyl | CH₂ | H | 0 | 0 | 4-trifluoromethylphenyl |

TABLE 1-continued

Exemplified compounds

| Expl./Comp. | [ring structure with R1, X1-X6] | A | A2 | A3 | R4 | m | n | G |
|---|---|---|---|---|---|---|---|---|
| 115 | 6-Methoxy-quinoline | $CO_2$ | [cyclohexyl] | $CH_2$ | H | 0 | 0 | [3-F, 4-$CF_3$ phenyl] |
| 116 | 6-Methoxy-quinoline | $CO_2$ | [cyclohexyl] | —$CH_2$—CH=CH— | H | 0 | 0 | [phenyl] |
| 117 | 6-Methoxy-quinoline | $CO_2$ | [cyclohexyl] | $CH_2$ | H | 0 | 0 | [p-phenylene] |
| 118 | 6-Methoxy-quinoline | $CO_2$ | [cyclohexyl] | $CH_2$ | H | 0 | 0 | [benzothiophen-2-yl] |
| 119 | 6-Methoxy-quinoline | $CO_2$ | [cyclohexyl] | $CH_2$ | H | 0 | 0 | [naphthalen-2-yl] |

TABLE 1-continued

Exemplified compounds

| Expl./Comp. | [R1-X ring] | A | A2 | A3 | R4 | m | n | G |
|---|---|---|---|---|---|---|---|---|
| 120 | 6-Methoxy-quinoline | $CO_2$ | trans-cyclohexyl | —$(CH_2)_3$— | H | 0 | 0 | phenyl |
| 121 | 6-Methoxy-quinoline | $CO_2$ | trans-cyclohexyl | $CH_2$ | H | 0 | 0 | benzofuran-6-yl |
| 122 | 7-Methoxy-quinoxaline | S | piperidin-4-yl | C=O | H | 1 | 0 | 6-methyl-3,4-dihydro-2H-benzo[1,4]thiazine |
| 123 | 7-Methoxy-quinoxaline | O | piperidin-4-yl | $CH_2$ | H | 1 | 0 | benzo[1,3]dioxol-5-yl |

*For Example 14 the group A1 has the formula: —O—CH($CF_3$)—$CH_2$—;
For Example 63 the group A1 has the formula: —O—CH($CH_2OCH_3$)—$CH_2$—;
For Example 64 the group A1 has the formula: —O—CH($CH_2OCH_2CH_2$ $OCH_3$)—$CH_2$—;
For Example 65 the group A1 has the formula: —S—CH($CH_2$-morpholino)-$CH_2$—;
For Example 75 the group A1 has the formula: —O—CH(cyclopropyl)-$CH_2$—;
For Example 94 the group A1 has the formula: —O—CH($CH_3$)—$CH_2$—;
For Example 95 the group A1 has the formula: —O—CH($CH_2F$)—$CH_2$—;
For Example 96 the group A1 has the formula: —O—CH(CH=$CH_2$)—$CH_2$—;
For Example 97 the group A1 has the formula: —O—CH($C_2H_5$)—$CH_2$—;
For Example 106 the group A1 has the formula: —O—CH($CH_2OC_2H_5$)—$CH_2$—;
For Example 107 the group A1 has the formula: —O—CH($CH_2OCH_2$—$C_6H_5$)—$CH_2$—
For Example 108 the group A1 has the formula: —O—CH($CH_2OCH_2CH_2$ $OCH_2CF_3$)—$CH_2$—;
For Example 109 the group A1 has the formula: —O—CH($CH_2OCH_2CF_3$)—$CH_2$—.

The numbers of the compounds of formula I used in the leftmost column of Table 1 is used in the whole application text for identifying the respective compounds, e.g. in Table 2 referring to the results in the tests for biological activity.

Example 1

3-oxo-3,4-dihydro-2H-benzo[1,4]thiazine-6-carboxylic acid {1-[2-(7-methoxy-quinoxalin-2-yloxy)-ethyl]-piperidin-4-yl}-amide Preparation of [1-(2-hydroxy-ethyl)-piperidin-4-yl]-carbamic acid tert-butyl ester 2-Bromo-ethanol (2.38 mL, 33.5 mmol, 1.0 eq) is added at room temperature to a stirred solution of piperidin-4-yl-carbamic acid tert-butyl ester (7.0 g, 33.5 mmol, 1.0 eq) in N,N-dimethylformamide (300 mL), followed by potassium carbonate (4.64 g, 33.5 mmol, 1.0 eq). After 6 hours stirring at room temperature, solvent is evaporated and the residue is extracted with ethyl acetate (3×40 mL) and water (40 mL). pH of the aqueous layer is neutralized with a 0.1 N hydrochloric acid aqueous solution. The combined organic layers are dried over sodium sulfate, filtered and concentrated to afford [1-(2-hydroxy-ethyl)-piperidin-4-yl]-carbamic acid tert-butyl ester as an off-white oil (7.96 g, 97% yield).
$^1$H-NMR (400 MHz, DMSO-d$_6$) δ ppm: 6.75 (d, J=7.6 Hz, 1H), 4.40 (br, 1H), 3.47 (t, J=6.2 Hz, 2H), 3.32 (br, 1H), 3.17 (br, 1H), 2.80 (m, 2H), 2.36 (t, J=6.2 Hz, 2H), 1.97 (m, 2H), 1.68 (m, 2H), 1.37 (m, 10H).
MS m/z (+ESI): 245.3 [M+H]$^+$.

Preparation of {1-[2-(7-methoxy-quinoxalin-2-yloxy)-ethyl]-piperidin-4-yl}-carbamic acid tert-butyl ester Sodium hydride (55% purity, 62 mg, 1.48 mmol, 1.5 eq) is added at room temperature to a stirred solution of 2-chloro-7-methoxy-quinoxaline (200 mg, 0.99 mmol, 1.0 eq) in N,N-dimethylformamide (10 mL), followed by [1-(2-hydroxy-ethyl)-piperidin-4-yl]-carbamic acid tert-butyl ester (268 mg, 0.99 mmol, 1.0 eq). After 4 hours stirring at room temperature, solvent is evaporated, and the residue is extracted with dichloromethane (3×20 mL) and water (20 mL). The combined organic layers are dried over sodium sulfate, filtered and concentrated to give a residue that is purified by column chromatography (silica gel, eluent: cyclohexane:ethyl acetate:methanol, 1:1:0 to 0:9:1, v/v/v) to afford {1-[2-(7-methoxy-quinoxalin-2-yloxy)-ethyl]-piperidin-4-yl}-carbamic acid tert-butyl ester as an orange solid (210 mg, 52% yield).
$^1$H-NMR (400 MHz, DMSO-d$_6$) δ ppm: 8.41 (s, 1H), 7.88 (d, J=9.0 Hz, 1H), 7.20-7.28 (m, 2H), 6.75 (br, 1H), 4.52 (t, J=5.8 Hz, 2H), 3.92 (s, 3H), 3.25 (m, 1H), 2.92 (m, 2H), 2.73 (m, 2H), 2.10 (m, 2H), 1.68 (m, 2H), 1.37 (m, 11H).
MS m/z (+ESI): 403.2 [M+H]$^+$.

Preparation of 1-[2-(7-methoxy-quinoxalin-2-yloxy)-ethyl]-piperidin-4-ylamine

Trifluoroacetic acid (580 µL, 7.52 mmol, 15.0 eq) is added at 0° C. to a stirred solution of {1-[2-(7-methoxy-quinoxalin-2-yloxy)-ethyl]-piperidin-4-yl}-carbamic acid tert-butyl ester (206 mg, 0.50 mmol, 1.0 eq) in dichloromethane (20 mL). After 15 hours stirring at room temperature, the reaction mixture is extracted with dichloromethane (3×20 mL) and water (20 mL) and the pH is adjusted to 12 by the addition of a 1N sodium hydroxide aqueous solution. The combined organic layers are dried over sodium sulfate, filtered and concentrated to afford 1-[2-(7-methoxy-quinoxalin-2-yloxy)-ethyl]-piperidin-4-ylamine as an orange oil (155 mg, 99.5% yield).
$^1$H-NMR (400 MHz, DMSO-d$_6$) δ ppm: 8.41 (s, 1H), 7.88 (d, J=9.0 Hz, 1H), 7.20-7.28 (m, 2H), 4.52 (t, J=5.9 Hz, 2H), 3.93 (s, 3H), 2.88 (m, 2H), 2.73 (t, J=5.9 Hz, 2H), 2.08 (td, J=2.3, 11.5, 2H), 1.68 (m, 2H), 1.45 (br, 1H), 1.22 (m, 2H).
MS m/z (+ESI): 303.3 [M+H]$^+$.

Preparation of 3-oxo-3,4-dihydro-2H-benzo[1,4]thiazine-6-carboxylic acid {1-[2-(7-methoxy-quinoxalin-2-yloxy)-ethyl]-piperidin-4-yl}-amide 3-Oxo-3,4-dihydro-2H-benzo[1,4]thiazine-6-carboxylic acid (60 mg, 0.26 mmol, 1.0 eq) is added at room temperature to a stirred solution of 1-[2-(7-methoxy-quinoxalin-2-yloxy)-ethyl]-piperidin-4-ylamine (80 mg, 0.26 mmol, 1.0 eq) in N,N-dimethylformamide (5 mL), followed by 1-hydroxybenzotriazole (38 mg, 0.29 mmol, 1.1 eq), N-(3-dimethylaminopropyl)-N'-ethylcarbodiimide hydrochloride (57 mg, 0.30 mmol, 1.15 eq) and N,N-diisopropylethylamine (100 µL, 0.58 mmol, 2.25 eq). After 15 hours stirring at room temperature, solvent is evaporated and the residue is extracted with dichloromethane (3×10 mL) and water (10 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid {1-[2-(7-methoxy-quinoxalin-2-yloxy)-ethyl]-piperidin-4-yl}-amide as an off-white solid (18 mg, 13% yield).
$^1$H-NMR (400 MHz, DMSO-d$_6$) δ ppm: 10.65 (s, 1H), 8.42 (s, 1H), 8.22 (d, J=7.8 Hz, 1H), 7.89 (d, J=9.0 Hz, 1H), 7.38-7.46 (m, 3H), 7.22-7.28 (m, 2H), 4.56 (t, J=5.8 Hz, 2H), 3.92 (s, 3H), 3.75 (m, 1H), 3.50 (s, 2H), 3.00 (m, 2H), 2.81 (t, J=5.8 Hz, 2H), 2.18 (m, 2H), 1.79 (m, 2H), 1.55 (m, 2H).
MS m/z (+ESI): 494.4 [M+H]$^+$.

Example 2

3-oxo-3,4-dihydro-2H-benzo[1,4]thiazine-6-carboxylic acid {trans-4-[2-(6-methoxy-[1,5]naphthyridin-3-yloxy)-ethyl]-cyclohexyl}-amide Preparation of 2-[(6-methoxy-pyridin-3-ylamino)-methylene]-malonic acid diethyl ester A solution of 3-amino-6-methoxy-pyridine (200.0 g, 1611.05 mmol, 1.0 eq) and 2-ethoxymethylene-malonic acid diethyl ester (348.4 g, 1611.05 mmol, 1.0 eq) in toluene (650 mL) is heated to reflux and the ethanol formed is removed by azeotropic distillation. After 2.5 hours at 115° C., the reaction mixture is cooled to room temperature, the solvent is removed and the resulting solid is washed with 500 mL of hexane then dried under vacuum to afford 2-[(6-methoxy-pyridin-3-ylamino)-methylene]-malonic acid diethyl ester as a red solid (434.0 g, 90% yield).
$^1$H-NMR (400 MHz, CDCl$_3$) δ ppm: 10.92 (d, J=13.2 Hz, 1H), 8.36 (d, J=13.2 Hz, 1H), 8.02 (d, J=2.8 Hz, 1H), 7.42 (dd, J=2.8, 8.8 Hz, 1H), 6.77 (d, J=8.8 Hz, 1H), 4.33-4.20 (m, 4H), 3.93 (s, 3H), 1.40-1.29 (m, 6H).
MS m/z (+ESI): 295.1 [M+H]$^+$.

Preparation of 6-methoxy-4-oxo-1,4-dihydro-[1,5] naphthyridine-3-carboxylic acid ethyl ester A solution of 2-[(6-methoxy-pyridin-3-ylamino)-methylene]-malonic acid diethyl ester (260.0 g, 1.365 mol, 1.0 eq) in diphenyl ether (500 mL) is heated to reflux. While the ethanol formed is removed by azeotropic distillation the reflux temperature reached 245° C. The reaction mixture is kept at 245° C. for 3 hours, then it is cooled to 28° C., a brown solid precipitated and is collected by filtration and washed with hexane (500 mL). The solid is dried under vacuum to afford 6-methoxy-4-oxo-1,4-dihydro-[1,5]naphthyridine-3-carboxylic acid ethyl ester as a brown powder (74.2 g, 32% yield).

$^1$H-NMR (400 MHz, DMSO-d6) δ ppm: 12.28 (s, 1H), 8.47 (s, 1H), 7.98 (d, J=9.2 Hz, 1H), 7.18 (d, 1H, J=9.2 Hz), 4.20 (d, J=7.2 Hz, 2H). 3.93 (s, 3H), 1.27 (t, J=7.2 Hz, 3H).

MS m/z (+ESI): 249.1 [M+H]$^+$.

Preparation of 4-chloro-6-methoxy-[1,5]naphthyridine-3-carboxylic acid ethyl ester A solution of 6-methoxy-4-oxo-1,4-dihydro-[1,5]naphthyridine-3-carboxylic acid ethyl ester (110.0 g, 407.67 mmol, 1.0 eq) in phosphorus oxychloride (650 mL) is refluxed for 4 hours. Then the reaction mixture is cooled to room temperature and the solvent is evaporated. The residue is poured into ice water and the resulting mixture is basified with 25% ammonium hydroxide to pH=8-9 and extracted with ethyl acetate (3×500 mL). The combined organic layers are dried over sodium sulfate, filtered and evaporated to give a brown solid as crude product, which is then purified by column chromatography (silica gel, eluent: ethyl acetate:petroleum ether, 1:4, v/v) to afford 4-chloro-6-methoxy-[1,5]naphthyridine-3-carboxylic acid ethyl ester as a light yellow solid (78 g, 62% yield).

$^1$H-NMR (400 MHz, CDCl$_3$) δ ppm: 9.05 (s, 1H), 8.27 (d, J=9.2 Hz, 1H), 7.25 (d, J=9.2 Hz, 1H), 4.52 (q, J=6.8 Hz, 2H), 4.17 (s, 3H), 1.47 (t, J=6.8 Hz, 3H).

MS m/z (+ESI): 267.1 [M+H]$^+$.

Preparation of 6-methoxy-[1,5]naphthyridine-3-carboxylic acid ethyl ester

A mixture of 4-chloro-6-methoxy-[1,5]naphthyridine-3-carboxylic acid ethyl ester (75 g, 241.86 mmol, 1.0 eq), triethylamine (75 mL, 538.08 mmol, 2.22 eq), and 10% palladium on activated carbon (8.2 g) in ethanol (1350 mL) is stirred under hydrogen flow at room temperature for 6 hours. The catalyst is then removed by filtration and the solution is evaporated to dryness to give a yellow solid as crude product, which is purified by column chromatography (silica gel, eluent: petroleum ether:ethyl acetate, 5:1, v/v) to afford 6-methoxy-[1,5]naphthyridine-3-carboxylic acid ethyl ester as a light yellow powder (46.2 g, 77% yield).

$^1$H-NMR (400 MHz, CDCl$_3$) δ ppm: 9.32 (d, J=2.0 Hz, 1H), 8.77 (d, J=2.0 Hz, 1H), 8.25 (d, J=10.0 Hz, 1H), 7.22 (d, J=10.0 Hz, 1H), 4.47 (q, J=6.8 Hz, 2H), 4.10 (s, 3H), 1.46 (t, J=6.8 Hz, 3H).

MS m/z (+ESI): 233.1 [M+H]$^+$.

Preparation of 6-methoxy-[1,5]naphthyridine-3-carboxylic acid

A mixture of 6-methoxy-[1,5]naphthyridine-3-carboxylic acid ethyl ester (32.0 g, 74.45 mmol, 1.0 eq) and sodium hydroxide (10.12 g, 137.51 mmol, 1.85 eq) in ethanol (110 mL) is refluxed for 3 hours. The solvent is evaporated and the residue is dissolved in water, washed with ethyl acetate, then acidified with 3N hydrochloric acid aqueous solution to pH=3-4. The precipitate is collected by filtration, dried under 50° C. overnight to afford 6-methoxy-[1,5]naphthyridine-3-carboxylic acid as a white solid (24.5 g, 82% yield).

$^1$H-NMR (400 MHz, DMSO-d$_6$) δ ppm: 13.60 (br, 1H), 9.19 (t, J=2.0 Hz, 1H), 8.55 (d, J=2.0 Hz, 1H), 8.33 (d, J=8.8 Hz, 1H), 7.38 (d, J=8.8 Hz, 1H), 4.03 (s, 3H).

MS m/z (+ESI): 205.2 [M+H]$^+$.

Preparation of (6-methoxy-[1,5]naphthyridine-3-yl)-carbamic acid tert-butyl ester A mixture of 6-methoxy-[1,5]naphthyridine-3-carboxylic acid (24.5 g, 120 mmol, 1.0 eq), triethylamine (50.2 mL, 360 mmol, 3.0 eq) and tert-butanol (292 mL, 3.54 mol, 32 eq) in dimethylformamide (338 mL) is added dropwise to diphenyl phosphoryl azide (49.5 g, 180 mmol. 1.5 eq) to form a yellow clear solution. The mixture is stirred at 70° C. for 40 minutes then warmed to 100° C. for 3 hours. The mixture is cooled to room temperature and concentrated to dryness. The residue is purified by column chromatography (silica gel, eluent: dichloromethane:petroleum ether:ethyl acetate, 25:25:2, v/v/v) to afford (6-methoxy-[1,5]naphthyridine-3-yl)-carbamic acid tert-butyl ester as a yellow solid (23.15 g, 69% yield).

$^1$H-NMR (400 MHz, DMSO-d$_6$) δ ppm: 9.96 (s, 1H), 8.77 (d, J=2.4 Hz, 1H), 8.29 (d, J=2.4 Hz, 1H), 8.13 (d, J=9.6 Hz, 1H), 7.05 (d, J=9.6 Hz, 1H), 3.97 (s, 3H), 1.50 (s, 9H).

MS m/z (+ESI): 276.3 [M+H]$^+$.

Preparation of 3-amino-6-methoxy-[1,5]naphthyridine

Trifluoroacetic acid (101 mL, 1.32 mol, 20.85 eq) is added to a stirred solution of (6-methoxy-[1,5]naphthyridine-3-yl)-carbamic acid tert-butyl ester (18.2 g, 66.11 mmol, 1.0 eq) in dichloromethane (500 mL). After 19 hours stirring at room temperature, the solution is evaporated to dryness, 6N sodium hydroxide aqueous solution is added to adjust pH to 9~10 and a lot of solid precipitated. The mixture is extracted with dichloromethane (200 mL) and the residue is extracted with ethyl acetate (3×250 mL). Evaporation of the dichloromethane phase gives 2.44 g of product with 83% purity, which is then purified by column chromatography (silica gel, eluent: dichloromethane:petroleum ether:ethyl acetate, 25:25:2, v/v/v) to afford 6-methoxy-[1,5]naphthyridin-3-ylamino as a light yellow solid (1.95 g with 98% purity). Evaporation of the ethyl acetate phase yields additional 9.88 g of light yellow product with 99% purity. Total: 11.83 g (98% yield).

$^1$H-NMR (400 MHz, DMSO-d$_6$) δ ppm: 8.25 (d, J=2.0 Hz, 1H), 7.99 (d, J=8.8 Hz, 1H), 7.02 (d, J=2.0 Hz, 1H), 6.76 (d, J=8.8 Hz, 1H), 5.90 (s, 2H), 3.91 (s, 3H).

MS m/z (+ESI): 176.1 [M+H]$^+$.

Preparation of 6-methoxy-[1,5]naphthyridin-3-ol 6-methoxy-[1,5]naphthyridin-3-ylamino (13.6 g, 77.63 mmol, 1.0 eq) is added to a solution of sulfuric acid (20.7 mL, 388 mmol, 5.0 eq) in water (177 mL) at 0~4° C. Then a solution of sodium nitrite (5.89 g, 85.39 mmol, 1.1 eq) in water (136 mL) is added to this solution. The mixture is stirred at −5° C.-0° C. for 2 hours, then it is allowed to come at room temperature and stir for 2 hours. After being adjusted to pH=7, the mixture is extracted with ethyl acetate (3×250 mL). The organic layers are combined, dried over sodium sulfate and concentrated to yield the crude product, which is purified by column chromatography (silica gel, eluent: petroleum ether:ethyl acetate, 8:1 to 1:1, v/v) to afford 6-methoxy-[1,5]naphthyridin-3-ol as a yellow solid (9.7 g, 65% yield).

$^1$H-NMR (400 MHz, DMSO-d$_6$), δ ppm: 10.58 (br, 1H), 8.42 (d, J=2.8 Hz, 1H), 8.11 (d, J=8.8 Hz, 1H), 7.33 (d, J=2.8 Hz, 1H), 6.97 (d, J=8.8 Hz, 1H), 3.95 (s, 3H).

MS m/z (+ESI): 177.1 [M+H]$^+$.

Preparation of [trans-4-(2-hydroxy-ethyl)-cyclohexyl]-carbamic acid tert-butyl ester A solution of borane dimethyl sulphide complex in tetrahydrofuran (11.7 mL, 23.32 mmol, 3.0 eq) is added dropwise within 10 minutes at −5° C. to a stirred solution of (4-tert-butoxycarbonylamino-cyclohexyl)-acetic acid (2.0 g, 7.77 mmol, 1.0 eq) in tetrahydrofuran (50 mL). The reaction mixture is stirred at −5° C. for 20 minutes then at room temperature for 3 hours. Methanol (10 mL) is cautiously added to the reaction mixture that is then evaporated and repeatedly treated with methanol and concentrated to dryness to afford [trans-4-(2-hydroxy-ethyl)-cyclohexyl]-carbamic acid tert-butyl ester as a white solid (1.89 g, 99.5% yield).

$^1$H-NMR (400 MHz, DMSO-d$_6$), δ ppm: 6.62 (d, J=8.4 Hz, 1H), 4.26 (t, J=5.2 Hz, 1H), 3.35-3.41 (m, 2H), 3.12-3.10 (m, 1H), 1.64-1.73 (m, 4H), 1.35 (s, 9H), 1.20-1.30 (m, 3H), 1.04-1.13 (m, 2H), 0.83-0.91 (m, 2H).

Preparation of {trans-4-[2-(6-methoxy-[1,5]naphthyridin-3-yloxy)-ethyl]-cyclohexyl}-carbamic acid tert-butyl ester Diethyl azodicarboxylate (3.96 g, 22.72 mmol, 3.0 eq) is added at room temperature to a stirred solution of [trans-4-(2-hydroxy-ethyl)-cyclohexyl]-carbamic acid tert-butyl ester (1.84 g, 7.57 mmol, 1.0 eq), 6-methoxy-[1,5]naphthyridin-3-ol (1.80 g, 10.22 mmol, 1.35 eq) and triphenylphosphine (5.96 g, 22.72 mmol, 3.0 eq) in tetrahydrofuran (70 mL). After 14 hours stirring at 30° C., tetrahydrofuran is evaporated and the resulting crude product is purified by column chromatography (silica gel, eluent: petroleum ether:ethyl acetate, 6:1, v/v) to afford {trans-4-[2-(6-methoxy-[1,5] naphthyridin-3-yloxy)-ethyl]-cyclohexyl}-carbamic acid tert-butyl ester as an off-white solid (1.65 g, 53.5% yield).

$^1$H-NMR (400 MHz, DMSO-d$_6$) δ ppm: 8.49 (d, J=2.0 Hz, 1H), 8.16 (d, J=8.8 Hz, 1H), 7.57 (d, J=2.0 Hz, 1H), 7.54 (d, J=8.8 Hz, 1H), 6.67 (d, J=8.0 Hz, 1H), 4.18 (t, J=6.4 Hz, 2H), 3.98 (s, 3H), 3.26 (s, 1H), 1.76-1.79 (m, 4H), 1.65-1.70 (m, 2H), 1.35 (s, 10H), 0.98-1.14 (m, 4H).

MS m/z (+ESI): 402.2 [M+H]$^+$.

Preparation of trans-4-[2-(6-methoxy-[1,5]naphthyridin-3-yloxy)-ethyl]-cyclohexylamine Trifluoroacetic acid (6.33 mL, 82.2 mmol, 20 eq) is added at room temperature to a stirred solution of {trans-4-[2-(6-methoxy-[1,5]naphthyridin-3-yloxy)-ethyl]-cyclohexyl}-carbamic acid tert-butyl ester (1.65 g, 4.11 mmol, 1.0 eq) in dichloromethane (100 mL). After 2 hours stirring at room temperature, the reaction mixture is partitioned between saturated sodium hydrogen carbonate aqueous solution and dichloromethane and the pH value is about 10. The combined organic layers are dried over sodium sulfate and concentrated to afford trans-4-[2-(6-methoxy-[1,5]naphthyridin-3-yloxy)-ethyl]-cyclohexylamine as a yellow solid (1.24 g, 95% yield).

$^1$H-NMR (400 MHz, DMSO-d$_6$) δ ppm: 8.49 (d, J=2.4 Hz, 1H), 8.16 (d, J=8.8 Hz, 1H), 7.57 (d, J=2.4 Hz, 1H), 7.04 (d, J=8.8 Hz, 1H), 4.18 (t, J=6.4 Hz, 2H), 3.98 (s, 3H), 2.48 (s, 1H), 1.69-1.75 (m, 4H), 1.64-1.67 (m, 2H), 1.41 (s, 1H), 0.95-1.00 (m, 4H).

MS m/z (+ESI): 302.3 [M+H]$^+$.

Preparation of (3-oxo-3,4-dihydro-2H-benzo[1,4]thiazine-6-carboxylic acid {trans-4-[2-(6-methoxy-[1,5]naphthyridin-3-yloxy)-ethyl]-cyclohexyl})-amide 3-Oxo-3,4-dihydro-2H-benzo[1,4]thiazine-6-carboxylic acid (59 mg, 0.25 mmol, 1.0 eq) is added at room temperature to a stirred solution of trans-4-[2-(6-methoxy-[1,5]naphthyridin-3-yloxy)-ethyl]-cyclohexylamine (80 mg, 0.25 mmol, 1.0 eq) in N,N-dimethylformamide (5 mL), followed by 1-hydroxybenzotriazole (37 mg, 0.28 mmol, 1.1 eq), N-(3-dimethylaminopropyl)-N'-ethylcarbodiimide hydrochloride (56 mg, 0.29 mmol, 1.15 eq) and N,N-diisopropylethylamine (97 μL, 0.57 mmol, 2.25 eq). After 15 hours stirring at room temperature, solvent is evaporated and the residue is extracted with dichloromethane (3×10 mL) and water (10 mL). The combined organic layers are dried over sodium sulfate, filtered and concentrated to give a crude product that is purified by preparative HPLC to afford (3-oxo-3,4-dihydro-2H-benzo[1,4]thiazine-6-carboxylic acid {trans-4-[2-(6-methoxy-[1,5]naphthyridin-3-yloxy)-ethyl]-cyclohexyl})-amide as a white lyophilizated powder (36 mg, 27% yield).

$^1$H-NMR (400 MHz, DMSO-d$_6$) δ ppm: 10.64 (s, 1H), 8.53 (d, J=2.8 Hz, 1H), 8.19 (dd, J=0.7, 9.0 Hz, 2H), 7.62 (dd, J=0.5, 2.5 Hz, 1H), 7.37-7.46 (m, 3H), 7.07 (d, J=9.0 Hz, 1H), 4.24 (t, J=6.6 Hz, 2H), 4.00 (s, 3H), 3.70-3.80 (m, 1H), 3.50 (s, 2H), 1.80-1.90 (m, 4H), 1.70-1.80 (m, 2H), 1.45-1.55 (m, 1H), 1.30-1.40 (m, 2H), 1.05-1.18 (m, 2H).

MS m/z (+ESI): 493.4 [M+H]$^+$.

Example 3

3-oxo-3,4-dihydro-2H-pyrido[3,2-b][1,4]oxazine-6-carboxylic acid {trans-4-[2-(6-methoxy-[1,5]naphthyridin-3-yloxy)-ethyl]-cyclohexyl}-amide The title compound is prepared as a white lyophilizated powder (19 mg, 15% yield) following Scheme 1 and in analogy to Example 2 using 3-oxo-3,4-dihydro-2H-pyrido[3,2-b][1,4]oxazine-6-carboxylic acid (49 mg, 0.25 mmol 1.0 eq) and trans-4-[2-(6-methoxy-[1,5]naphthyridin-3-yloxy)-ethyl]-cyclohexylamine (80 mg, 0.25 mmol, 1.0 eq) as starting materials.

$^1$H-NMR (400 MHz, DMSO-d$_6$) δ ppm: 11.35 (br, 1H), 8.53 (d, J=2.8 Hz, 1H), 8.19 (dd, J=0.7, 9.0 Hz, 1H), 7.73 (d, J=8.2 Hz, 1H), 7.61 (m, 2H), 7.46 (d, J=8.2 Hz, 1H), 7.07 (d, J=9.0 Hz, 1H), 4.73 (s, 2H), 4.24 (t, J=6.6 Hz, 2H), 4.00 (s, 3H), 3.68-3.78 (m, 1H), 1.85-1.95 (m, 4H), 1.70-1.80 (m, 2H), 1.48-1.60 (m, 1H), 1.22-1.38 (m, 2H), 1.10-1.22 (m, 2H).

MS m/z (+ESI): 478.4 [M+H]$^+$.

Example 4

3-oxo-3,4-dihydro-2H-benzo[1,4]thiazine-6-carboxylic acid {trans-4-[2-(7-methoxy-quinoxalin-2-yloxy)-ethyl]-cyclohexyl}-amide The title compound is prepared as a white amorphous lyophilizated solid following Scheme 1 and in analogy to Example 2 using 2-hydroxy-7-methoxy-quinoxaline, [trans-4-(2-hydroxy-ethyl)-cyclohexyl]-carbamic acid tert-butyl ester and 3-oxo-3,4-dihydro-2H-benzo[1,4]thiazine-6-carboxylic acid as starting materials.

MS m/z (+ESI): 493.4 [M+H]$^+$, 515.4 [M+Na]$^+$.

Example 5

5-thiophen-2-yl-isoxazole-3-carboxylic acid {1-[2-(7-methoxy-quinoxalin-2-yloxy)-ethyl]-piperidin-4-yl}-amide The title compound is prepared as a yellow solid (39 mg, 30% yield) following Scheme 1 and in analogy to Example 1 using 5-thiophen-2-yl-isoxazole-3-carboxylic acid (51 mg, 0.26 mmol 1.0 eq) and 1-[2-(7-methoxy-quinoxalin-2-yloxy)-ethyl]-piperidin-4-ylamine (80 mg, 0.26 mmol, 1.0 eq) as starting materials.

$^1$H-NMR (400 MHz, DMSO-d$_6$) δ ppm: 8.70 (d, J=7.8 Hz, 1H), 8.42 (s, 1H), 7.75-7.90 (m, 3H), 7.20-7.35 (m, 3H), 7.17 (s, 1H), 4.55 (t, J=5.7 Hz, 2H), 3.93 (s, 3H), 3.02 (m, 2H), 2.80 (t, J=5.7 Hz, 2H), 2.48 (m, 1H), 2.15 (m, 2H), 1.78 (m, 2H), 1.60 (m, 2H).

MS m/z (+ESI): 480.3 [M+H]$^+$.

Example 6

3-oxo-3,4-dihydro-2H-benzo[1,4]oxazine-6-carboxylic acid {trans-4-[2-(6-methoxy-[1,5]naphthyridin-3-yloxy)-ethyl]-cyclohexyl}-amide The title compound is prepared as a white amorphous lyophilized solid (19 mg, 15% yield) following Scheme 1 and in analogy to Example 2 using 3-oxo-3,4-dihydro-2H-benzo[1,4]oxazine-6-carboxylic acid (50 mg, 0.25 mmol 1.0 eq) and trans-4-[2-(6-methoxy-[1,5]naphthyridin-3-yloxy)-ethyl]-cyclohexylamine (80 mg, 0.25 mmol, 1.0 eq) as starting materials.

$^1$H-NMR (400 MHz, DMSO-d$_6$) δ ppm: 10.80 (s, 1H), 8.53 (d, J=2.8 Hz, 1H), 8.19 (dd, J=0.7, 9.0 Hz, 1H), 8.11 (d, J=8.0 Hz, 1H), 7.61 (dd, J=0.5, 2.4 Hz, 1H), 7.40-7.46 (m, 2H), 7.07 (d, J=9.0 Hz, 1H), 6.97 (d, J=8.3 Hz, 1H), 4.63 (s, 2H), 4.24 (t, J=6.6 Hz, 2H), 4.00 (s, 3H), 3.68-3.80 (m, 1H), 1.80-1.90 (m, 4H), 1.70-1.80 (m, 2H), 1.45-1.55 (m, 1H), 1.25-1.45 (m, 2H), 1.05-1.20 (m, 2H).

MS m/z (+ESI): 477.4 [M+H]$^+$.

Example 7

3-oxo-3,4-dihydro-2H-benzo[1,4]thiazine-6-carboxylic acid {trans-4-[2-(7-fluoro-quinoxalin-2-yloxy)-ethyl]-cyclohexyl}-amide Preparation of (4-fluoro-2-nitro-phenylamino)-acetic acid Bromoacetic acid (5.34 g, 32.0 mmol, 0.5 eq) is added dropwise to 4-fluoro-2-nitro-phenylamine (10.0 g, 64.1 mmol, 1.0 eq) at 120° C. After the addition, the reaction mixture is stirred for 2 hours at 120° C. then xylene (10 mL) is added. The resulting reaction mixture is heated at 130° C. for 1 hour, then it is made alkaline with 25% ammonia aqueous solution. Xylene is removed under reduced pressure and the residue is diluted with water (100 mL). The mixture is filtered at 60° C. and the insoluble residue is extracted twice with 10% ammonia aqueous solution at 60° C. The aqueous layer is acidified with hydrochloric acid to pH 5, the precipitated product is filtered, washed with water and ethanol, dried under vacuum to afford (4-fluoro-2-nitro-phenylamino)-acetic acid as a red solid (2.98 g, 34% yield).

$^1$H-NMR (400 MHz, DMSO-d$_6$) δ ppm: 8.48 (t, J=4.0 Hz, 1H), 7.84 (dd, J=2.8, 9.6 Hz, 1H), 7.50 (td, J=2.8, 9.6 Hz, 1H), 6.93 (dd, J=4.4, 9.6 Hz, 1H), 3.87 (d, J=4.0 Hz, 2H).

MS m/z (+ESI): 214.9 [M+H]$^+$.

Preparation of 7-fluoro-3,4-dihydro-1H-quinoxalin-2-one

Iron powder (6.52 g, 116.8 mmol, 5.0 eq) is added at room temperature to a stirred solution of (4-fluoro-2-nitro-phenylamino)-acetic acid (6.85 g, 23.4 mmol, 1.0 eq) in glacial acetic acid (40 mL). The resulting suspension is heated at 90° C. for 3 hours, then cooled to room temperature, diluted with ethyl acetate (40 mL), and filtered through silica gel. The filtrate is concentrated to give a crude that is purified by column chromatography (silica gel, eluent: ethyl acetate:petroleum ether, 1:3, v/v) to afford 7-fluoro-3,4-dihydro-1H-quinoxalin-2-one as a brown solid (4.01 g, 72% yield).

$^1$H-NMR (400 MHz, DMSO-d$_6$) δ ppm: 10.28 (s, 1H), 6.63-6.51 (m, 3H), 5.87 (s, 1H), 3.66 (d, J=2.0 Hz, 2H).

MS m/z (+ESI): 167.1 [M+H]$^+$.

Preparation of 7-fluoro-quinoxalin-2-ol

A mixture of 7-fluoro-3,4-dihydro-1H-quinoxalin-2-one (4.00 g, 24.1 mmol, 1.0 eq), sodium hydroxide (1.93 g, 48.2 mmol, 2.0 eq) and of 3% hydrogen peroxide solution (50 mL) is refluxed for 2 hours, then it is acidified by slow addition of acetic acid. The resulting mixture is cooled to room temperature, the precipitated solid is collected by filtration, washed with ice-water, and dried under vacuum to give a crude that is purified by column chromatography (silica gel, eluent: dichloromethane:methanol, 50:1, v/v) to afford 7-fluoro-quinoxalin-2-ol as a yellow solid (2.60 g, 69% yield).

$^1$H-NMR (400 MHz, DMSO-d$_6$) δ ppm: 12.48 (s, 1H), 8.10 (s, 1H), 7.80 (dd, J=2.8, 8.8 Hz, 1H), 7.13 (td, J=2.8, 8.8 Hz, 1H), 7.00 (dd, J=2.8, 9.6 Hz, 1H).

MS m/z (+ESI): 165.1 [M+H]$^+$.

Preparation of 2-chloro-7-fluoro-quinoxaline

A mixture of 7-fluoro-quinoxalin-2-ol (2.60 g, 15.84 mmol, 1.0 eq) and phosphorus oxychloride (50 mL, 536.4 mmol, 34.0 eq) is refluxed for 1 hour, then concentrated, diluted with water (60 mL), basified to pH 7 by adding saturated sodium hydrogen carbonate aqueous solution, and extracted with ethyl acetate (3×100 mL). The combined organic layers are dried over sodium sulfate, filtered and concentrated to give a crude that is purified by column chromatography (silica gel, eluent: ethyl acetate:petroleum ether, 1:20, v/v) to afford 2-chloro-7-fluoro-quinoxaline as a white solid (2.50 g, 84% yield).

$^1$H-NMR (400 MHz, DMSO-d$_6$) δ ppm: 8.98 (s, 1H), 8.22 (dd, J=2.0, 8.8 Hz, 1H), 7.81-7.89 (m, 2H).

MS m/z (+EI): 183.0 [M+H]$^+$.

Preparation of 3-oxo-3,4-dihydro-2H-benzo[1,4]thiazine-6-carboxylic acid {trans-4-[2-(7-fluoro-quinoxalin-2-yloxy)-ethyl]-cyclohexyl}-amide The title compound is prepared as a white amorphous lyophilized solid following Scheme 1 and in analogy to Example 1 using 2-chloro-7-fluoro-quinoxaline, [trans-4-(2- hydroxy-ethyl)-cyclohexyl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.58 (s, 1H), 8.20 (d, J=8.0 Hz, 1H), 8.09 (dd, J=6.0, 9.0 Hz, 1H), 7.52-7.64 (m, 2H), 7.37-7.47 (m, 3H), 4.51 (t, J=6.8 Hz, 2H), 3.71 (m, 1H), 3.50 (s, 2H), 2.85 (m, 4H), 2.76 (m, 2H), 1.50 (m, 1H), 1.35 (m, 2H), 1.12 (m, 2H).

MS m/z (+ESI): 481.2 [M+H]$^+$.

Example 8

3-oxo-3,4-dihydro-2H-benzo[1,4]thiazine-6-carboxylic acid {1-[3-(7-methoxy-quinoxalin-2-yloxy)-propyl]-azetidin-3-yl}-amide The title compound is prepared as an off-white lyophilizated powder following Scheme 1 and in analogy to Example 1 using 2-chloro-7-methoxy-quinoxaline, 3-bromo-propan-1-ol, azetidin-3-yl-carbamic acid tert-butyl ester and 3-oxo-3, 4-dihydro-2H-benzo[1,4]thiazine-6-carboxylic acid as starting materials.

$^1$H-NMR (400 MHz, DMSO-d$_6$) δ ppm: 10.70 (s, 1H), 8.79 (d, J=6.9 Hz, 1H), 8.39 (s, 1H), 7.87 (d, J=9.0 Hz, 1H), 7.40-7.50 (m, 3H), 7.20-7.28 (m, 2H), 4.37-4.42 (m, 3H), 3.92 (s, 3H), 3.65 (t, J=7.3 Hz, 2H), 3.51 (s, 2H), 3.06 (t, J=7.3 Hz, 2H), 2.65 (m, 2H), 1.85 (m, 2H).

MS m/z (+ESI): 480.2 [M+H]$^+$.

Example 9

6-[({1-[3-(7-methoxy-quinoxalin-2-yloxy)-propyl]-piperidin-4-ylmethyl}-amino)-methyl]-4H-pyrido[3,2-b][1,4]oxazin-3-one Preparation of C-{1-[3-(7-methoxy-quinoxalin-2-yloxy)-propyl]-piperidin-4-yl}-methylamine The title compound is prepared as a brown viscous oil following Scheme 1 and in analogy to Example 1 using 2-chloro-7-methoxy-quinoxaline, 3-bromo-propan-1-ol and piperidin-4-ylmethyl-carbamic acid tert-butyl ester as starting materials.

$^1$H-NMR (400 MHz, DMSO-d$_6$) δ ppm: 8.40 (s, 1H), 7.88 (d, J=8.9 Hz, 1H), 7.21-7.27 (m, 2H), 4.44 (t, J=6.6 Hz, 2H), 3.92 (s, 3H), 2.89 (m, 2H), 2.37-2.48 (m, 4H), 1.97 (m, 2H), 1.82 (m, 2H), 1.65 (m, 2H), 1.00-1.22 (m, 3H).

MS m/z (+ESI): 331.3 [M+H]$^+$.

Preparation of 6-[({1-[3-(7-methoxy-quinoxalin-2-yloxy)-propyl]-piperidin-4-ylmethyl}-amino)-methyl]-4H-pyrido[3,2-b][1,4]oxazin-3-one 3-Oxo-3,4-dihydro-2H-pyrido[3,2-b][1,4]oxazine-6-carbaldehyde (22 mg, 0.12 mmol 1.0 eq) is added at room temperature to a stirred solution of C-{1-[3-(7-methoxy-quinoxalin-2-yloxy)-propyl]-piperidin-4-yl}-methylamine (40 mg, 0.12 mmol, 1.0 eq) in 1,2-dichloroethane (2 mL) and methanol (0.5 mL), followed by acetic acid (9 μL, 0.15 mmol, 1.3 eq) and sodium cyanoborohydride (11 mg, 0.15 mmol, 1.3 eq). After 15 hours stirring at room temperature, the reaction mixture is extracted with dichloromethane (3×5 mL) and a saturated sodium hydrogen carbonate aqueous solution (5 mL). The combined organic layers are dried over sodium sulfate, filtered and concentrated to give a residue that is purified by preparative HPLC to afford 6-[({1-[3-(7-methoxy-quinoxalin-2-yloxy)-propyl]-piperidin-4-ylmethyl}- amino)-methyl]-4H-pyrido[3,2-b][1,4]oxazin-3-one as a white viscous oil (18 mg, 29% yield).

$^1$H-NMR (400 MHz, DMSO-d$_6$) δ ppm: 11.20 (br, 1H), 8.39 (s, 1H), 8.20 (s, 1H), 7.88 (d, J=9.0 Hz, 1H), 7.31 (d, J=8.1 Hz, 1H), 7.25 (m, 2H), 7.01 (d, J=8.1 Hz, 1H), 4.63 (s, 2H), 4.45 (t, J=6.5 Hz, 2H), 3.92 (s, 3H), 3.70 (s, 2H), 2.94 (d, J=11.2 Hz, 2H), 2.43 (m, 4H), 1.88-2.04 (m, 4H), 1.69 (m, 2H), 1.44 (m, 1H), 1.15 (m, 2H).

MS m/z (+ESI): 493.3 [M+H]$^+$.

Example 10

(2,3-dihydro-benzo[1,4]dioxin-6-ylmethyl)-{1-[2-(7-methoxy-quinoxalin-2-yloxy)-ethyl]-piperidin-4-yl}-methyl-amine Preparation of 4-[(2,3-dihydro-benzo[1,4]dioxin-6-ylmethyl)-methyl-amino]-piperidine-1-carboxylic acid tert-butyl ester 2,3-dihydro-benzo[1,4]dioxine-6-carbaldehyde (153 mg, 0.93 mmol, 1.0 eq) is added at room temperature to a stirred solution of 4-methylamino-piperidine-1-carboxylic acid tert-butyl ester (200 mg, 0.93 mmol, 1.0 eq) in 1,2-dichloroethane (8 mL) and methanol (2 mL), followed by acetic acid (61 μL, 1.07 mmol, 1.15 eq) and sodium cyanoborohydride (76 mg, 1.21 mmol, 1.3 eq). After 15 hours stirring at room temperature, the reaction mixture is extracted with dichloromethane (3×20 mL) and a saturated sodium hydrogen carbonate aqueous solution (20 mL). The combined organic layers are dried over sodium sulfate, filtered and concentrated to give a residue that is purified by column chromatography (silica gel, eluent: cyclohexane:ethyl acetate, 3:1 to 1:3, v/v) to afford 4-[(2,3-dihydro-benzo[1,4]dioxin-6-ylmethyl)-methyl-amino]-piperidine-1-carboxylic acid tert-butyl ester as an off-white oil (195 mg, 55% yield).

MS m/z (+ESI): 363.2 [M+H]$^+$.

Preparation of (2,3-dihydro-benzo[1,4]dioxin-6-ylmethyl)-methyl-piperidin-4-yl-amine Trifluoroacetic acid (591 μL, 7.67 mmol, 15.0 eq) is added at 0° C. to a stirred solution of 4-[(2,3-dihydro-benzo[1,4]dioxin-6-ylmethyl)-methyl-amino]-piperidine-1-carboxylic acid tert-butyl ester (195 mg, 0.51 mmol, 1.0 eq) in dichloromethane (10 mL). After 3 hours stirring at room temperature, the reaction mixture is extracted with dichloromethane (3×10 mL) and water (10 mL) and the pH is adjusted to 12 by the addition of a 1N sodium hydroxide aqueous solution. The combined organic layers are dried over sodium sulfate, filtered and concentrated to afford (2,3-dihydro-benzo[1,4]dioxin-6-ylmethyl)-methyl-piperidin-4-yl-amine as a light yellow solid (148 mg, 99% yield).

MS m/z (+ESI): 263.2 [M+H]$^+$.

Preparation of 2-{4-[(2,3-dihydro-benzo[1,4]dioxin-6-ylmethyl)-methyl-amino]-piperidin-4-yl}-ethanol 2-Bromo-ethanol (36 μL, 0.51 mmol, 1.0 eq) is added at room temperature to a stirred solution of (2,3-dihydro-benzo[1,4]dioxin-6-ylmethyl)-methyl-piperidin-4-yl-amine (148 mg, 0.51 mmol, 1.0 eq) in N,N-dimethylformamide (4 mL), followed by potassium carbonate (70 mg, 0.51 mmol, 1.0 eq). After 15 hours stirring at room temperature, solvent is evaporated and the residue is extracted with ethyl acetate (3×8 mL) and water (8 mL). pH of the aqueous layer is neutralized with a 0.1 N hydrochloric acid aqueous solution. The combined organic layers are dried over sodium sulfate, filtered and concentrated to afford 2-{4-[(2,3-dihydro-benzo[1,4]dioxin-6-ylmethyl)-methyl-amino]-piperidin-4-yl}-ethanol as a yellow semisolid (160 mg, 93% yield).

MS m/z (+ESI): 307.3 [M+H]$^+$.

Preparation of (2,3-dihydro-benzo[1,4]dioxin-6-ylmethyl)-{1-[2-(7-methoxy-quinoxalin-2-yloxy)-ethyl]-piperidin-4-yl}-methyl-amine Sodium hydride (55% purity, 20 mg, 0.47 mmol, 1.0 eq) is added at room temperature to a stirred solution of 2-chloro-7-methoxy-quinoxaline (95 mg, 0.47 mmol, 1.0 eq) in N,N-dimethylformamide (4 mL), followed by 2-{4-[(2,3-dihydro-benzo[1,4]dioxin-6-ylmethyl)-methyl-amino]-piperidin-4-yl}-ethanol (160 mg, 0.47 mmol, 1.0 eq). After 4 hours stirring at room temperature, solvent is evaporated, and the residue is extracted with dichloromethane (3×10 mL) and water (10 mL). The combined organic layers are dried over sodium sulfate, filtered and concentrated to give a residue that is purified by preparative HPLC to afford (2,3-dihydro-benzo[1,4]dioxin-6-ylmethyl)-{1-[2-(7-methoxy-quinoxalin-2-yloxy)-ethyl]-piperidin-4-yl}-methyl-amine as a light yellow oil (11 mg, 5% yield).

MS m/z (+ESI): 465.4 [M+H]$^+$.

Example 11

6-({1-[3-(7-methoxy-quinoxalin-2-yloxy)-propyl]-piperidin-3-ylamino}-methyl)-4H-benzo[1,4]thiazin-3-one The title compound is prepared as a yellow amorphous lyophilizated solid following Scheme 1 and in analogy to Examples 1 and 9 using 2-chloro-7-methoxy-quinoxaline, 3-bromo-propan-1-ol, piperidin-3-yl-carbamic acid tert-butyl ester and 3-oxo-3,4-dihydro-2H-benzo[1,4]thiazine-6-carbaldehyde as starting materials.

$^1$H-NMR (400 MHz, DMSO-d$_6$) δ ppm: 10.52 (s, 1H), 8.39 (s, 1H), 7.88 (d, J=9.0 Hz, 1H), 7.25 (m, 3H), 6.95 (m, 2H), 4.46 (m, 2H), 3.92 (s, 3H), 3.67 (s, 2H), 3.57 (s, 2H), 2.70-2.90 (m, 2H), 2.43 (m, 3H), 1.94 (m, 3H), 1.79 (m, 2H), 1.60 (m, 1H), 1.39 (m, 1H), 1.07 (m, 1H).

MS m/z (+ESI): 494.3 [M+H]$^+$.

Example 12

3-oxo-3,4-dihydro-2H-benzo[1,4]thiazine-6-carboxylic acid {1-[2-(8-methoxy-quinoxalin-2-yloxy)-ethyl]-piperidin-4-yl}-amide Preparation of {1-[2-(8-methoxy-quinoxalin-2-yloxy)-ethyl]-piperidin-4-yl}-carbamic acid tert-butyl ester Sodium hydride (98% purity, 148 mg, 6.10 mmol, 1.5 eq) is added at room temperature to a stirred solution of 2-chloro-8-methoxy-quinoxaline (800 mg, 4.07 mmol, 1.0 eq) in N,N-dimethylformamide (80 mL), followed by [1-(2-hydroxy-ethyl)-piperidin-4-yl]-carbamic acid tert-butyl ester (1.17 g, 4.07 mmol, 1.0 eq). After 15 hours stirring at room temperature and 4 hours at 80° C., solvent is evaporated, and the residue is extracted with dichloromethane (3×30 mL) and water (30 mL). The combined organic layers are dried over sodium sulfate, filtered and concentrated to give a residue that is purified by column chromatography (silica gel, eluent: cyclohexane:ethyl acetate:methanol, 1:3:0 to 0:9:1, v/v/v) to afford {1-[2-(8-methoxy-quinoxalin-2-yloxy)-ethyl]-piperidin-4-yl}-carbamic acid tert-butyl ester as an orange solid (825 mg, 48% yield).

MS m/z (+ESI): 403.3 [M+H]$^+$.

Preparation of 3-oxo-3,4-dihydro-2H-benzo[1,4]thiazine-6-carboxylic acid {1-[2-(8-methoxy-quinoxalin-2-yloxy)-ethyl]-piperidin-4-yl}-amide The title compound is prepared as an off-white lyophilizated powder following Scheme 1 and in analogy to Example 1 using {1-[2-(8-methoxy-quinoxalin-2-yloxy)-ethyl]-piperidin-4-yl}-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.60 (s, 1H), 8.21 (d, J=7.7 Hz, 1H), 7.55-7.60 (m, 2H), 7.37-7.44 (m, 3H), 7.26 (dd, J=1.8, 6.7 Hz, 1H), 4.57 (t, J=5.6 Hz, 2H), 3.97 (s, 3H), 3.75 (m, 1H), 3.50 (s, 2H), 3.03 (m, 2H), 2.80 (t, J=5.6 Hz, 2H), 2.18 (m, 2H), 1.78 (m, 2H), 1.55 (m, 2H).

MS m/z (+ESI): 494.4 [M+H]$^+$.

Example 13

3-oxo-3,4-dihydro-2H-benzo[1,4]thiazine-6-carboxylic acid {1-[2-(7-nitro-quinoxalin-2-yloxy)-ethyl]-piperidin-4-yl}-amide The title compound is prepared as a yellow lyophilized powder following Scheme 1 and in analogy to Examples 1 and 12 using 2-chloro-7-nitro-quinoxaline, [1-(2-hydroxy-ethyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.83 (s, 1H), 8.61 (d, J=2.5 Hz, 1H), 8.38 (m, 1H), 8.19-8.28 (m, 2H), 7.38-7.46 (m, 3H), 4.64 (t, J=5.8 Hz, 2H), 3.78 (m, 1H), 3.58 (s, 2H), 3.02 (m, 2H), 2.82 (t, J=5.8 Hz, 2H), 2.18 (m, 2H), 1.77 (m, 2H), 1.55 (m, 2H).

MS m/z (+ESI): 509.2 [M+H]$^+$.

Example 14

3-oxo-3,4-dihydro-2H-benzo[1,4]thiazine-6-carboxylic acid {1-[3,3,3-trifluoro-2-(7-methoxy-quinoxalin-2-yloxy)-propyl]-piperidin-4-yl}-amide The title compound is prepared as an off-white lyophilizated powder following Scheme 1 and in analogy to Example 1 using 2-chloro-7-methoxy-quinoxaline, 3-bromo-1,1,1-trifluoro-2-propanol, piperidin-4-yl-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.61 (s, 1H), 8.58 (s, 1H), 8.10 (d, J=7.5 Hz, 1H), 7.97 (d, J=9.0 Hz, 1H), 7.25-7.40 (m, 5H), 6.30 (m, 1H), 3.93 (s, 3H), 3.68 (m, 1H), 3.48 (s, 2H), 3.15 (m, 1H), 2.82-3.00 (m, 3H), 2.00-2.35 (m, 2H), 1.65 (m, 2H), 1.15-1.35 (m, 2H).

MS m/z (+ESI): 562.3 [M+H]$^+$.

Example 15

7-chloro-3-oxo-3,4-dihydro-2H-benzo[1,4]thiazine-6-carboxylic acid {1-[2-(7-methoxy-quinoxalin-2-yloxy)-ethyl]-piperidin-4-yl}-amide The title compound is prepared as white lyophilized powder (11 mg, 16% yield) following Scheme 1 and in analogy to Example 1 using 7-chloro-3-oxo-3,4-dihydro-2H-benzo[1,4] thiazine-6-carboxylic acid (31 mg, 0.13 mmol, 1.0 eq) and 1-[2-(7-methoxy-quinoxalin-2-yloxy)-ethyl]-piperidin-4-ylamine (40 mg, 0.13 mmol, 1.0 eq) as starting materials.

$^1$H-NMR (400 MHz, DMSO-d$_6$) δ ppm: 10.70 (s, 1H), 8.42 (s, 1H), 8.35 (d, J=7.6 Hz, 1H), 7.89 (d, J=8.9 Hz, 1H), 7.49 (s, 1H), 7.26 (d, J=9.2 Hz, 1H), 7.22 (s, 1H), 6.95 (s, 1H), 4.55 (m, 2H), 3.93 (s, 3H), 3.72 (m, 1H), 3.51 (s, 2H), 2.96 (m, 2H), 2.79 (m, 2H), 2.18 (m, 2H), 1.79 (m, 2H), 1.50 (m, 2H).
MS m/z (+ESI): 528.2 [M+H]$^+$.

Example 16

7-chloro-3-oxo-3,4-dihydro-2H-benzo[1,4]thiazine-6-carboxylic acid {1-[2-(6-methoxy-[1,5]naphthyridin-3-yloxy)-ethyl]-piperidin-4-yl}-amide

Preparation of {1-[2-(6-methoxy-[1,5]naphthyridin-3-yloxy)-ethyl]-piperidin-4-yl}-carbamic acid tert-butyl ester

[1-(2-hydroxy-ethyl)-piperidin-4-yl]-carbamic acid tert-butyl ester (50 mg, 0.19 mmol, 1.0 eq) is added at room temperature to a stirred solution of 6-methoxy-[1,5]naphthyridin-3-ol (37 mg, 0.19 mmol, 1.0 eq) in tetrahydrofuran (5 mL), followed by triphenylphosphine polymer-bound (3 mmol/g, 193 mg, 0.58 mmol, 3.0 eq) and diisopropyl azodicarboxylate (115 μL, 0.58 mmol, 3.0 eq). After 3 hours stirring at room temperature, the polymer-bound is filtered off and washed successively with tetrahydrofuran (5 mL), dichloromethane (5 mL) and methanol (5 mL). The resulting solution is concentrated and the residue is extracted with ethyl acetate (3×10 mL) and water (10 mL). The combined organic layers are dried over sodium sulfate, filtered and concentrated to give a crude that is purified by column chromatography (silica gel, eluent: cyclohexane:ethyl acetate:methanol, 4:1:0 to 0:9:1, v/v/v) to afford {1-[2-(6-methoxy-[1,5]naphthyridin-3-yloxy)-ethyl]-piperidin-4-yl}-carbamic acid tert-butyl ester as an orange solid (35 mg, 33% yield).

$^1$H-NMR (400 MHz, DMSO-d$_6$) δ ppm: 8.53 (d, J=2.7 Hz, 1H), 8.19 (dd, J=0.7, 9.0 Hz, 1H), 7.61 (dd, J=0.7, 2.7 Hz, 1H), 7.07 (d, J=9.0 Hz, 1H), 6.75 (d, J=7.7 Hz, 1H), 4.27 (t, J=5.6 Hz, 2H), 4.02 (s, 3H), 3.20 (m, 1H), 2.90 (m, 2H), 2.75 (t, J=5.6 Hz, 2H), 2.07 (m, 2H), 1.70 (m, 2H), 1.37 (m, 11H).
MS m/z (+ESI): 403.2 [M+H]$^+$.

Alternative

Preparation of methanesulfonic acid 2-(tert-butoxycarbonylamino-piperidin-1-yl)-ethyl ester Triethylamine (515 μL, 3.69 mmol, 0.95 eq) is added at 0° C. to a stirred solution of [1-(2-hydroxy-ethyl)-piperidin-4-yl]-carbamic acid tert-butyl ester (1.0 g, 3.89 mmol, 1.0 eq) in dichloromethane (40 mL), followed by the dropwise addition of methanesulfonyl chloride (286 μL, 3.69 mmol, 0.95 eq). After 2 hours stirring at 0° C., the reaction mixture is extracted with dichloromethane (3×30 mL) and water (30 mL). The combined organic layers are dried over sodium sulfate, filtered and concentrated to afford methanesulfonic acid 2-(tert-butoxycarbonylamino-piperidin-1-yl)-ethyl ester as an off-white semisolid (961 mg, 61% yield, 80% ELSD purity) that is directly engaged in the next step.

Preparation of {1-[2-(6-methoxy-[1,5]naphthyridin-3-yloxy)-ethyl]-piperidin-4-yl}-carbamic acid tert-butyl ester Sodium hydride (55% purity, 9 mg, 0.22 mmol, 1.5 eq) is added at room temperature to a stirred solution of 6-methoxy-[1,5]naphthyridin-3-ol (42 mg, 0.22 mmol, 1.0 eq) in N,N-dimethylformamide (5 mL), followed by methanesulfonic acid 2-(4-tert-butoxycarbonylamino-piperidin-1-yl)-ethyl ester (102 mg, 0.22 mmol, 1.0 eq). The reaction mixture is irradiated by microwaves at 110° C. for 10 minutes, then solvent is evaporated, and the residue is extracted with ethyl acetate (3×10 mL) and water (10 mL). The combined organic layers are dried over sodium sulfate, filtered and concentrated to give a residue that is purified by column chromatography (silica gel, eluent: cyclohexane:ethyl acetate:methanol, 1:1:0 to 0:9:1, v/v/v) to afford {1-[2-(6-methoxy-[1,5]naphthyridin-3-yloxy)-ethyl]-piperidin-4-yl}-carbamic acid tert-butyl ester as an orange solid (27 mg, 29% yield).

Preparation of 7-chloro-3-oxo-3,4-dihydro-2H-benzo[1,4]thiazine-6-carboxylic acid {1-[2-(6-methoxy-[1,5]naphthyridin-3-yloxy)-ethyl]-piperidin-4-yl}-amide The title compound is prepared as an off-white lyophilizated powder following Scheme 1 and in analogy to Example 1 using {1-[2-(6-methoxy-[1,5]naphthyridin-3-yloxy)-ethyl]-piperidin-4-yl}-carbamic acid tert-butyl ester and 7-chloro-3-oxo-3,4-dihydro-2H-benzo[1,4]thiazine-6-carboxylic acid as starting materials.
MS m/z (+ESI): 528.2 [M+H]$^+$.

Example 17

3-oxo-3,4-dihydro-2H-pyrido[3,2-b][1,4]thiazine-6-carboxylic acid {1-[2-(7-methoxy-quinolin-2-yloxy)-ethyl]-piperidin-4-yl}-amide The title compound is prepared as an off-white lyophilizated powder following Scheme 1 and in analogy to Examples 1 and 12 using 2-chloro-7-methoxy-quinoline, [1-(2-hydroxy-ethyl)-piperidin-4-yl]-carbamic acid tert-butyl ester and 3-oxo-3,4-dihydro-2H-pyrido[3,2-b][1,4]thiazine-6-carboxylic acid as starting materials.

$^1$H-NMR (400 MHz, DMSO-d$_6$) δ ppm: 11.00 (s, 1H), 8.14 (d, J=8.6 Hz, 1H), 8.02 (d, J=8.1 Hz, 1H), 7.95 (d, J=7.9 Hz, 1H), 7.77 (d, J=8.8 Hz, 1H), 7.59 (d, J=7.8 Hz, 1H), 7.17 (d, J=2.5 Hz, 1H), 7.06 (dd, J=2.5, 8.8 Hz, 1H), 6.84 (d, J=8.8 Hz, 1H), 4.53 (t, J=5.9 Hz, 2H), 3.89 (s, 3H), 3.79 (m, 1H), 3.64 (s, 2H), 2.94 (m, 2H), 2.81 (t, J=5.9 Hz, 2H), 2.30 (m, 2H), 1.88 (m, 2H), 1.55 (m, 2H).
MS m/z (+ESI): 494.2 [M+H]$^+$.

Example 18

3-oxo-3,4-dihydro-2H-benzo[1,4]thiazine-6-carboxylic acid {1-[2-(7-methoxy-[1,5]naphthyridin-2-yloxy)-ethyl]-piperidin-4-yl}-amide

Preparation of 2,7-dimethoxy-[1,5]naphthyridine

Potassium carbonate (13.84 g, 100.1 mmol, 2.0 eq) is added at room temperature to a stirred solution of 6-methoxy-[1,5]naphthyridin-3-ol (9.8 g, 50.06 mmol, 1.0 eq) in acetone (300 mL), followed by iodomethane (3.74 mL, 60.1 mmol, 1.2 eq). After 4 hours stirring under reflux conditions, the solid is removed by filtration and the filtrate is concentrated to give a residue that is extracted with ethyl acetate (3×100 mL) and water (100 mL). The combined organic layers are washed with brine, dried over sodium sulfate, filtered and concentrated to give a residue that is purified by column chromatography (silica gel, eluent: petroleum ether:ethyl acetate, 6:1, v/v) to afford 2,7-dimethoxy-[1,5]naphthyridine as a yellow solid (5.2 g, 52% yield).

$^1$H-NMR (400 MHz, CDCl$_3$) δ ppm: 8.53 (d, J=2.4 Hz, 1H), 8.19 (d, J=8.8 Hz, 1H), 7.50 (d, J=2.4 Hz, 1H), 6.98 (d, J=8.8 Hz, 1H), 4.07 (s, 3H), 3.97 (s, 3H).

MS m/z (+ESI): 191.3 [M+H]$^+$.

Preparation of
2-chloro-7-methoxy-[1,5]naphthyridine

A mixture of 2,7-dimethoxy-[1,5]naphthyridine (5.0 g, 26.29 mmol, 1.0 eq) and phosphorus oxychloride (4.9 mL, 52.58 mmol, 2.0 eq) in N,N-dimethylformamide (100 mL) is stirred at 0° C. for 1 hour then at 80° C. for 1 hour. The reaction mixture is cooled to 0° C., quenched with 10 mL of saturated sodium acetate aqueous solution and then stirred at 30° C. for 30 minutes. The mixture is extracted with ethyl acetate (3×60 mL). The combined organic layers are dried over sodium sulfate, filtered and concentrated to give a crude that is purified by column chromatography (silica gel, eluent: ethyl acetate:petroleum ether, 1:6, v/v) to afford 2-chloro-7-methoxy-[1,5]naphthyridine as a yellow solid (3.3 g, 64% yield).

$^1$H-NMR (400 MHz, Acetone-d$_6$) δ ppm: 8.70 (d, J=2.8 Hz, 1H), 8.34 (d, J=8.4 Hz, 1H), 7.63 (d, J=2.8 Hz, 1H), 7.59 (d, J=8.4 Hz, 1H), 4.06 (s, 3H).

MS m/z (+ESI): 195.2 [M+H]$^+$.

Preparation of 3-oxo-3,4-dihydro-2H-benzo[1,4]thiazine-6-carboxylic acid {1-[2-(7-methoxy-[1,5]naphthyridin-2-yloxy)-ethyl]-piperidin-4-yl}-amide The title compound is prepared as an off-white lyophilizated powder following Scheme 1 and in analogy to Example 1 using 2-chloro-7-methoxy-[1,5]naphthyridine, [1-(2-hydroxy-ethyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.54 (d, J=2.8 Hz, 1H), 8.14-8.23 (m, 2H), 7.57 (d, J=2.8 Hz, 1H), 7.38-7.45 (m, 3H), 7.08 (d, J=9.0 Hz, 1H), 4.55 (t, J=5.9 Hz, 2H), 3.96 (s, 3H), 3.77 (m, 1H), 3.50 (s, 2H), 3.02 (m, 2H), 2.80 (t, J=5.9 Hz, 2H), 2.18 (m, 2H), 1.79 (m, 2H), 1.58 (m, 2H).

MS m/z (+ESI): 494.2 [M+H]$^+$.

Example 19

7-chloro-3-oxo-3,4-dihydro-2H-benzo[1,4]thiazine-6-carboxylic acid {1-[2-(7-methoxy-[1,5]naphthyridin-2-yloxy)-ethyl]-piperidin-4-yl}-amide The title compound is prepared as an off-white lyophilizated powder following Scheme 1 and in analogy to Example 1 using 2-chloro-7-methoxy-[1,5]naphthyridine, [1-(2-hydroxy-ethyl)-piperidin-4-yl]-carbamic acid tert-butyl ester and 7-chloro-3-oxo-3,4-dihydro-2H-benzo[1,4]thiazine-6-carboxylic acid as starting materials.

$^1$H-NMR (400 MHz, DMSO-d$_6$) δ ppm: 10.70 (s, 1H), 8.54 (d, J=2.7 Hz, 1H), 8.35 (d, J=7.8 Hz, 1H), 8.19 (d, J=9.0 Hz, 1H), 7.56 (d, J=2.7 Hz, 1H), 7.49 (s, 1H), 7.07 (d, J=9.0 Hz, 1H), 6.95 (s, 1H), 4.54 (t, J=5.8 Hz, 2H), 3.96 (s, 3H), 3.72 (m, 1H), 3.50 (s, 2H), 2.98 (m, 2H), 2.78 (t, J=5.8 Hz, 2H), 2.20 (m, 2H), 1.80 (m, 2H), 1.50 (m, 2H).

MS m/z (+ESI): 528.2 [M+H]$^+$.

Example 20

3-oxo-3,4-dihydro-2H-pyrido[3,2-b][1,4]thiazine-6-carboxylic acid {1-[2-(7-methoxy-quinoxalin-2-yloxy)-ethyl]-piperidin-4-yl}-amide The title compound is prepared as an off-white lyophilizated powder following Scheme 1 and in analogy to Example 1 using 2-chloro-7-methoxy-quinoxaline, [1-(2-hydroxy-ethyl)-piperidin-4-yl]-carbamic acid tert-butyl ester and 3-oxo-3,4-dihydro-2H-pyrido[3,2-b][1,4]thiazine-6-carboxylic acid as starting materials.

$^1$H-NMR (400 MHz, DMSO-d$_6$) δ ppm: 11.00 (s, 1H), 8.42 (s, 1H), 8.01 (d, J=8.1 Hz, 1H), 7.95 (d, J=7.8 Hz, 1H), 7.89 (d, J=8.9 Hz, 1H), 7.58 (d, J=7.8 Hz, 1H), 7.22-7.28 (m, 2H), 4.56 (t, J=5.7 Hz, 2H), 3.93 (s, 3H), 3.78 (m, 1H), 3.64 (s, 2H), 2.93 (m, 2H), 2.81 (t, J=5.7 Hz, 2H), 2.28 (m, 2H), 1.84 (m, 2H), 1.52 (m, 2H).

MS m/z (+ESI): 495.2 [M+H]$^+$.

Example 21

3-oxo-3,4-dihydro-2H-benzo[1,4]thiazine-6-carboxylic acid {1-[2-(7-methoxy-quinoxalin-2-yloxy)-ethyl]-piperidin-4-yl}-amide The title compound is prepared as a white amorphous lyophilizated solid following Scheme 1 and in analogy to Example 1 using 2-chloro-quinoxaline, [1-(2-hydroxy-ethyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.62 (s, 1H), 8.21 (d, J=7.8 Hz, 1H), 8.02 (dd, J=1.3, 8.2 Hz, 1H), 7.84 (m, 1H), 7.77 (m, 1H), 7.65 (m, 1H), 7.42 (m, 3H), 4.58 (t, J=5.8 Hz, 2H), 3.75 (m, 1H), 3.50 (s, 2H), 3.02 (m, 2H), 2.81 (t, J=5.8 Hz, 2H), 2.17 (m, 2H), 1.78 (m, 2H), 1.55 (m, 2H).

MS m/z (+ESI): 464.2 [M+H]$^+$.

Example 22

3-oxo-3,4-dihydro-2H-benzo[1,4]thiazine-6-carboxylic acid {1-[2-(7-methoxy-quinoxalin-2-yloxy)-ethyl]-azetidin-3-yl}-amide The title compound is prepared as an off-white lyophilizated powder following Scheme 1 and in analogy to Example 1 using 2-chloro-7-methoxy-quinoxaline, 2-bromo-ethanol, azetidin-3-yl-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.74 (s, 1H), 8.82 (d, J=7.0 Hz, 1H), 8.41 (s, 1H), 7.89 (d, J=9.0 Hz, 1H), 7.40-7.45 (m, 3H), 7.20-7.30 (m, 2H), 4.44-4.55 (m, 3H), 3.92 (s, 3H), 3.78 (m, 2H), 3.50 (s, 2H), 3.35 (m, 2H), 3.00 (m, 2H).

MS m/z (+ESI): 466.1 [M+H]$^+$.

Example 23

3-oxo-3,4-dihydro-2H-benzo[1,4]thiazine-6-carboxylic acid {1-[3-(7-methoxy-quinoxalin-2-yloxy)-propyl]-pyrrolidin-3-ylamide The title compound is prepared as a white solid following Scheme 1 and in analogy to Example 1 using 2-chloro-7-methoxy-quinoxaline, 3-bromo-propan-1-ol, pyrrolidin-3-yl-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.67 (s, 1H), 8.47 (d, J=6.8 Hz, 1H), 8.40 (s, 1H), 7.88 (d, J=8.8 Hz, 1H), 7.46 (m, 2H), 7.38 (d, J=8.0 Hz, 1H), 7.25 (m, 2H), 4.47 (t, J=6.8 Hz, 2H), 4.39 (m, 1H), 3.92 (m, 3H), 3.50 (s, 2H), 2.86 (m, 2H), 2.45-2.70 (m, 4H), 2.15 (m, 1H), 2.00 (m, 2H), 1.78 (m, 1H).
MS m/z (+ESI): 480.2 [M+H]$^+$.

Example 24

7-chloro-3-oxo-3,4-dihydro-2H-benzo[1,4]thiazine-6-carboxylic acid {1-[2-(7-methoxy-quinoxalin-2-yloxy)-ethyl]-piperidin-4-ylmethyl}-amide The title compound is prepared as an off-white solid following Scheme 1 and in analogy to Example 1 using 2-chloro-7-methoxy-quinoxaline, 2-bromo-ethanol, piperidin-4-ylmethyl-carbamic acid tert-butyl ester and 7-chloro-3-oxo-3,4-dihydro-2H-benzo[1,4]thiazine-6-carboxylic acid as starting materials.

$^1$H-NMR (400 MHz, DMSO-d$_6$) δ ppm: 10.72 (s, 1H), 8.44 (t, J=5.8 Hz, 1H), 8.41 (s, 1H), 7.89 (d, J=9.0 Hz, 1H), 7.49 (s, 1H), 7.25 (m, 2H), 6.97 (s, 1H), 4.55 (t, J=5.8 Hz, 2H), 3.92 (s, 3H), 3.52 (s, 2H), 3.09 (t, J=6.2 Hz, 2H), 2.98 (m, 2H), 2.78 (t, J=5.8 Hz, 2H), 2.07 (m, 2H), 1.70 (m, 2H), 1.53 (m, 1H), 1.22 (m, 2H).
MS m/z (+ESI): 542.3 [M+H]$^+$.

Example 25

6-[({1-[2-(7-methoxy-quinoxalin-2-yloxy)-ethyl]-piperidin-4-yl}-methyl-amino)-methyl]-4H-benzo[1,4]thiazin-3-one Preparation of 6-({1-[2-(7-methoxy-quinoxalin-2-yloxy)-ethyl]-piperidin-4-ylamino}-methyl)-4H-benzo[1,4]thiazin-3-one The title compound is prepared as a yellow viscous oil following Scheme 1 and in analogy to Example 9 using 2-chloro-7-methoxy-quinoxaline, [1-(2-hydroxy-ethyl)-piperidin-4-yl]-carbamic acid tert-butyl ester and 3-oxo-3,4-dihydro-2H-benzo[1,4]thiazine-6-carbaldehyde as starting materials.
MS m/z (+ESI): 480.2 [M+H]$^+$.

Preparation of 6-[({1-[2-(7-methoxy-quinoxalin-2-yloxy)-ethyl]-piperidin-4-yl}-methyl-amino)-methyl]-4H-benzo[1,4]thiazin-3-one Paraformaldehyde (29 mg, 0.10 mmol, 1.0 eq) is added at room temperature to a stirred solution of 6-({1-[2-(7-methoxy-quinoxalin-2-yloxy)-ethyl]-piperidin-4-ylamino}-methyl)-4H-benzo[1,4]thiazin-3-one (50 mg, 0.10 mmol, 1.0 eq) in 1,2-dichloroethane (2 mL) and methanol (0.5 mL), followed by acetic acid (7 μL, 0.12 mmol, 1.3 eq) and sodium cyanoborohydride (9 mg, 0.12 mmol, 1.3 eq). After 15 hours stirring at room temperature, the reaction mixture is extracted with dichloromethane (3×5 mL) and a saturated sodium hydrogen carbonate aqueous solution (5 mL). The combined organic layers are dried over sodium sulfate, filtered and concentrated to give a residue that is purified by preparative HPLC to afford 6-[({1-[2-(7-methoxy-quinoxalin-2-yloxy)-ethyl]-piperidin-4-yl}-methyl-amino)-methyl]-4H-benzo[1,4]thiazin-3-one as a light brown viscous oil (11 mg, 21% yield).
MS m/z (+ESI): 494.3 [M+H]$^+$.

Example 26

5-thiophen-2-yl-isoxazole-3-carboxylic acid {1-[2-(7-methoxy-quinoxalin-2-yloxy)-ethyl]-pyrrolidin-3-ylmethyl}-amide The title compound is prepared as an orange semi-solid following Scheme 1 and in analogy to Example 1 using 2-chloro-7-methoxy-quinoxaline, 2-bromo-ethanol, pyrrolidin-3-ylmethyl-carbamic acid tert-butyl ester and 5-thiophen-2-yl-isoxazole-3-carboxylic acid as starting materials.

$^1$H-NMR (400 MHz, DMSO-d$_6$) δ ppm: 8.77 (t, J=5.6 Hz, 1H), 8.38 (s, 1H), 7.86 (m, 2H), 7.75 (dd, J=1.1, 3.6 Hz, 1H), 7.23 (m, 3H), 7.10 (s, 1H), 4.55 (t, J=5.8 Hz, 2H), 3.92 (s, 3H), 3.27 (t, J=6.2 Hz, 2H), 2.91 (m, 2H), 2.70 (m, 2H), 2.40-2.65 (m, 3H), 1.90 (m, 1H), 1.52 (m, 1H).
MS m/z (+ESI): 480.2 [M+H]$^+$.

Example 27

7-chloro-3,4-dihydro-2H-benzo[1,4]thiazine-6-carboxylic acid {1-[3-(7-methoxy-quinoxalin-2-yloxy)-propyl]-pyrrolidin-3-ylmethyl}-amide The title compound is prepared as a light yellow lyophilizated powder following Scheme 1 and in analogy to Example 1 using 2-chloro-7-methoxy-quinoxaline, 3-bromo-propan-1-ol, pyrrolidin-3-ylmethyl-carbamic acid tert-butyl ester and 7-chloro-3,4-dihydro-2H-benzo[1,4]thiazine-6-carboxylic acid as starting materials.

$^1$H-NMR (400 MHz, DMSO-d$_6$) δ ppm: 8.38 (s, 1H), 8.17 (t, J=5.5 Hz, 1H), 7.88 (d, J=9.0 Hz, 1H), 7.24 (m, 2H), 6.91 (s, 1H), 6.55 (s, 1H), 6.28 (br, 1H), 4.49 (t, J=6.6 Hz, 2H), 3.92 (s, 3H), 3.48 (m, 2H), 3.18 (m, 2H), 2.99 (m, 2H), 2.33-2.70 (m, 7H), 2.00 (m, 2H), 1.90 (m, 1H), 1.50 (m, 1H).
MS m/z (+ESI): 528.3 [M+H]$^+$.

Example 28

6-methoxy-quinoline-3-carboxylic acid trans-4-[(3-oxo-3,4-dihydro-2H-benzo[1,4]thiazine-6-carbonyl)-amino]-cyclohexylmethyl ester Preparation of trans-4-tert-butoxycarbonylamino-cyclohexanecarboxylic acid trans-4-Amino-cyclohexanecarboxylic acid (10.0 g, 69.8 mmol, 1.0 eq) is suspended in dioxane (100 mL) and water (200 mL) and sodium hydrogen carbonate (7.0 g, 83.8 mmol, 1.2 eq) is added at room temperature, followed by a solution of di-tert-butyl-dicarbonate (21.3 g, 97.8 mmol, 1.4 eq) in dioxane (100 mL). After 24 hours stirring at room temperature, dioxane is evaporated and the pH of the aqueous residue is adjusted to 3 by the addition of a 1N hydrochloric acid aqueous solution and extracted with ethyl acetate (3×50 mL). The combined organic layers are dried over sodium sulfate, filtered and concentrated to afford trans-4-tert-butoxycarbonylamino-cyclohexanecarboxylic acid as a white solid (16.1 g, 93% yield).

$^1$H-NMR (400 MHz, DMSO-d$_6$) δ ppm: 12.05 (br, 1H), 6.72 (d, J=7.8 Hz, 1H), 3.15 (m, 1H), 2.08 (m, 1H), 1.75-1.92 (m, 4H), 1.37 (s, 9H), 1.05-1.35 (m, 4H).

MS m/z (+ESI): 266.2 [M+Na]$^+$.

Preparation of trans-4-tert-butoxycarbonylamino-cyclohexanecarboxylic acid methyl ester Potassium carbonate (877 mg, 6.34 mmol, 1.05 eq) is added at room temperature to a stirred solution of trans-4-tert-butoxycarbonylamino-cyclohexanecarboxylic acid (1.50 g, 6.04 mmol, 1.0 eq) in N,N-dimethylformamide (30 mL), followed by methyl iodide (395 μL, 6.34 mmol, 1.05 eq). After 5 hours stirring at room temperature, solvent is evaporated and the residue is extracted with ethyl acetate (3×30 mL) and water (30 mL). The combined organic layers are washed with brine (30 mL), dried over sodium sulfate, filtered and concentrated to afford trans-4-tert-butoxycarbonylamino-cyclohexanecarboxylic acid methyl ester as a yellow solid (1.60 g, 98% yield).

$^1$H-NMR (400 MHz, DMSO-d$_6$) δ ppm: 6.72 (d, J=7.8 Hz, 1H), 3.58 (s, 3H), 3.15 (m, 1H), 2.10 (m, 1H), 1.75-1.92 (m, 4H), 1.37 (s, 9H), 1.07-1.36 (m, 4H).

MS m/z (+ESI): 280.2 [M+Na]$^+$.

Preparation of trans-4-amino-cyclohexanecarboxylic acid methyl ester

Trifluoroacetic acid (13.47 mL, 19.94 mmol, 15.0 eq) is added at 0° C. to a stirred solution of trans-4-tert-butoxycarbonylamino-cyclohexanecarboxylic acid methyl ester (3.53 g, 11.66 mmol, 1.0 eq) in dichloromethane (100 mL). After 15 hours stirring at room temperature, the reaction mixture is extracted with dichloromethane (3×50 mL) and water (50 mL) and the pH is adjusted to 12 by the addition of a 1N sodium hydroxide aqueous solution. The combined organic layers are dried over sodium sulfate, filtered and concentrated to afford trans-4-amino-cyclohexanecarboxylic acid methyl ester as a yellow oil (1.53 g, 79% yield).

$^1$H-NMR (400 MHz, DMSO-d$_6$) δ ppm: 3.58 (s, 3H), 2.48 (m, 1H), 2.18 (m, 1H), 1.72-1.90 (m, 4H), 1.35 (qd, J=3.4, 13.2 Hz, 2H), 1.02 (qd, J=3.4, 13.2 Hz, 2H).

MS m/z (+ESI): 158.2 [M+H]$^+$.

Preparation of trans-4-[3-oxo-3,4-dihydro-2H-benzo[1,4]thiazine-6-carbonyl)-amino]-cyclohexanecarboxylic acid methyl ester 3-Oxo-3,4-dihydro-2H-benzo[1,4]thiazine-6-carboxylic acid (116 mg, 0.50 mmol, 1.0 eq) is added at room temperature to a stirred solution of trans-4-amino-cyclohexanecarboxylic acid methyl ester (80 mg, 0.50 mmol, 1.0 eq) in N,N-dimethylformamide (4 mL), followed by 1-hydroxybenzotriazole (74 mg, 0.55 mmol, 1.1 eq), N-(3-dimethylaminopropyl)-N'-ethylcarbodiimide hydrochloride (107 mg, 0.56 mmol, 1.15 eq) and N,N-diisopropylethylamine (192 μL, 1.12 mmol, 2.25 eq). After 15 hours stirring at room temperature, solvent is evaporated and the residue is extracted with dichloromethane (3×10 mL) and water (10 mL). The combined organic layers are dried over sodium sulfate, filtered and concentrated to afford trans-4-[(3-oxo-3,4-dihydro-2H-benzo[1,4]thiazine-6-carbonyl)-amino]-cyclohexanecarboxylic acid methyl ester as an off-white solid (127 mg, 66% yield).

MS m/z (+ESI): 349.2 [M+H]$^+$.

Preparation of 3-oxo-3,4-dihydro-2H-benzo[1,4]thiazine-6-carboxylic acid (trans-4-hydroxymethyl-cyclohexyl)-amide Lithium aluminium hydride (1.0 M solution in tetrahydrofuran, 0.66 mL, 0.66 mmol, 2.0 eq) is added at 0° C. to a stirred solution of trans-4-[(3-oxo-3,4-dihydro-2H-benzo[1,4]thiazine-6-carbonyl)-amino]-cyclohexanecarboxylic acid methyl ester (127 mg, 0.33 mmol, 1.0 eq) in tetrahydrofuran (2 mL). After 1 hour stirring at 0° C., the reaction mixture is cautiously quenched with ice-water (3 mL). Tetrahydrofuran is evaporated and the crude is extracted with ethyl acetate (3×10 mL) and water (10 mL). The combined organic layers are dried over sodium sulfate, filtered and concentrated to afford 3-oxo-3,4-dihydro-2H-benzo[1,4]thiazine-6-carboxylic acid (trans-4-hydroxymethyl-cyclohexyl)-amide as a yellow solid (47 mg, 40% yield).

MS m/z (+ESI): 321.2 [M+H]$^+$.

Preparation of 6-methoxy-quinoline-3-carboxylic acid trans-4-[(3-oxo-3,4-dihydro-2H-benzo[1,4]thiazine-6-carbonyl)-amino]-cyclohexylmethyl ester 6-Methoxy-quinoline-3-carboxylic acid (27 mg, 0.13 mmol, 1.0 eq) is added at room temperature to a stirred solution of 3-oxo-3,4-dihydro-2H-benzo[1,4]thiazine-6-carboxylic acid (trans-4-hydroxymethyl-cyclohexyl)-amide (47 mg, 0.13 mmol, 1.0 eq) in N,N-dimethylformamide (2 mL), followed by N-(3-dimethylaminopropyl)-N'-ethylcarbodiimide hydrochloride (28 mg, 0.15 mmol, 1.10 eq) and 4-(dimethylamino)pyridine (24 mg, 0.20 mmol, 1.50 eq). After 15 hours stirring at room temperature, solvent is evaporated and the residue is extracted with dichloromethane (3×10 mL) and water (10 mL). The combined organic layers are dried over sodium sulfate, filtered and concentrated to give a residue that is purified by preparative HPLC to afford 6-methoxy-quinoline-3-carboxylic acid trans-4-[(3-oxo-3,4-dihydro-2H-benzo[1,4]thiazine-6-carbonyl)-amino]-cyclohexylmethyl ester as a white solid (7 mg, 10% yield).

MS m/z (+ESI): 506.4 [M+H]$^+$.

Example 29

6-methoxy-[1,5]naphthyridine-3-carboxylic acid trans-4-[(2,3-dihydro-benzo[1,4]dioxin-6-ylmethyl)-amino]-cyclohexylmethyl ester

Preparation of trans-4-[(2,3-dihydro-benzo[1,4]dioxin-6-ylmethyl)-amino]-cyclohexanecarboxylic acid methyl ester 2,3-Dihydro-benzo[1,4]dioxine-6-carbaldehyde (198 mg, 1.21 mmol, 1.0 eq) is added at room temperature to a stirred solution of trans-4-amino-cyclohexanecarboxylic acid methyl ester (200 mg, 1.21 mmol, 1.0 eq) in 1,2-dichloroethane (8 mL) and methanol (2 mL), followed by acetic acid (80 μL, 1.39 mmol, 1.15 eq) and sodium cyanoborohydride (99 mg, 1.57 mmol, 1.3 eq). After 15 hours stirring at room temperature, the reaction mixture is extracted with dichloromethane (3×20 mL) and a saturated sodium hydrogen carbonate aqueous solution (20 mL). The combined organic layers are dried over sodium sulfate, filtered and concentrated to afford trans-4-[(2,3-dihydro-benzo[1,4]dioxin-6-ylmethyl)-amino]-cyclohexanecarboxylic acid methyl ester as an orange oil (359 mg, 92% yield).

MS m/z (+ESI): 306.2 [M+H]$^+$.

Preparation of {trans-4-[(2,3-dihydro-benzo[1,4]dioxin-6-ylmethyl)-amino]-cyclohexyl}-methanol Lithium aluminium hydride (1.0 M solution in tetrahydrofuran, 2.20 mL, 2.20 mmol, 2.0 eq) is added at 0° C. to a stirred solution of trans-4-[(2,3-dihydro-benzo[1,4]dioxin-6-ylmethyl)-amino]-cyclohexanecarboxylic acid methyl ester (355 mg, 1.10 mmol, 1.0 eq) in tetrahydrofuran (30 mL). After 2 hours stirring at 0° C., the reaction mixture is cautiously quenched with ice-water (6 mL). Tetrahydrofuran is evaporated and the crude is extracted with ethyl acetate (3×50 mL) and water (50 mL). The combined organic layers are dried over sodium sulfate, filtered and concentrated to afford {trans-4-[(2,3-dihydro-benzo[1,4]dioxin-6-ylmethyl)-amino]-cyclohexyl}-methanol as an orange oil (322 mg, 99% yield).

MS m/z (+ESI): 278.3 [M+H]$^+$.

Preparation of 6-methoxy-[1,5]naphthyridine-3-carboxylic acid trans-4-[(2,3-dihydro-benzo[1,4]dioxin-6-ylmethyl)-amino]-cyclohexylmethyl ester 6-Methoxy-[1,5]naphthyridine-3-carboxylic acid (100 mg, 0.44 mmol, 1.0 eq) is added at room temperature to a stirred solution of trans-{4-[(2,3-dihydro-benzo[1,4]dioxin-6-ylmethyl)-amino]-cyclohexyl}-methanol (129 mg, 0.44 mmol, 1.0 eq) in N,N-dimethylformamide (4 mL), followed by N-(3-dimethylaminopropyl)-N'-ethylcarbodiimide hydrochloride (93 mg, 0.48 mmol, 1.10 eq) and 4-(dimethylamino)pyridine (81 mg, 0.66 mmol, 1.50 eq). After 15 hours stirring at room temperature, solvent is evaporated and the residue is extracted with dichloromethane (3×10 mL) and water (10 mL). The combined organic layers are dried over sodium sulfate, filtered and concentrated to give a residue that is purified by preparative HPLC to afford 6-methoxy-[1,5]naphthyridine-3-carboxylic acid trans-4-[(2,3-dihydro-benzo[1,4]dioxin-6-ylmethyl)-amino]-cyclohexylmethyl ester as an off-white semisolid (33 mg, 15% yield).

$^1$H-NMR (400 MHz, DMSO-d$_6$) δ ppm: 9.22 (d, J=2.0 Hz, 1H), 8.60 (dd, J=0.7, 1.4 Hz, 1H), 8.37 (dd, J=0.7, 9.1 Hz, 1H), 8.29 (s, 1H), 7.42 (d, J=9.1 Hz, 1H), 6.85 (m, 3H), 4.20 (m, 6H), 4.07 (s, 3H), 3.73 (s, 2H), 2.43 (m, 1H), 2.02 (m, 2H), 1.87 (m, 2H), 1.78 (m, 1H), 1.05-1.25 (m, 4H).

MS m/z (+ESI): 464.4 [M+H]$^+$.

Example 30

6-methoxy-[1,5]naphthyridine-3-carboxylic acid trans-4-[(3-oxo-3,4-dihydro-2H-pyrido[3,2-b][1,4]oxazine-6-carbonyl)-amino]-cyclohexylmethyl ester The title compound is prepared as a light brown semisolid following Scheme 2 and in analogy to Example 28 using 3-oxo-3,4-dihydro-2H-pyrido[3,2-b][1,4]oxazine-6-carboxylic acid, trans-4-amino-cyclohexanecarboxylic acid methyl ester and 6-methoxy-[1,5]naphthyridine-3-carboxylic acid as starting materials.

MS m/z (+ESI): 492.4 [M+H]$^+$.

Example 31

6-methoxy-[1,5]naphthyridine-3-carboxylic acid trans-4-[2-(thiophen-2-ylsulfanyl)-ethylamino]-cyclohexylmethyl ester Preparation of 2-(2-bromo-ethylsulfanyl)-thiophene Potassium carbonate (2.50 g, 18.07 mmol, 2.1 eq) is added at room temperature to a stirred solution of thiophene-2-thiol (813 µL, 8.61 mmol, 1.0 eq) in 1,2-dibromoethane (10 mL) and the resulting mixture is stirred at 78° C. for 3 hours. Then potassium carbonate is removed by filtration and the mother liquid is concentrated to give a crude that is purified by column chromatography (silica gel, eluent: cyclohexane 100%) to afford 2-(2-bromo-ethylsulfanyl)-thiophene as a light yellow oil (1.86 g, 95% yield).

$^1$H-NMR (400 MHz, DMSO-d$_6$) δ ppm: 7.68 (dd, J=1.2, 5.3 Hz, 1H), 7.27 (dd, J=1.2, 3.5 Hz, 1H), 7.09 (dd, J=3.5, 5.3 Hz, 1H), 3.56 (m, 2H), 3.19 (m, 2H).

Preparation of trans-4-[2-(thiophen-2-ylsulfanyl)-ethylamino]-cyclohexanecarboxylic acid methyl ester 2-(2-Bromo-ethylsulfanyl)-thiophene (275 mg, 1.21 mmol, 1.0 eq) is added at room temperature to a stirred solution of trans-4-amino-cyclohexanecarboxylic acid methyl ester (200 mg, 1.21 mmol, 1.0 eq) in acetonitrile (6 mL). After 15 hours stirring at 100° C., the reaction mixture is evaporated to afford trans-4-[2-(thiophen-2-ylsulfanyl)-ethylamino]-cyclohexanecarboxylic acid methyl ester as an off-white oil (261 mg, 68% yield).

MS m/z (+ESI): 300.2 [M+H]$^+$.

Preparation of 6-methoxy-[1,5]naphthyridine-3-carboxylic acid trans-4-[2-(thiophen-2-ylsulfanyl)-ethylamino]-cyclohexylmethyl ester The title compound is prepared as an off-white viscous oil following Scheme 2 and in analogy to Example 28 using 6-methoxy-[1,5]naphthyridine-3-carboxylic acid and trans-4-[2-(thiophen-2-ylsulfanyl)-ethylamino]-cyclohexanecarboxylic acid methyl ester as starting materials.

$^1$H-NMR (400 MHz, DMSO-d$_6$) δ ppm: 9.23 (d, J=2.0 Hz, 1H), 8.59 (dd, J=0.7, 2.0 Hz, 1H), 8.38 (dd, J=0.7, 9.1 Hz, 1H), 8.25 (s, 1H), 7.62 (dd, J=1.2, 5.3 Hz, 1H), 7.42 (d, J=9.3 Hz, 1H), 7.20 (dd, J=1.2, 3.5 Hz, 1H), 7.05 (dd, J=3.5, 5.3 Hz, 1H), 4.20 (d, J=6.3 Hz, 2H), 4.06 (s, 3H), 2.75-2.90 (m, 4H), 2.42 (m, 1H), 1.72-1.97 (m, 5H), 0.92-1.18 (m, 4H).

MS m/z (+ESI): 458.3 [M+H]$^+$.

Example 32

6-methoxy-quinoline-3-carboxylic acid trans-4-[(2,3-dihydro-benzo[1,4]dioxin-6-ylmethyl)-methyl-amino]-cyclohexylmethyl ester Preparation of trans-4-[(2,3-dihydro-benzo[1,4]dioxin-6-ylmethyl)-methyl-amino]-cyclohexanecarboxylic acid methyl ester Potassium tert-butylate (35 mg, 0.31 mmol, 1.0 eq) is added at room temperature to a stirred solution of trans-4-[(2,3-dihydro-benzo[1,4]dioxin-6-ylmethyl)-amino]-cyclohexanecarboxylic acid methyl ester (100 mg, 0.31 mmol, 1.0 eq) in N,N-dimethylformamide (4 mL), followed by methyl iodide (10 μL, 0.16 mmol, 0.5 eq). After 15 hours stirring at room temperature methyl iodide (10 μL, 0.16 mmol, 0.5 eq) is added again. After 4 hours stirring at room temperature, solvent is evaporated and the residue is extracted with ethyl acetate (3×5 mL) and water (5 mL). The combined organic layers are washed with brine (5 mL), dried over sodium sulfate, filtered and concentrated to afford trans-4-[(2,3-dihydro-benzo[1,4]dioxin-6-ylmethyl)-methyl-amino]-cyclohexanecarboxylic acid methyl ester as a brown oil (1.60 g, 98% yield).

MS m/z (+ESI): 320.3 [M+H]$^+$, 334.3 [M+Na]$^+$.

Preparation of 6-methoxy-quinoline-3-carboxylic acid trans-4-[(2,3-dihydro-benzo[1,4]dioxin-6-ylmethyl)-methyl-amino]-cyclohexylmethyl ester The title compound is prepared as a yellow oil following Scheme 2 and in analogy to Example 28 using 6-methoxy-quinoline-3-carboxylic acid and trans-4-[(2,3-dihydro-benzo[1,4]dioxin-6-ylmethyl)-methyl-amino]-cyclohexanecarboxylic acid methyl ester as starting materials.

MS m/z (+ESI): 477.4 [M+H]$^+$.

Example 33

6-methoxy-quinoline-3-carboxylic acid trans-4-[(2,3-dihydro-benzo[1,4]dioxin-6-ylmethyl)-amino]-cyclohexylmethyl ester The title compound is prepared as an off-white semisolid (24 mg, 26% yield) following Scheme 2 and in analogy to Example 28 using 6-methoxy-quinoline-3-carboxylic acid (40 mg, 0.19 mmol, 1.0 eq) and {trans-4-[(2,3-dihydro-benzo[1,4]dioxin-6-ylmethyl)-amino]-cyclohexyl}-methanol (55 mg, 0.19 mmol, 1.0 eq) as starting materials.

Alternative Procedure

Preparation of 6-methoxy-quinoline-3-carboxylic acid trans-4-tert-butoxycarbonylamino-cyclohexylmethyl ester trans-(4-Hydroxymethyl-cyclohexyl)-carbamic acid tert-butyl ester (480 mg, 2.46 mmol, 1.0 eq) is added at room temperature to a stirred solution of 6-methoxy-quinoline-3-carboxylic acid (564 mg, 2.46 mmol, 1.0 eq) in dichloromethane (15 mL), followed by 1-hydroxybenzotriazole (532 mg, 3.94 mmol, 1.6 eq), N-(3-dimethylaminopropyl)-N'-ethylcarbodiimide hydrochloride (1.04 g, 5.41 mmol, 2.2 eq) and triethylamine (754 μL, 5.41 mmol, 2.2 eq). After 15 hours stirring at 30° C., solvent is evaporated and the residue is purified by column chromatography (silica gel, eluent: petroleum ether:ethyl acetate, 4:1, v/v) to afford 6-methoxy-quinoline-3-carboxylic acid trans-4-tert-butoxycarbonylamino-cyclohexylmethyl ester as a white powder (787 mg, 77% yield).

$^1$H-NMR (400 MHz, CDCl$_3$,) δ ppm: 9.29 (s, 1H), 8.74 (s, 1H), 8.10 (d, J=8.8 Hz, 1H), 7.50 (dd, J=2.8, 8.8 Hz, 1H), 7.20 (d, J=2.8 Hz, 1H), 4.24 (d, J=6.4 Hz, 2H), 3.97 (s, 3H), 3.39-3.48 (m, 1H), 2.07-2.11 (m, 2H), 1.92-1.96 (m, 2H), 1.61-1.80 (m, 1H), 1.45 (s, 9H), 1.11-1.25 (m, 4H).

MS m/z (+ESI): 415.2 [M+H]$^+$.

Preparation of the trifluoroacetic acid salt of 6-methoxy-quinoline-3-carboxylic acid trans-4-amino-cyclohexylmethyl ester Trifluoroacetic acid (1.45 mL, 18.82 mmol, 10.0 eq) is added at 0° C. to a stirred solution of 6-methoxy-quinoline-3-carboxylic acid trans-4-tert-butoxycarbonylamino-cyclohexylmethyl ester (780 mg, 1.88 mmol, 1.0 eq) in dichloromethane (10 mL). After 5 hours stirring at room temperature, the reaction mixture is concentrated to give a crude product that is triturated in diethyl ether to afford the trifluoroacetic acid salt of 6-methoxy-quinoline-3-carboxylic acid trans-4-amino-cyclohexylmethyl ester as an off-white powder (800 mg, 98% yield).

$^1$H-NMR (400 MHz, DMSO-d$_6$, D$_2$O) δ ppm: 9.11 (s, 1H), 8.89 (s, 1H), 7.98 (d, J=8.0 Hz, 1H), 7.56 (s, 1H), 7.55 (d, J=8.0 Hz, 1H), 4.18 (d, J=5.6 Hz), 3.82 (s, 3H), 2.90-2.97 (m, 1H), 1.85-1.96 (m, 4H), 1.73-7.78 (m, 1H), 1.14-1.32 (m, 4H).

MS m/z (+ESI): 315.2 [M+H]$^+$.

Preparation of 6-methoxy-quinoline-3-carboxylic acid trans-4-[(2,3-dihydro-benzo[1,4]dioxin-6-ylmethyl)-amino]-cyclohexylmethyl ester 2,3-Dihydro-benzo[1,4]dioxine-6-carbaldehyde (188 mg, 1.14 mmol, 1.8 eq) is added at room temperature to a stirred solution of the trifluoroacetic acid salt of 6-methoxy-quinoline-3-carboxylic acid trans-4-amino-cyclohexylmethyl ester (200 mg, 0.64 mmol, 1.0 eq) in 1,2-dichloroethane (10 mL), followed by sodium triacetoxyborohydride (1.35 g, 6.36 mmol, 10.0 eq). After 18 hours stirring at room temperature, the reaction mixture is extracted with dichloromethane (3×10 mL) and a saturated sodium hydrogen carbonate aqueous solution (10 mL). The combined organic layers are dried over sodium sulfate, filtered and concentrated to give a residue that is purified by preparative HPLC to afford 6-methoxy-quinoline-3-carboxylic acid trans-4-[(2,3-dihydro-benzo[1,4]dioxin-6-ylmethyl)-amino]-cyclohexylmethyl ester as a white powder (123 mg, 40% yield).

$^1$H-NMR (400 MHz, DMSO-d$_6$) δ ppm: 9.14 (s, 1H), 8.87 (s, 1H), 8.00 (d, J=9.2 Hz, 1H), 7.64 (d, J=2.8 Hz, 1H), 7.54 (dd, J=2.8, 9.2 Hz, 1H), 6.87 (s, 1H), 6.77 (m, 2H), 4.17 (m, 6H), 3.90 (s, 3H), 3.72 (s, 2H), 2.48 (m, 1H), 1.84-2.02 (m, 4H), 1.73 (m, 1H), 1.12 (m, 4H).

MS m/z (+ESI): 463.2 [M+H]$^+$.

Example 34

6-methoxy-quinoline-3-carboxylic acid trans-4-[(2,3-dihydro-benzo[1,4]dioxin-6-ylmethyl)-ethyl-amino]-cyclohexylmethyl ester Ethyl iodide (51 μL, 0.63 mmol, 8.0 eq) is added at room temperature to a stirred solution of 6-methoxy-quinoline-3-carboxylic acid trans-4-[(2,3-dihydro-benzo[1,4]dioxin-6-ylmethyl)-amino]-cyclohexylmethyl ester (37 mg, 0.08 mmol, 1.0 eq) in N,N-dimethylformamide (0.5 mL), followed by silver oxide (73 mg, 0.31 mmol, 4.0 eq). After 4 hours stirring at room temperature, the reaction mixture is filtered through decalite and the mother liquid is concentrated to give a residue that is purified by preparative HPLC to afford 6-methoxy-quinoline-3-carboxylic acid trans-4-[(2,3-dihydro-benzo[1,4]dioxin-6-ylmethyl)-ethyl-amino]-cyclohexylmethyl ester as an off-white lyophilized solid (9 mg, 14% yield)

$^1$H-NMR (400 MHz, DMSO-d$_6$) δ ppm: 9.15 (s, 1H), 8.89 (s, 1H), 8.01 (d, J=9.2 Hz, 1H), 7.66 (d, J=2.8 Hz, 1H), 7.56 (dd, J=2.8, 9.2 Hz, 1H), 6.81 (s, 1H), 6.76 (m, 2H), 4.17-4.21 (m, 6H), 3.93 (s, 3H), 3.47 (s, 2H), 3.30 (m, 2H), 2.48 (m, 1H), 1.78-1.95 (m, 4H), 1.73 (m, 1H), 1.33 (m, 2H), 1.08 (m, 2H), 0.93 (t, J=7.1 Hz, 3H).

MS m/z (+ESI): 491.4 ([M+H]$^+$.

Example 35

5-thiophen-2-yl-isoxazole-3-carboxylic acid {1-[2-(7-methoxy-quinoxalin-2-ylsulfanyl)-ethyl]-piperidin-4-yl}-amide

Preparation of 2-(7-methoxy-quinoxalin-2-ylsulfanyl)-ethanol

2-Mercaptoethanol (2.5 g, 32.06 mmol, 1.2 eq) is added at room temperature to a stirred solution of 2-chloro-7-methoxy-quinoxaline (5.2 g, 26.72 mmol, 1.0 eq) in N,N-dimethylformamide (160 mL), followed by potassium carbonate (7.4 g, 53.44 mol, 2.0 eq). After 15 hours stirring at room temperature, solvent is evaporated and the residue is extracted with ethyl acetate (3×150 mL) and water (100 mL). The combined organic layers are dried over sodium sulfate, filtered and concentrated to give a crude product that is purified by column chromatography (silica gel, eluent: ethyl acetate:hexane, 1:2, v/v) to afford 2-(7-methoxy-quinoxalin-2-ylsulfanyl)-ethanol as a pale yellow solid (6.22 g, 99% yield).

$^1$H-NMR (400 MHz, DMSO-d$_6$) δ ppm: 8.57 (s, 1H), 7.84 (d, J=9.2 Hz, 1H), 7.28 (dd, J=2.4, 9.2 Hz, 1H), 7.24 (d, J=2.4 Hz, 1H), 5.05 (m, 1H), 3.91 (s, 3H), 3.69 (m, 2H), 3.38 (m, 2H).

MS m/z (+ESI): 236.9 [M+H]$^+$.

Preparation of (7-methoxy-quinoxalin-2-ylsulfanyl)-acetaldehyde

Dess-Martin periodinane (10.8 g, 25.4 mmol, 2.0 eq) is added at 0° C. to a stirred solution of 2-(7-methoxy-quinoxalin-2-ylsulfanyl)-ethanol (3.0 g, 12.7 mmol, 1.0 eq) in dichloromethane (100 mL). The reaction mixture is stirred 0° C. for 30 minutes then at room temperature for 3 hours. Then a saturated sodium thiosulfate aqueous solution (50 mL) is added, followed by a saturated sodium hydrogen carbonate aqueous solution (50 mL). The resulting mixture is stirred for 30 minutes, then extracted with dichloromethane (3×100 mL). The combined organic layers are dried over sodium sulfate, filtered and concentrated to give a crude product that is purified by column chromatography (silica gel, eluent: ethyl acetate:hexane, 1:5, v/v) to afford (7-methoxy-quinoxalin-2-ylsulfanyl)-acetaldehyde as a yellow oil (2.22 g, 75% yield).

$^1$H NMR (400 MHz, Acetone-d$_6$) δ ppm: 9.72 (s, 1H), 8.65 (s, 1H), 7.89 (d, J=9.2 Hz, 1H), 7.29 (dd, J=2.4, 9.2 Hz, 1H, 7.25 (d, J=2.4 Hz, 1H), 4.15 (s, 2H), 3.99 (s, 3H).

MS m/z (+ESI): 235.1 [M+H]$^+$.

Preparation of {1-[2-(7-methoxy-quinoxalin-2-ylsulfanyl)-ethyl]-piperidin-4-yl}-carbamic acid tert-butyl ester Piperidin-4-yl-carbamic acid tert-butyl ester (2.82 g, 14.09 mmol, 1.5 eq) is added at room temperature to a stirred solution of (7-methoxy-quinoxalin-2-ylsulfanyl)-acetaldehyde (2.2 g, 9.39 mmol, 1.0 eq) in 1,2-dichloroethane (80 mL), followed by sodium triacetoxyborohydride (3.98 g, 18.78 mmol, 2.0 eq). After 15 hours stirring at room temperature, the reaction mixture is extracted with dichloromethane (3×60 mL) and a saturated sodium hydrogen carbonate aqueous solution (60 mL). The combined organic layers are dried over sodium sulfate, filtered and concentrated to give a crude product that is purified by column chromatography (silica gel, eluent: ethyl acetate:hexane, 1:1, v/v) to give a yellow solid that is further recrystallized with ethyl acetate:hexane (1:6, v/v) to afford {1-[2-(7-methoxy-quinoxalin-2-ylsulfanyl)-ethyl]-piperidin-4-yl}-carbamic acid tert-butyl ester as light yellow needles (2.6 g, 66% yield).

$^1$H-NMR (400 MHz, DMSO-d$_6$) δ ppm: 8.58 (s, 1H), 7.86 (d, J=9.2 Hz, 1H), 7.30 (dd, J=2.1, 9.6 Hz, 1H), 7.24 (d, J=2.4 Hz, 1H), 6.71 (br, 1H), 3.91 (s, 3H), 3.42 (m, 2H), 3.20 (m, 1H), 2.89 (m, 2H), 2.63 (m, 2H), 2.03 (m, 2H), 1.67 (m, 2H), 1.37 (m, 2H), 1.30 (s, 9H).

MS m/z (+ESI): 419.0 [M+H]$^+$.

Preparation of 1-[2-(7-methoxy-quinoxalin-2-ylsulfanyl)-ethyl]-piperidin-4-ylamine Trifluoroacetic acid (5.41 mL, 70.2 mmol, 15.0 eq) is added at 0° C. to a stirred solution of {1-[2-(7-methoxy-quinoxalin-2-ylsulfanyl)-ethyl]-piperidin-4-yl}-carbamic acid tert-butyl ester (2.0 g, 4.68 mmol, 1.0 eq) in dichloromethane (200 mL). After 15 hours stirring at room temperature, the reaction mixture is extracted with dichloromethane (3×50 mL) and water (50 mL) and the pH value adjusted to 12 by the addition of a 1N sodium hydroxide aqueous solution. The combined organic layers are dried over sodium sulfate, filtered and concentrated to afford 1-[2-(7-methoxy-quinoxalin-2-ylsulfanyl)-ethyl]-piperidin-4-ylamine as an orange oil (1.40 g, 92% yield).

$^1$H-NMR (400 MHz, DMSO-d$_6$) δ ppm: 8.61 (s, 1H), 7.90 (d, J=9.1 Hz, 1H), 7.34 (dd, J=2.8, 9.1 Hz, 1H), 7.28 (d, J=2.8 Hz, 1H), 3.94 (s, 3H), 3.44 (t, J=7.0 Hz, 2H), 2.88 (m, 2H), 2.64 (t, J=7.0 Hz, 2H), 2.05 (m, 2H), 1.68 (m, 2H), 1.48 (br, 1H), 1.22 (m, 2H).

MS m/z (+ESI): 319.3 [M+H]$^+$.

Preparation of 5-thiophen-2-yl-isoxazole-3-carboxylic acid {1-[2-(7-methoxy-quinoxalin-2-ylsulfanyl)-ethyl]-piperidin-4-yl}-amide 5-Thiophen-2-yl-isoxazole-3-carboxylic acid (43 mg, 0.22 mmol, 1.0 eq) is added at room temperature to a stirred solution of 1-[2-(7-methoxy-quinoxalin-2-ylsulfanyl)-ethyl]-piperidin-4-ylamine (70 mg, 0.22 mmol, 1.0 eq) in N,N-dimethylformamide (5 mL), followed by 1-hydroxybenzotriazole (32 mg, 0.24 mmol, 1.1 eq), N-(3-dimethylaminopropyl)-N'-ethylcarbodiimide hydrochloride (47 mg, 0.25 mmol, 1.15 eq) and N,N-diisopropylethylamine (83 µL, 0.48 mmol, 2.25 eq). After 15 hours stirring at room temperature, solvent is evaporated and the residue is extracted with dichloromethane (3×10 mL) and water (10 mL). The combined organic layers are dried over sodium sulfate, filtered and concentrated to give a residue that is purified by preparative HPLC to afford 5-thiophen-2-yl-isoxazole-3-carboxylic acid {1-[2-(7-methoxy-quinoxalin-2-ylsulfanyl)-ethyl]-piperidin-4-yl}-amide as an orange solid (15 mg, 13% yield).

$^1$H-NMR (400 MHz, DMSO-d$_6$) δ ppm: 8.73 (d, J=8.1 Hz, 1H), 8.62 (s, 1H), 7.88 (m, 2H), 7.79 (d, J=1.1 Hz, 1H), 7.34 (dd, J=2.8, 9.1 Hz, 1H), 7.28 (m, 2H), 7.19 (s, 1H), 3.94 (s, 3H), 3.78 (m, 1H), 3.48 (t, J=7.0 Hz, 2H), 3.01 (m, 2H), 2.70 (t, J=7.0 Hz, 2H), 2.12 (m, 2H), 1.78 (m, 2H), 1.62 (m, 2H).

MS m/z (+ESI): 496.2 [M+H]$^+$.

Example 36

3-oxo-3,4-dihydro-2H-benzo[1,4]oxazine-6-carboxylic acid {1-[2-(7-methoxy-quinoxalin-2-ylsulfanyl)-ethyl]-piperidin-4-yl}-amide The title compound is prepared as an off-white solid (42 mg, 38% yield) following Scheme 3 and in analogy to Example 35 using 3-oxo-3,4-dihydro-2H-benzo[1,4]oxazine-6-carboxylic acid (42 mg, 0.22 mmol 1.0 eq) and 1-[2-(7-methoxy-quinoxalin-2-ylsulfanyl)-ethyl]-piperidin-4-ylamine (70 mg, 0.22 mmol, 1.0 eq) as starting materials.

$^{1}$H-NMR (400 MHz, DMSO-d$_6$) δ ppm: 10.81 (s, 1H), 8.62 (s, 1H), 8.16 (d, J=7.8 Hz, 1H), 7.90 (d, J=9.1 Hz, 1H), 7.28-7.45 (m, 4H), 6.98 (d, J=8.5 Hz, 1H), 4.63 (s, 2H), 3.94 (s, 3H), 3.77 (m, 1H), 3.48 (t, J=7.0 Hz, 2H), 3.01 (m, 2H), 2.72 (t, J=7.0 Hz, 2H), 2.14 (m, 2H), 1.78 (m, 2H), 1.57 (m, 2H).

MS m/z (+ESI): 494.2 [M+H]$^+$.

Example 37

7-chloro-3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-amide The title compound is prepared as an off-white solid (42 mg, 60% yield) following Scheme 3 and in analogy to Example 35 using 7-chloro-3-oxo-3,4-dihydro-2H-benzo[1,4]thiazine-6-carboxylic acid (31 mg, 0.12 mmol 1.0 eq) and 1-[2-(7-methoxy-quinoxalin-2-ylsulfanyl)-ethyl]-piperidin-4-ylamine (40 mg, 0.12 mmol, 1.0 eq) as starting materials.

$^{1}$H-NMR (400 MHz, DMSO-d$_6$) δ ppm: 10.73 (s, 1H), 8.62 (s, 1H), 8.38 (d, J=7.8 Hz, 1H), 7.90 (d, J=9.1 Hz, 1H), 7.50 (s, 1H), 7.35 (dd, J=2.8, 9.1 Hz, 1H), 7.28 (d, J=2.8 Hz, 1H), 6.94 (s, 1H), 3.94 (s, 3H), 3.75 (m, 1H), 3.51 (s, 2H), 3.48 (t, J=7.0 Hz, 2H), 3.01 (m, 2H), 2.72 (m, 2H), 2.21 (m, 2H), 1.81 (m, 2H), 1.50 (m, 2H).

MS m/z (+ESI): 544.2 [M+H]$^+$.

Example 38

{1-[2-(7-methoxy-quinoxalin-2-ylsulfanyl)-ethyl]-piperidin-4-yl}-[2-(thiophen-2-ylsulfanyl)-ethyl]-amine 2-(2-Bromo-ethylsulfanyl)-thiophene (51 mg, 0.22 mmol, 1.0 eq) is added at room temperature to a stirred solution of 1-[2-(7-methoxy-quinoxalin-2-ysulfanyl)-ethyl]-piperidin-4-ylamine (70 mg, 0.22 mmol, 1.0 eq) in acetonitrile (5 mL). After 15 hours stirring at 90° C. the reaction mixture is concentrated to give a residue that is purified by preparative HPLC to afford {1-[2-(7-methoxy-quinoxalin-2-ylsulfanyl)-ethyl]-piperidin-4-yl}-[2-(thiophen-2-ylsulfanyl)-ethyl]-amine as a brown waxy solid (19 mg, 20% yield).

$^{1}$H-NMR (400 MHz, DMSO-d$_6$) δ ppm: 8.61 (s, 1H), 7.90 (d, J=9.1 Hz, 1H), 7.66 (dd, J=1.2, 5.5 Hz, 1H), 7.34 (dd, J=2.8, 9.1 Hz, 1H), 7.25 (m, 2H), 7.07 (dd, J=3.5, 5.3 Hz, 1H), 3.94 (s, 3H), 3.45 (t, J=6.8 Hz, 2H), 2.92 (m, 6H), 2.68 (m, 3H), 2.07 (m, 2H), 1.80 (m, 2H), 1.32 (m, 2H).

MS m/z (+ESI): 461.2 [M+H]$^+$.

Example 39

2,3-dihydro-benzo[1,4]dioxine-6-carboxylic acid {1-[2-(7-methoxy-quinoxalin-2-ylsulfanyl)-ethyl]-piperidin-4-yl}-amide The title compound is prepared as a yellow solid (61 mg, 56% yield) following Scheme 3 and in analogy to Example 35 using 2,3-dihydro-benzo[1,4]dioxine-6-carboxylic acid (39 mg, 0.22 mmol 1.0 eq) and 1-[2-(7-methoxy-quinoxalin-2-ylsulfanyl)-ethyl]-piperidin-4-ylamine (70 mg, 0.22 mmol, 1.0 eq) as starting materials.

$^{1}$H-NMR (400 MHz, DMSO-d$_6$) δ ppm: 8.62 (s, 1H), 8.06 (d, J=7.8 Hz, 1H), 7.90 (d, J=9.1 Hz, 1H), 7.28-7.39 (m, 4H), 6.90 (d, J=8.3 Hz, 1H), 4.28 (m, 4H), 3.92 (s, 3H), 3.77 (m, 1H), 3.48 (t, J=7.0 Hz, 2H), 2.01 (m, 2H), 2.70 (t, J=7.0 Hz, 2H), 2.12 (m, 2H), 1.78 (m, 2H), 1.57 (m, 2H).

MS m/z (+ESI): 481.2 [M+H]$^+$.

Example 40

6-({1-[2-(7-methoxy-quinoxalin-2-ylsulfanyl)-ethyl]-piperidin-4-yl}-amino)-methyl)-4H-benzo[1,4]oxazin-3-one 3-Oxo-3,4-dihydro-2H-benzo[1,4]oxazine-6-carbaldehyde (354 mg, 2.00 mmol, 1.0 eq) is added at room temperature to a stirred solution of 1-[2-(7-methoxy-quinoxalin-2-ylsulfanyl)-ethyl]-piperidin-4-ylamine (0.65 g, 2.00 mmol, 1.0 eq) in 1,2-dichloroethane (4 mL) and methanol (1 mL), followed by acetic acid (0.11 mL, 2.00 mmol, 1.0 eq) and sodium cyanoborohydride (160 mg, 2.6 mmol, 1.4 eq). After 15 hours stirring at room temperature, the reaction mixture is extracted with dichloromethane (3×20 mL) and a saturated sodium hydrogen carbonate aqueous solution (20 mL). The combined organic layers are dried over sodium sulfate, filtered and concentrated to give a residue that is purified by preparative HPLC to afford 6-({1-[2-(7-methoxy-quinoxalin-2-ylsulfanyl)-ethyl]-piperidin-4-yl}-amino)-methyl)-4H-benzo[1,4]oxazin-3-one as a white solid (500 mg, 52% yield).

$^{1}$H-NMR (400 MHz, DMSO-d$_6$) δ ppm: 10.60 (br, 1H), 8.58 (s, 1H), 7.86 (d, J=9.2 Hz, 1H), 7.30 (dd, J=2.8, 9.2 Hz, 1H), 7.24 (d, J=2.4 Hz, 1H), 6.85 (m, 3H), 4.50 (s, 2H), 3.91 (s, 3H), 3.60 (s, 2H), 3.42 (m, 2H), 2.87 (m, 2H), 2.62 (m, 2H), 2.34 (s, 1H), 2.00 (m, 2H), 1.77 (m, 2H), 1.24 (m, 2H).

MS m/z (+ESI): 480.1 [M+H]$^+$.

Example 41

(2,3-dihydro-benzo[1,4]dioxin-6-ylmethyl)-{1-[2-(7-methoxy-quinoxalin-2-ylsulfanyl)-ethyl]-piperidin-4-yl}-amine The title compound is prepared as a light yellow oil (2.03 g, 78% yield) following Scheme 3 and in analogy to Example 40 using 2,3-dihydro-benzo[1,4]dioxine-6-carbaldehyde (792 mg, 4.77 mmol 1.0 eq) and 1-[2-(7-methoxy-quinoxalin-2-ylsulfanyl)-ethyl]-piperidin-4-ylamine (1.52 g, 4.77 mmol, 1.0 eq) as starting materials.

$^{1}$H-NMR (400 MHz, DMSO-d$_6$) δ ppm: 8.58 (s, 1H), 7.85 (d, J=9.2 Hz, 1H), 7.30 (d, J=8.8 Hz, 1H), 7.24 (s, 1H), 6.75 (m, 3H), 4.17 (s, 4H), 3.90 (s, 3H), 3.55 (s, 2H), 3.36 (m, 2H), 2.85 (m, 2H), 2.55 (m, 2H), 2.31 (m, 1H), 1.97 (m, 2H), 1.74 (m, 2H), 1.20 (m, 2H).

MS m/z (+ESI): 467.1 [M+H]$^+$.

Example 42

{1-[2-(7-methoxy-quinoxalin-2-ylsulfanyl)-ethyl]-piperidin-4-yl}-(5-thiophen-2-yl-isoxazol-3-ylmethyl)-amine The title compound is prepared as a yellow oil (57 mg, 52% yield) following Scheme 3 and in analogy to Example 40 using 5-thiophen-2-yl-isoxazole-3-carbaldehyde (43 mg, 0.22 mmol 1.0 eq) and 1-[2-(7-methoxy-quinoxalin-2-ylsulfanyl)-ethyl]-piperidin-4-ylamine (70 mg, 0.22 mmol, 1.0 eq) as starting materials.

¹H-NMR (400 MHz, DMSO-d6) δ ppm: 8.61 (s, 1H), 7.89 (d, J=9.1 Hz, 1H), 7.80 (dd, J=1.1, 5.0 Hz, 1H), 7.68 (dd, J=1.1, 3.6 Hz, 1H), 7.34 (dd, J=2.8, 9.1 Hz, 1H), 7.25 (m, 2H), 6.83 (s, 1H), 3.93 (s, 3H), 3.78 (s, 2H), 3.46 (t, J=6.8 Hz, 2H), 2.92 (m, 2H), 2.78 (t, J=6.8 Hz, 2H), 2.41 (m, 1H), 2.06 (m, 2H), 1.81 (m, 2H), 1.28 (m, 2H).
MS m/z (+ESI): 482.2 [M+H]⁺.

Example 43

(2,3-dihydro-benzo[1,4]dioxin-6-ylmethyl)-{1-[2-(7-methoxy-quinoxalin-2-ylsulfanyl)-ethyl]-piperidin-4-yl}-methyl-amine The title compound is prepared as a yellow foam (30 mg, 29% yield) following Scheme 3 and in analogy to Example 40 using paraformaldehyde (37 mg, 0.64 mmol 3.0 eq) and (2,3-dihydro-benzo[1,4]dioxin-6-ylmethyl)-{1-[2-(7-methoxy-quinoxalin-2-ylsulfanyl)-ethyl]-piperidin-4-yl}-amine (100 mg, 0.22 mmol, 1.0 eq) as starting materials.
¹H-NMR (400 MHz, MeOH-d4) δ ppm: 8.47 (s, 1H), 7.85 (d, J=9.2 Hz, 1H), 7.32 (m, 2H), 6.90 (m, 3H), 4.62 (s, 3H), 4.25 (s, 4H), 3.97 (m, 5H), 3.53 (m, 2H), 2.85 (m, 2H), 2.52 (s, 3H), 2.29 (m, 2H), 2.04 (m, 2H), 1.80 (m, 2H).
MS m/z (+ESI): 481.5 [M+H]⁺.

Example 44

7-chloro-3,4-dihydro-2H-benzo[1,4]thiazine-6-carboxylic acid {1-[2-(7-methoxy-quinoxalin-2-ylsulfanyl)-ethyl]-piperidin-4-yl}-amide The title compound is prepared as an off-white solid (37 mg, 51% yield) following Scheme 3 and in analogy to Example 35 using 7-chloro-3,4-dihydro-2H-benzo[1,4]thiazine-6-carboxylic acid (29 mg, 0.12 mmol 1.0 eq) and 1-[2-(7-methoxy-quinoxalin-2-ylsulfanyl)-ethyl]-piperidin-4-ylamine as starting materials.
¹H-NMR (400 MHz, DMSO-d6) δ ppm: 8.62 (s, 1H), 8.17 (d, J=7.9 Hz, 1H), 7.92 (d, J=9.1 Hz, 1H), 7.34 (dd, J=2.8, 9.1 Hz, 1H), 7.28 (d, J=2.8 Hz, 1H), 6.94 (s, 1H), 6.51 (s, 1H), 6.38 (s, 1H), 3.94 (s, 3H), 3.69 (m, 1H), 3.48 (m, 4H), 2.98 (m, 4H), 2.69 (t, J=7.0 Hz, 2H), 2.15 (m, 2H), 1.77 (m, 2H), 1.49 (m, 2H).
MS m/z (+ESI): 530.2 [M+H]⁺.

Example 45

6-({1-[2-(7-methoxy-quinoxalin-2-ylsulfanyl)-ethyl]-piperidin-4-ylamino}-methyl)-4H-pyrido[3,2-b][1,4]oxazin-3-one The title compound is prepared as a yellow solid (48 mg, 44% yield) following Scheme 3 and in analogy to Example 40 using 3-oxo-3,4-dihydro-2H-pyrido[3,2-b][1,4]oxazine-6-carbaldehyde (40 mg, 0.22 mmol 1.0 eq) and 1-[2-(7-methoxy-quinoxalin-2-ylsulfanyl)-ethyl]-piperidin-4-ylamine (70 mg, 0.22 mmol, 1.0 eq) as starting materials.
¹H-NMR (400 MHz, DMSO-d6) δ ppm: 11.20 (br, 1H), 8.61 (s, 1H), 7.90 (d, J=9.1 Hz, 1H), 7.32 (m, 3H), 7.02 (d, J=8.1 Hz, 1H), 4.61 (s, 2H), 3.94 (s, 3H), 3.73 (s, 2H), 3.44 (t, J=7.0 Hz, 2H), 2.92 (m, 2H), 2.67 (t, J=7.0 Hz, 2H), 2.45 (m, 1H), 2.05 (m, 2H), 1.81 (m, 2H), 1.30 (m, 2H).
MS m/z (+ESI): 481.3 [M+H]⁺.

Example 46

6-({1-[2-(7-methoxy-quinoxalin-2-ylsulfanyl)-ethyl]-piperidin-4-ylamino}-methyl)-4H-benzo[1,4]thiazin-3-one The title compound is prepared as a yellow waxy solid (54 mg, 48% yield) following Scheme 3 and in analogy to Example 40 using 3-oxo-3,4-dihydro-2H-benzo[1,4]thiazine-6-carbaldehyde (42 mg, 0.22 mmol 1.0 eq) and 1-[2-(7-methoxy-quinoxalin-2-ylsulfanyl)-ethyl]-piperidin-4-ylamine (70 mg, 0.22 mmol, 1.0 eq) as starting materials.
¹H-NMR (400 MHz, DMSO-d6) δ ppm: 10.53 (s, 1H), 8.61 (s, 1H), 7.90 (d, J=9.1 Hz, 1H), 7.34 (dd, J=2.8, 9.1 Hz, 1H), 7.27 (d, J=2.8 Hz, 1H), 7.24 (d, J=7.8 Hz, 1H), 6.96 (m, 2H), 3.94 (s, 3H), 3.68 (s, 2H), 3.45 (m, 4H), 2.92 (m, 2H), 2.66 (t, J=7.0 Hz, 2H), 2.45 (m, 1H), 2.03 (m, 2H), 1.82 (m, 2H), 1.29 (m, 2H).
MS m/z (+ESI): 496.2 [M+H]⁺.

Example 47

(2,3-dihydro-benzo[1,4]dioxin-6-ylmethyl)-ethyl-{1-[2-(7-methoxy-quinoxalin-2-ylsulfanyl)-ethyl]-piperidin-4-yl}-amine The title compound is prepared as a yellow solid (67 mg, 20% yield) following Scheme 3 and in analogy to Example 40 using acetaldehyde (181 µg, 3.21 mmol 5.0 eq) and (2,3-dihydro-benzo[1,4]dioxin-6-ylmethyl)-{1-[2-(7-methoxy-quinoxalin-2-ylsulfanyl)-ethyl]-piperidin-4-yl}-amine (300 mg, 0.64 mmol, 1.0 eq) as starting materials.
¹H-NMR (400 MHz, MeOH-d4) δ ppm: 8.46 (s, 1H), 7.83 (d, J=8.8 Hz, 1H), 6.75-6.84 (m, 3H), 7.30 (m, 2H), 4.23 (s, 4H), 3.97 (s, 3H), 3.63 (s, 2H), 3.48 (m, 2H), 3.17 (m, 2H), 2.68-2.78 (m, 5H), 2.15 (m, 2H), 1.84 (m, 2H), 1.65 (m, 2H), 1.05 (m, 3H).
MS m/z (+ESI): 495.6 [M+H]⁺.

Example 48

7-chloro-6-({1-[2-(7-methoxy-quinoxalin-2-ylsulfanyl)-ethyl]-piperidin-4-ylamino}-methyl)-4H-benzo[1,4]thiazin-3-one The title compound is prepared as a yellow solid (24 mg, 35% yield) following Scheme 3 and in analogy to Example 40 using 7-chloro-3-oxo-3,4-dihydro-2H-benzo[1,4]thiazine-6-carbaldehyde (30 mg, 0.12 mmol 1.0 eq) and 1-[2-(7-methoxy-quinoxalin-2-ylsulfanyl)-ethyl]-piperidin-4-ylamine (40 mg, 0.12 mmol, 1.0 eq) as starting materials.
¹H-NMR (400 MHz, DMSO-d6) δ ppm: 10.63 (br, 1H), 8.61 (s, 1H), 7.90 (d, J=9.1 Hz, 1H), 7.38 (s, 1H), 7.34 (dd, J=2.8, 9.1 Hz, 1H), 7.27 (d, J=2.8 Hz, 1H), 7.21 (s, 1H), 3.94 (s, 3H), 3.71 (s, 2H), 3.45 (m, 4H), 2.92 (m, 2H), 2.68 (m, 2H), 2.40 (m, 1H), 2.05 (m, 2H), 1.82 (m, 2H), 1.29 (m, 2H).
MS m/z (+ESI): 530.2 [M+H]⁺.

Example 49

(7-chloro-3,4-dihydro-2H-benzo[1,4]thiazin-6-ylmethyl)-{1-[2-(7-methoxy-quinoxalin-2-ylsulfanyl)-ethyl]-piperidin-4-yl}-amine The title compound is prepared as a yellow waxy solid (23 mg, 34% yield) following Scheme 3 and in analogy to Example 40 using 7-chloro-3,4-dihydro-2H-benzo[1,4]thiazine-6-carbaldehyde (27 mg, 0.12 mmol 1.0 eq) and 1-[2-(7-methoxy-quinoxalin-2-ylsulfanyl)-ethyl]-piperidin-4-ylamine (40 mg, 0.12 mmol, 1.0 eq) as starting materials.

$^1$H-NMR (400 MHz, DMSO-d$_6$) δ ppm: 8.61 (s, 1H), 7.90 (d, J=9.1 Hz, 1H), 7.34 (dd, J=2.8, 9.1 Hz, 1H), 7.28 (d, J=2.8 Hz, 1H), 6.86 (s, 1H), 6.68 (s, 1H), 6.21 (br, 1H), 3.94 (s, 3H), 3.62 (s, 2H), 3.45 (m, 4H), 2.92 (m, 4H), 2.68 (m, 2H), 2.42 (m, 1H), 2.08 (m, 2H), 1.82 (m, 2H), 1.29 (m, 2H).

MS m/z (+ESI): 516 [M+H]$^+$.

Example 50

3-oxo-3,4-dihydro-2H-pyrido[3,2-b][1,4]thiazine-6-carboxylic acid {1-[2-(7-methoxy-quinoxalin-2-yl-sulfanyl)-ethyl]-piperidin-4-yl}-amide The title compound is prepared as a yellow solid (7 mg, 10% yield) following Scheme 3 and in analogy to Example 35 using 3-oxo-3,4-dihydro-2H-pyrido[3,2-b][1,4]thiazine-6-carboxylic acid (26 mg, 0.12 mmol, 1.0 eq) and 1-[2-(7-methoxy-quinoxalin-2-ylsulfanyl)-ethyl]-piperidin-4-ylamine (40 mg, 0.12 mmol, 1.0 eq) as starting materials.

$^1$H-NMR (400 MHz, DMSO-d$_6$) δ ppm: 11.00 (s, 1H), 8.63 (s, 1H), 8.02 (d, J=8.0 Hz, 1H), 7.96 (d, J=8.0 Hz, 1H), 7.91 (d, J=9.1 Hz, 1H), 7.59 (d, J=7.8 Hz, 1H), 7.35 (dd, J=2.8, 9.1 Hz, 1H), 7.28 (d, J=2.8 Hz, 1H), 3.94 (s, 3H), 3.79 (m, 1H), 3.64 (s, 2H), 3.48 (t, J=7.0 Hz, 2H), 2.94 (m, 2H), 2.72 (t, J=7.0 Hz, 2H), 2.28 (m, 2H), 1.78 (m, 2H), 1.52 (m, 2H).

MS m/z (+ESI): 511.2 [M+H]$^+$.

Example 51

7-chloro-3-oxo-3,4-dihydro-2H-pyrido[3,2-b][1,4]thiazine-6-carboxylic acid {1-[2-(7-methoxy-quinoxalin-2-ylsulfanyl)-ethyl]-piperidin-4-yl}-amide The title compound is prepared as a yellow solid (9 mg, 12% yield) following Scheme 3 and in analogy to Example 35 using 7-chloro-3-oxo-3,4-dihydro-2H-pyrido[3,2-b][1,4]thiazine-6-carboxylic acid (31 mg, 0.12 mmol, 1.0 eq) and 1-[2-(7-methoxy-quinoxalin-2-ylsulfanyl)-ethyl]-piperidin-4-ylamine (40 mg, 0.12 mmol, 1.0 eq) as starting materials.

$^1$H-NMR (400 MHz, DMSO-d$_6$) δ ppm: 11.23 (s, 1H), 8.62 (s, 1H), 8.48 (d, J=7.8 Hz, 1H), 8.07 (s, 1H), 7.91 (d, J=9.1 Hz, 1H), 7.34 (dd, J=2.8, 9.1 Hz, 1H), 7.28 (d, J=2.8 Hz, 1H), 3.95 (s, 3H), 3.75 (m, 1H), 3.61 (s, 2H), 3.48 (t, J=7.0 Hz, 2H), 2.98 (m, 2H), 2.72 (t, J=7.0 Hz, 2H), 2.22 (m, 2H), 1.82 (m, 2H), 1.50 (m, 2H).

MS m/z (+ESI): 545.2 [M+H]$^+$.

Example 52

3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-methyl-amide Preparation of N-{1-[2-(7-methoxy-quinoxalin-2-ylsulfanyl)-ethyl]-piperidin-4-yl}-2-nitro-benzenesulfonamide N,N-Diisopropylethylamine (318 μL, 1.82 mmol, 2.5 eq) is added at room temperature to a stirred solution of 1-[2-(7-methoxy-quinoxalin-2-ylsulfanyl)-ethyl]-piperidin-4-ylamine (237 mg, 0.73 mmol, 1.0 eq) in dichloromethane (4 mL), followed by 2-nitro-benzenesulfonyl chloride (183 mg, 0.80 mmol, 1.1 eq). After 2 hours stirring at room temperature, the reaction mixture is extracted with dichloromethane (3×10 mL) and water (10 mL). The combined organic layers are dried over sodium sulfate, filtered and concentrated to give a residue that is purified by column chromatography (silica gel, eluent: ethyl acetate 100%) to afford N-{1-[2-(7-methoxy-quinoxalin-2-ylsulfanyl)-ethyl]-piperidin-4-yl}-2-nitro-benzenesulfonamide as a yellow waxy solid (307 mg, 82% yield).

$^1$H-NMR (400 MHz, DMSO-d$_6$) δ ppm: 8.59 (s, 1H), 8.18 (d, J=7.5 Hz, 1H), 8.04 (m, 1H), 7.85-7.96 (m, 3H), 7.33 (dd, J=2.8, 9.1 Hz, 1H), 7.25 (d, J=2.6 Hz, 1H), 3.92 (s, 3H), 3.41 (t, J=7.0 Hz, 2H), 3.11 (m, 1H), 2.88 (m, 2H), 2.62 (t, J=7.0 Hz, 2H), 2.02 (m, 2H), 1.60 (m, 2H), 1.45 (m, 2H).

MS m/z (+ESI): 504.2 [M+H]$^+$.

Preparation of N-{1-[2-(7-methoxy-quinoxalin-2-ylsulfanyl)-ethyl]-piperidin-4-yl}-N-methyl-2-nitro-benzenesulfonamide Cesium carbonate (293 mg, 0.90 mmol, 1.5 eq) is added at room temperature to a stirred solution of N-{1-[2-(7-methoxy-quinoxalin-2-ylsulfanyl)-ethyl]-piperidin-4-yl}-2-nitro-benzenesulfonamide (307 mg, 0.60 mmol, 1.0 eq) in N,N-dimethylformamide (4 mL), followed by methyl iodide (56 μL, 0.90 mmol, 1.5 eq). After 15 hours stirring at room temperature, solvent is evaporated and the residue is extracted with ethyl acetate (3×10 mL) and water (10 mL). The combined organic layers are dried over sodium sulfate, filtered and concentrated to give a residue that is purified by column chromatography (silica gel, eluent: cyclohexane:ethyl acetate, 4:1 to 1:0, v/v) to afford N-{1-[2-(7-methoxy-quinoxalin-2-ylsulfanyl)-ethyl]-piperidin-4-yl}-N-methyl-2-nitro-benzenesulfonamide as a yellow solid (106 mg, 34% yield).

$^1$H-NMR (400 MHz, DMSO-d$_6$) δ ppm: 8.61 (s, 1H), 8.05 (m, 1H), 7.97 (m, 1H), 7.85-7.90 (m, 3H), 7.34 (dd, J=2.8, 9.1 Hz, 1H), 7.26 (d, J=2.6 Hz, 1H), 3.93 (s, 3H), 3.70 (m, 1H), 3.43 (t, J=6.9 Hz, 2H), 3.02 (m, 2H), 2.78 (s, 3H), 2.67 (t, J=6.9 Hz, 2H), 2.10 (m, 2H), 1.68 (m, 2H), 1.40 (m, 2H).

MS m/z (+ESI): 518.3 [M+H]$^+$.

Preparation of {1-[2-(7-methoxy-quinoxalin-2-ylsulfanyl)-ethyl]-piperidin-4-yl}-methyl-amine 1,8-diazabicyclo[5.4.0]undec-7-ene (36 μL, 0.24 mmol, 1.2 eq) is added at room temperature to a stirred solution of N-{1-[2-(7-methoxy-quinoxalin-2-ylsulfanyl)-ethyl]-piperidin-4-yl}-N-methyl-2-nitro-benzenesulfonamide (104 mg, 0.20 mmol, 1.0 eq) in N,N-dimethylformamide (3 mL), followed by 2-mercaptoethanol (56 μL, 0.90 mmol, 1.5 eq). After 15 hours stirring at room temperature, solvent is evaporated and the residue is extracted with ethyl acetate (3×10 mL) and water (10 mL). The combined organic layers are dried over sodium sulfate, filtered and concentrated to afford {1-[2-(7-methoxy-quinoxalin-2-ylsulfanyl)-ethyl]-piperidin-4-yl}-methyl-amine as a yellow oil (43 mg, 62% yield).

$^1$H-NMR (400 MHz, DMSO-d$_6$) δ ppm: 8.61 (s, 1H), 7.90 (d, J=9.1 Hz, 1H), 7.34 (dd, J=2.7, 9.1 Hz, 1H), 7.27 (d, J=2.7 Hz, 1H), 3.94 (s, 3H), 3.45 (t, J=7.0 Hz, 2H), 2.82 (m, 2H), 2.67 (t, J=7.0 Hz, 2H), 2.28 (m, 4H), 2.07 (m, 2H), 1.78 (m, 2H), 1.20 (m, 2H).

MS m/z (+ESI): 333.3 [M+H]$^+$.

Preparation of 3-oxo-3,4-dihydro-2H-benzo[1,4]
thiazine-6-carboxylic acid {1-[2-(7-methoxy-quinoxalin-2-ylsulfanyl)-ethyl]-piperidin-4-yl}-methyl-amide 3-oxo-3,4-dihydro-2H-benzo[1,4]thiazine-6-carboxylic acid (26 mg, 0.11 mmol, 1.0 eq) is added at room temperature to a stirred solution of {1-[2-(7-methoxy-quinoxalin-2-ylsulfanyl)-ethyl]-piperidin-4-yl}-methyl-amine (40 mg, 0.11 mmol, 1.0 eq) in N,N-dimethylformamide (3 mL), followed by O-(7-azabenzotriazol-1-yl)-N,N,N',N'-tetramethyluronium hexafluorophosphate (45 mg, 0.11 mmol, 1.0 eq), and triethylamine (16 µL, 0.11 mmol, 1.0 eq). After 4 hours stirring at room temperature, solvent is evaporated and the residue is purified by preparative HPLC to afford 3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-methyl-amide as a yellow solid (22 mg, 35% yield).

MS m/z (+ESI): 524.3 [M+H]$^+$.

Example 53

3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide Preparation of
2-(6-methoxy-quinolin-3-ylsulfanyl)-ethanol 2-Mercaptoethanol (0.11 mL, 1.51 mmol, 2.0 eq) is added at room temperature to a stirred solution of 3-bromo-6-methoxy-quinoline (200 mg, 0.76 mmol, 1.0 eq) in N,N-dimethylformamide (10 mL), followed by sodium hydride (50%, 174 mg, 3.78 mol, 5.0 eq). After 4 hours stirring at 80° C., solvent is evaporated and the residue is extracted with ethyl acetate (3×50 mL) and water (10 mL). The combined organic layers are dried over sodium sulfate, filtered and concentrated to give a crude product that is purified by column chromatography (silica gel, eluent: ethyl acetate:hexane, 1:4 to 1:2, v/v) to afford 2-(6-methoxy-quinolin-3-ylsulfanyl)-ethanol as a yellow viscous oil (140 mg, 79% yield).

$^1$H-NMR (400 MHz, DMSO-d$_6$) δ ppm: 8.62 (s, 1H), 8.19 (d, J=12.0 Hz, 1H), 7.85 (d, J=8.8 Hz, 1H), 7.30 (m, 2H), 4.99 (t, J=6.0 Hz, 1H), 3.87 (s, 3H), 3.64 (t, J=6.0 Hz, 2H), 3.16 (t, J=6.2 Hz, 2H).

MS m/z (+ESI): 236.1 [M+H]$^+$.

Preparation of
(6-methoxy-quinolin-3-ylsulfanyl)-acetaldehyde

Dess-Martin periodinane (400 mg, 0.94 mmol, 2.0 eq) is added at 0° C. to a stirred solution of 2-(6-methoxy-quinolin-3-ylsulfanyl)-ethanol (130 mg, 0.55 mmol, 1.0 eq) in dichloromethane (5 mL). The reaction mixture is stirred at room temperature for 1 hour, concentrated to give a crude product that is directly engaged in the next step (130 mg, 100%).

MS m/z (+ESI): 234.0 [M+H]$^+$.

Preparation of {1-[2-(6-methoxy-quinolin-3-ylsulfanyl)-ethyl]-piperidin-4-yl}-carbamic acid tert-butyl ester Piperidin-4-yl-carbamic acid tert-butyl ester (3.4 g, 17.15 mmol, 1.0 eq) is added at room temperature to a stirred solution of (6-methoxy-quinolin-3-ylsulfanyl)-acetaldehyde (4.0 g, 17.15 mmol, 1.0 eq) in 1,2-dichloroethane (200 mL), followed by sodium triacetoxyborohydride (2.06 g, 34.3 mmol, 2.0 eq). After 1 hour stirring at room temperature, the reaction mixture is extracted with dichloromethane (3×50 mL) and a saturated sodium hydrogen carbonate aqueous solution (50 mL). The combined organic layers are dried over sodium sulfate, filtered and concentrated to give a crude product that is purified by column chromatography (silica gel, eluent: dichloromethane:methanol, 20:1 to 10:1, v/v) to give a yellow solid that is further recrystallized with ethyl acetate: hexane (1:6, v/v) to afford {1-[2-(6-methoxy-quinolin-3-ylsulfanyl)-ethyl]-piperidin-4-yl}-carbamic acid tert-butyl ester as a yellow oil (724 mg, 10% yield).

$^1$H-NMR (400 MHz, MeOH-d$_4$) δ ppm: 8.61 (d, J=2.0 Hz, 1H), 8.15 (s, 1H), 7.84 (d, J=8.8 Hz, 1H), 7.29 (m, 2H), 6.75 (d, J=7.6 Hz, 1H), 3.87 (s, 3H), 3.19 (m, 3H), 2.82 (m, 2H), 2.56 (m, 2H), 1.96 (m, 2H), 1.65 (m, 2H), 1.35 (m, 11H).

MS m/z (+ESI): 418.4 [M+H]$^+$.

Preparation of 1-[2-(6-methoxy-quinolin-3-ylsulfanyl)-ethyl]-piperidin-4-ylamine Trifluoroacetic acid (1.88 mL, 24.2 mmol, 15.0 eq) is added at 0° C. to a stirred solution of {1-[2-(6-methoxy-quinolin-3-ylsulfanyl)-ethyl]-piperidin-4-yl}-carbamic acid tert-butyl ester (724 mg, 1.61 mmol, 1.0 eq) in dichloromethane (75 mL). After 15 hours stirring at room temperature, the reaction mixture is extracted with dichloromethane (3×50 mL) and water (50 mL) and the pH value adjusted to 12 by the addition of a 1N sodium hydroxide aqueous solution. The combined organic layers are dried over sodium sulfate, filtered and concentrated to afford 1-[2-(6-methoxy-quinolin-3-ylsulfanyl)-ethyl]-piperidin-4-ylamine as a brown oil (544 mg, 99% yield).

$^1$H-NMR (400 MHz, DMSO-d$_6$) δ ppm: 8.64 (d, J=2.3 Hz, 1H), 8.18 (d, J=2.2 Hz, 1H), 7.87 (d, J=8.8 Hz, 1H), 7.30-7.35 (m, 2H), 3.89 (s, 3H), 3.35 (m, 1H), 3.22 (t, J=7.0 Hz, 2H), 2.82 (m, 2H), 2.64 (t, J=7.0 Hz, 2H), 1.97 (m, 2H), 1.65 (m, 2H), 1.22 (m, 2H).

MS m/z (+ESI): 318.4 [M+H]$^+$.

Preparation of 3-oxo-3,4-dihydro-2H-benzo[1,4]
thiazine-6-carboxylic acid {1-[2-(6-methoxy-quinolin-3-ylsulfanyl)-ethyl]-piperidin-4-yl}-amide 3-oxo-3,4-dihydro-2H-benzo[1,4]thiazine-6-carboxylic acid (21 mg, 0.09 mmol, 1.0 eq) is added at room temperature to a stirred solution of 1-[2-(6-methoxy-quinolin-3-ylsulfanyl)-ethyl]-piperidin-4-ylamine (30 mg, 0.09 mmol, 1.0 eq) in N,N-dimethylformamide (3 mL), followed by 1-hydroxybenzotriazole (13 mg, 0.10 mmol, 1.1 eq), N-(3-dimethylaminopropyl)-N'-ethylcarbodiimide hydrochloride (20 mg, 0.10 mmol, 1.15 eq) and N,N-diisopropylethylamine (35 µL, 0.20 mmol, 2.25 eq). After 15 hours stirring at room temperature, solvent is evaporated and the residue is extracted with dichloromethane (3×5 mL) and water (5 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide as a white solid (30 mg, 59% yield).

$^1$H-NMR (400 MHz, DMSO-d$_6$) δ ppm: 11.65 (s, 1H), 8.65 (d, J=2.5 Hz, 1H), 8.20-8.25 (m, 2H), 7.88 (d, J=8.8 Hz, 1H), 7.30-7.45 (m, 5H), 3.93 (s, 3H), 3.75 (m, 1H), 3.50 (s, 2H), 3.29 (t, J=7.0 Hz, 2H), 2.95 (m, 2H), 2.66 (t, J=7.0 Hz, 2H), 2.11 (m, 2H), 1.78 (m, 2H), 1.58 (m, 2H).

MS m/z (+ESI): 509.3 [M+H]$^+$.

Example 54

7-chloro-3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide The title compound is prepared as a white solid (13 mg, 24% yield) following Scheme 3 and in analogy to Example 53 using 7-chloro-3-oxo-3,4-dihydro-2H-benzo[1,4]thiazine-6-carboxylic acid (22 mg, 0.09 mmol, 1.0 eq) and 1-[2-(6-methoxy-quinolin-3-ylsulfanyl)-ethyl]-piperidin-4-ylamine (30 mg, 0.09 mmol, 1.0 eq) as starting materials.

$^1$H-NMR (400 MHz, DMSO-d$_6$) δ ppm: 10.73 (s, 1H), 8.65 (d, J=2.2 Hz, 1H), 8.35 (d, J=7.7 Hz, 1H), 8.20 (d, J=2.2 Hz, 1H), 7.86 (m, 2H), 7.50 (s, 1H), 7.30-7.37 (m, 3H), 3.93 (s, 3H), 3.70 (m, 1H), 3.52 (s, 2H), 3.25 (t, J=7.0 Hz, 2H), 2.90 (m, 2H), 2.65 (t, J=7.0 Hz, 2H), 2.11 (m, 2H), 1.78 (m, 2H), 1.50 (m, 2H).

MS m/z (+ESI): 543.3 [M+H]$^+$.

Example 55

3-oxo-3,4-dihydro-2H-pyrido[3,2-b][1,4]thiazine-6-carboxylic acid {1-[2-(6-methoxy-quinolin-3-ylsulfanyl)-ethyl]-piperidin-4-yl}-amide The title compound is prepared as a light yellow solid (64 mg, 30% yield) following Scheme 3 and in analogy to Example 53 using 3-oxo-3,4-dihydro-2H-pyrido[3,2-b][1,4]thiazine-6-carboxylic acid (19 mg, 0.09 mmol, 1.0 eq) and 1-[2-(6-methoxy-quinolin-3-ylsulfanyl)-ethyl]-piperidin-4-ylamine (30 mg, 0.09 mmol, 1.0 eq) as starting materials.

$^1$H-NMR (400 MHz, DMSO-d$_6$) δ ppm: 11.00 (s, 1H), 8.66 (d, J=2.2 Hz, 1H), 8.20 (d, J=2.2 Hz, 1H), 8.02 (d, J=8.0 Hz, 1H), 7.95 (d, J=8.0 Hz, 1H), 7.88 (d, J=8.8 Hz, 1H), 7.59 (d, J=8.0 Hz, 1H), 7.31-7.35 (m, 2H), 3.90 (s, 3H), 3.78 (m, 1H), 3.64 (s, 2H), 3.26 (t, J=7.0 Hz, 2H), 2.86 (m, 2H), 2.65 (t, J=7.0 Hz, 2H), 2.20 (m, 2H), 1.75 (m, 2H), 1.50 (m, 2H).

MS m/z (+ESI): 510.3 [M+H]$^+$.

Example 56

7-chloro-3-oxo-3,4-dihydro-2H-pyrido[3,2-b][1,4]thiazine-6-carboxylic acid {1-[2-(6-methoxy-quinolin-3-ylsulfanyl)-ethyl]-piperidin-4-yl}-amide The title compound is prepared as a light yellow solid (49 mg, 91% yield) following Scheme 3 and in analogy to Example 53 using 7-chloro-3-oxo-3,4-dihydro-2H-pyrido[3,2-b][1,4]thiazine-6-carboxylic acid (22 mg, 0.09 mmol, 1.0 eq) and 1-[2-(6-methoxy-quinolin-3-ylsulfanyl)-ethyl]-piperidin-4-ylamine (30 mg, 0.09 mmol, 1.0 eq) as starting materials.

$^1$H-NMR (400 MHz, DMSO-d$_6$) δ ppm: 11.22 (s, 1H), 8.65 (d, J=2.3 Hz, 1H), 8.47 (d, J=7.8 Hz, 1H), 8.20 (d, J=2.2 Hz, 1H), 8.07 (s, 1H), 7.87 (d, J=9.0 Hz, 1H), 7.30-7.37 (m, 2H), 3.90 (s, 3H), 3.72 (m, 1H), 3.61 (s, 2H), 3.26 (t, J=7.0 Hz, 2H), 2.90 (m, 2H), 2.65 (t, J=7.0 Hz, 2H), 2.15 (m, 2H), 1.80 (m, 2H), 1.50 (m, 2H).

MS m/z (+ESI): 544.3 [M+H]$^+$.

Example 57

3-oxo-3,4-dihydro-2H-benzo[1,4]thiazine-6-carboxylic acid {1-[2-(7-hydroxy-quinoxalin-2-yloxy)-ethyl]-piperidin-4-yl}-amide A solution of 1M boron tribromide in dichloromethane (2.93 mL, 2.93 mmol, 8.0 eq) is added at 0° C. to a stirred solution of 3-oxo-3,4-dihydro-2H-benzo[1,4]thiazine-6-carboxylic acid {1-[2-(7-methoxy-quinoxalin-2-yloxy)-ethyl]-piperidin-4-yl}-amide (190 mg, 0.37 mmol, 1.0 eq) in dichloromethane (2.5 mL). The reaction mixture is stirred at 0° C. for 30 minutes and then at 40° C. for 24 hours. The reaction mixture is cooled down to 0° C. before the addition of methanol (1 mL). Solvents are evaporated and the crude is taken in water (10 mL), the pH is adjusted to 10 by the addition of 1N sodium hydroxide aqueous solution and the resulting aqueous layer is extracted with dichloromethane (3×10 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid {1-[2-(7-hydroxy-quinoxalin-2-yloxy)-ethyl]-piperidin-4-yl}-amide as a white lyophilizated powder (28 mg, 30% yield).

$^1$H-NMR (400 MHz, DMSO-d$_6$) δ ppm: 10.65 (s, 1H), 10.35 (br, 1H), 8.33 (s, 1H), 8.23 (d, J=7.7 Hz, 1H), 7.82 (d, J=9.0 Hz, 1H), 7.37-7.47 (m, 3H), 7.15 (dd, J=2.5, 9.0 Hz, 1H), 7.04 (d, J=2.5 Hz, 1H), 4.53 (t, J=5.6 Hz, 2H), 3.75 (m, 1H), 3.50 (s, 2H), 3.02 (m, 2H), 2.81 (t, J=5.6 Hz, 2H), 2.18 (m, 2H), 1.78 (m, 2H), 1.55 (m, 2H).

MS m/z (+ESI): 480.3 [M+H]$^+$.

Example 58

3-oxo-3,4-dihydro-2H-benzo[1,4]thiazine-6-carboxylic acid {1-[2-(7-ethoxy-quinoxalin-2-yloxy)-ethyl]-piperidin-4-yl}-amide Ethyl bromide (12.8 µL, 0.17 mmol, 1.1 eq) is added at room temperature to a stirred solution of 3-oxo-3,4-dihydro-2H-benzo[1,4]thiazine-6-carboxylic acid {1-[2-(7-hydroxy-quinoxalin-2-yloxy)-ethyl]-piperidin-4-yl}-amide (75 mg, 0.16 mmol, 1.0 eq) in N,N-dimethylformamide (2 mL), followed by potassium carbonate (28.1 mg, 0.20 mmol, 1.3 eq). After 3 hours stirring at 60° C., solvent is evaporated and the residue is extracted with dichloromethane (3×5 mL) and water (5 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid {1-[2-(7-ethoxy-quinoxalin-2-yloxy)-ethyl]-piperidin-4-yl}-amide as a white powder (15 mg, 18% yield).

$^1$H-NMR (400 MHz, DMSO-d$_6$) δ ppm: 10.64 (s, 1H), 8.40 (s, 1H), 8.19 (d, J=7.7 Hz, 1H), 7.87 (d, J=9.09 Hz, 1H), 7.36-7.48 (m, 3H), 7.23 (dd, J=2.7, 9.0 Hz, 1H), 7.19 (d, J=2.7 Hz, 1H), 4.55 (t, J=5.8 Hz, 2H), 4.20 (q, J=6.9 Hz, 2H), 3.72 (m, 1H), 3.50 (s, 2H), 3.00 (m, 2H), 2.79 (t, J=5.8 Hz, 2H), 2.13 (m, 2H), 1.75 (m, 2H), 1.54 (m, 2H), 1.40 (t, J=6.9 Hz, 3H).

MS m/z (+ESI): 508.2 [M+H]$^+$.

Example 59 acetic acid 3-(2-{4-[(3-oxo-3,4-dihydro-2H-benzo[1,4]thiazine-6-carbonyl)-amino]-piperidin-1-yl}-ethoxy)-quinoxalin-6-yl ester Acetyl chloride (11.4 µL, 0.16 mmol, 1.1 eq) is added at room temperature to a stirred solution of 3-oxo-3,4-dihydro-2H-benzo[1,4]thiazine-6-carboxylic acid {1-[2-(7-hydroxy-quinoxalin-2-yloxy)-ethyl]-piperidin-4-yl}-amide (70 mg, 0.15 mmol, 1.0 eq) in N,N-dimethylformamide (2 mL), followed by triethylamine (40.7 µL, 0.29 mmol, 2.0 eq). After 1 hour stirring at room temperature, solvent is evaporated and the residue is extracted with dichloromethane (3×5 mL) and water (5 mL). The combined organic layers are dried over sodium sulfate, filtered and concentrated to give a residue that is purified by preparative HPLC to afford acetic acid 3-(2-{4-[(3-oxo-3,4-dihydro-2H-benzo[1,4]thiazine-6-carbonyl)-amino]-piperidin-1-yl}-ethoxy)-quinoxalin-6-yl ester as a white powder (35 mg, 41% yield).

MS m/z (+ESI): 522.1 [M+H]$^+$.

Example 60 methanesulfonic acid 3-(2-{4-[(3-oxo-3,4-dihydro-2H-benzo[1,4]thiazine-6-carbonyl)-amino]-piperidin-1-yl}-ethoxy)-quinoxalin-6-yl ester Methanesulfonic anhydride (519 mg, 2.92 mmol, 20.0 eq) is added at 0° C. to a stirred solution of 3-oxo-3,4-dihydro-2H-benzo[1,4]thiazine-6-carboxylic acid {1-[2-(7-hydroxy-quinoxalin-2-yloxy)-ethyl]-piperidin-4-yl}-amide (70 mg, 0.15 mmol, 1.0 eq) in N,N-dimethylformamide (2 mL), followed by triethylamine (610.4 µL, 4.38 mmol, 30.0 eq). After 30 minutes stirring at room temperature, solvent is evaporated and the residue is extracted with dichloromethane (3×5 mL) and water (5 mL). The combined organic layers are dried over sodium sulfate, filtered and concentrated to give a residue that is purified by preparative HPLC to afford methanesulfonic acid 3-(2-{4-[(3-oxo-3,4-dihydro-2H-benzo[1,4]thiazine-6-carbonyl)-amino]-piperidin-1-yl}-ethoxy)-quinoxalin-6-yl ester as an off-white powder (25 mg, 26% yield).

$^1$H-NMR (400 MHz, DMSO-d$_6$) δ ppm: 10.64 (s, 1H), 8.66 (s, 1H), 8.20 (d, J=7.7 Hz, 1H), 8.12 (d, J=9.0 Hz, 1H), 7.80 (d, J=2.5 Hz, 1H), 7.60 (dd, J=2.5, 9.0 Hz, 1H), 7.40 (m, 3H), 4.58 (t, J=5.7 Hz, 2H), 3.75 (m, 1H), 3.48 (s, 5H), 2.98 (m, 2H), 2.80 (t, J=5.7 Hz, 2H), 2.14 (m, 2H), 1.75 (m, 2H), 1.54 (m, 2H).

MS m/z (+ESI): 558.1 [M+H]$^+$.

Example 61

[3-(2-{4-[(3-oxo-3,4-dihydro-2H-benzo[1,4]thiazine-6-carbonyl)-amino]-piperidin-1-yl}-ethoxy)-quinoxalin-6-yloxy]-acetic acid methyl ester Bromo-acetic acid methyl ester (20.0 µL, 0.22 mmol, 1.05 eq) is added at room temperature to a stirred solution of 3-oxo-3,4-dihydro-2H-benzo[1,4]thiazine-6-carboxylic acid {1-[2-(7-hydroxy-quinoxalin-2-yloxy)-ethyl]-piperidin-4-yl}-amide (100 mg, 0.21 mmol, 1.0 eq) in N,N-dimethylformamide (2 mL), followed by potassium carbonate (57.6 mg, 0.42 mmol, 2.0 eq). After 5 hours stirring at room temperature, solvent is evaporated and the residue is extracted with dichloromethane (3×5 mL) and water (5 mL). The combined organic layers are dried over sodium sulfate, filtered and concentrated to give a residue that is purified by preparative HPLC to afford [3-(2-{4-[(3-oxo-3,4-dihydro-2H-benzo[1,4]thiazine-6-carbonyl)-amino]-piperidin-1-yl}-ethoxy)-quinoxalin-6-yloxy]-acetic acid methyl ester as a white powder (8 mg, 6% yield).

$^1$H-NMR (400 MHz, DMSO-d$_6$) δ ppm: 10.64 (s, 1H), 8.44 (s, 1H), 8.21 (d, J=7.7 Hz, 1H), 7.91 (d, J=9.0 Hz, 1H), 7.37-7.47 (m, 3H), 7.31 (dd, J=2.8, 9.0 Hz, 1H), 7.19 (d, J=2.8 Hz, 1H), 5.01 (s, 2H), 4.54 (t, J=5.7 Hz, 2H), 3.72 (m, 1H), 3.70 (s, 3H), 3.49 (s, 2H), 2.99 (m, 2H), 2.78 (t, J=5.7 Hz, 2H), 2.13 (m, 2H), 1.78 (m, 2H), 1.55 (m, 2H).

MS m/z (+ESI): 552.2 [M+H]$^+$.

Example 62

3-oxo-3,4-dihydro-2H-benzo[1,4]thiazine-6-carboxylic acid {1-[2-(7-difluoromethoxy-quinoxalin-2-yloxy)-ethyl]-piperidin-4-yl}-amide Chloro-difluoro-acetic acid ethyl ester (13.8 µL, 0.10 mmol, 1.0 eq) is added at room temperature to a stirred solution of 3-oxo-3,4-dihydro-2H-benzo[1,4]thiazine-6-carboxylic acid {1-[2-(7-hydroxy-quinoxalin-2-yloxy)-ethyl]-piperidin-4-yl}-amide (50 mg, 0.10 mmol, 1.0 eq) in N,N-dimethylformamide (5 mL), followed by potassium carbonate (14.4 mg, 0.10 mmol, 1.0 eq). After 15 hours stirring at 70° C., solvent is evaporated and the residue is acidified with 1N hydrochloric acid aqueous solution and the resulting aqueous layer is extracted with ethyl acetate (3×10 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid {1-[2-(7-difluoromethoxy-quinoxalin-2-yloxy)-ethyl]-piperidin-4-yl}-amide as a white lyophilized powder (5 mg, 10% yield).

MS m/z (+ESI): 530.2 [M+H]$^+$.

Example 63

3-oxo-3,4-dihydro-2H-benzo[1,4]thiazine-6-carboxylic acid {1-[3-methoxy-2-(7-methoxy-quinoxalin-2-yloxy)-propyl]-piperidin-4-yl}-amide Preparation of (1-oxiranylmethyl-piperidin-4-yl)-carbamic acid tert-butyl ester Epibromohydrin (1.25 mL, 1.44 mmol, 1.0 eq) is added at room temperature to a stirred solution of piperidin-4-yl-carbamic acid tert-butyl ester (3.0 g, 1.44 mmol, 1.0 eq) in N,N-dimethylformamide (90 mL), followed by potassium carbonate (2.00 g, 1.43 mmol, 1.0 eq). After 24 hours stirring at room temperature, solvent is evaporated and the residue is extracted with dichloromethane (3×40 mL) and water (40 mL). The combined organic layers are dried over sodium sulfate, filtered and concentrated to afford (1-oxiranylmethyl-piperidin-4-yl)-carbamic acid tert-butyl ester as an off-white solid (3.86 g, 99% yield).

$^1$H-NMR (400 MHz, DMSO-d$_6$) δ ppm: 6.77 (d, J=7.9 Hz, 1H), 3.18 (m, 1H), 2.98 (m, 1H), 2.80, 2.87 (2m, 2H), 2.68 (dd, J=4.3, 5.2 Hz, 1H), 2.58 (dd, J=3.8, 13.3 Hz, 1H), 2.42 (dd, J=2.6, 5.2 Hz, 1H), 2.15 (dd, J=6.5, 13.3 Hz, 1H), 1.96 (m, 2H), 1.65 (m, 2H), 1.39 (m, 11H).

MS m/z (+ESI): 257.4 [M+H]$^+$.

Preparation of [1-(2-hydroxy-3-methoxy-propyl)-piperidin-4-yl]-carbamic acid tert-butyl ester (1-Oxiranylmethyl-piperidin-4-yl)-carbamic acid tert-butyl ester (0.5 g, 1.76 mmol, 1.0 eq) is dissolved at room temperature in a sodium methylate solution in methanol (5.4M, 3 mL). After 48 hours stirring at room temperature, the reaction mixture is cooled down to 0° C., quenched by slow addition of water, concentrated. The residue is extracted with dichloromethane (3×5 mL) and water (5 mL). The combined organic layers are dried over sodium sulfate, filtered and concentrated to afford [1-(2-hydroxy-3-methoxy-propyl)-piperidin-4-yl]-carbamic acid tert-butyl ester as a yellow foam (0.49 g, 97% yield).

MS m/z (+ESI): 289.3 [M+H]$^+$.

Preparation of 3-oxo-3,4-dihydro-2H-benzo[1,4]
thiazine-6-carboxylic acid {1-[3-methoxy-2-(7-
methoxy-quinoxalin-2-yloxy)-propyl]-piperidin-4-
yl}-amide The title compound is prepared as an off-white lyophilizated powder following Scheme 1 and in analogy to Example 1 using 2-chloro-7-methoxy-quinoxaline, [1-(2-hydroxy-3-methoxy-propyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.62 (s, 1H), 8.39 (s, 1H), 8.14 (d, J=7.7 Hz, 1H), 7.88 (d, J=9.0 Hz, 1H), 7.33-7.42 (m, 3H), 7.25 (dd, J=3.0, 9.0 Hz, 1H), 7.18 (d, J=2.8 Hz, 1H), 5.69 (m, 1H), 3.91 (s, 3H), 3.62-3.77 (m, 3H), 3.48 (s, 2H), 3.29 (s, 3H), 2.94, 3.08 (2m, 2H), 2.53-2.73 (m, 2H), 2.09, 2.18 (2m, 2H), 1.70 (m, 2H), 1.37, 1.48 (2m, 2H).

MS m/z (+ESI): 538.4 [M+H]$^+$.

Example 64

3-oxo-3,4-dihydro-2H-benzo[1,4]thiazine-6-carboxylic acid {1-[3-(2-methoxy-ethoxy)-2-(7-methoxy-quinoxalin-2-yloxy)-propyl]-piperidin-4-yl}-amide Preparation of {1-[2-hydroxy-3-(2-methoxy-ethoxy)-propyl]-piperidin-4-yl}-carbamic acid tert-butyl ester Sodium (57 mg, 2.56 mmol, 4.0 eq) is added at room temperature to a stirred suspension of (1-oxiranylmethyl-piperidin-4-yl)-carbamic acid tert-butyl ester (200 mg, 0.64 mmol, 1.0 eq) in 2-methoxy-ethanol (4 mL). After 72 hours stirring at room temperature, the reaction mixture is cooled down to 0° C., cautiously quenched by the dropwise addition of ice-water, concentrated to afford {1-[2-hydroxy-3-(2-methoxy-ethoxy)-propyl]-piperidin-4-yl}-carbamic acid tert-butyl ester as an orange oil (210 mg, 99% yield).

MS m/z (+ESI): 333.4 [M+H]$^+$.

Preparation of 3-oxo-3,4-dihydro-2H-benzo[1,4]
thiazine-6-carboxylic acid {1-[3-(2-methoxy-
ethoxy)-2-(7-methoxy-quinoxalin-2-yloxy)-propyl]-
piperidin-4-yl}-amide The title compound is prepared as a white lyophilizated powder following Scheme 1 and in analogy to Example 1 using 2-chloro-7-methoxy-quinoxaline, {1-[2-hydroxy-3-(2-methoxy-ethoxy)-propyl]-piperidin-4-yl}-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.62 (br, 1H), 8.39 (s, 1H), 8.14 (d, J=7.7 Hz, 1H), 7.88 (d, J=9.0 Hz, 1H), 7.33-7.42 (m, 3H), 7.26 (dd, J=2.7, 9.0 Hz, 1H), 7.18 (d, J=2.7 Hz, 1H), 5.67 (m, 1H), 3.91 (s, 3H), 3.65-3.80 (m, 3H), 3.53-3.63 (m, 2H), 3.50 (s, 2H), 3.41 (m, 2H), 3.20 (s, 3H), 2.63, 2.68 (2m, 2H), 2.58-2.72 (m, 2H), 2.09, 2.16 (2m, 2H), 1.70 (m, 2H), 1.39, 1.50 (2m, 2H).

MS m/z (+ESI): 582.2 [M+H]$^+$.

Example 65

3-oxo-3,4-dihydro-2H-benzo[1,4]thiazine-6-carboxylic acid {1-[2-(7-methoxy-quinoxalin-2-ylsulfanyl)-3-morpholin-4-yl-propyl]-piperidin-4-yl}-amide Preparation of
(1-thiiranylmethyl-piperidin-4-yl)-carbamic acid
tert-butyl ester Epithiochlorohydrine (268 mg, 2.40 mmol, 1.0 eq) is added at room temperature to a stirred solution of piperidin-4-yl-carbamic acid tert-butyl ester (500 mg, 2.40 mmol, 1.0 eq) in N,N-dimethylformamide (15 mL), followed by potassium carbonate (335 mg, 2.40 mmol, 1.0 eq). After 24 hours stirring at room temperature, solvent is evaporated and the residue is extracted with dichloromethane (3×20 mL) and water (20 mL). The combined organic layers are dried over sodium sulfate, filtered and concentrated to afford (1-thiiranylmethyl-piperidin-4-yl)-carbamic acid tert-butyl ester as a white solid (745 mg, 57% yield).

MS m/z (+ESI): 273.3 [M+H]$^+$.

Preparation of [1-(2-mercapto-3-morpholin-4-yl-propyl)-piperidin-4-yl]-carbamic acid tert-butyl ester Morpholine (80 µL, 0.83 mmol, 1.5 eq) is added at room temperature to a stirred solution of (1-thiiranylmethyl-piperidin-4-yl)-carbamic acid tert-butyl ester (300 mg, 0.55 mmol, 1.0 eq) in ethanol (2 mL). The reaction mixture is irradiated under microwave conditions for 4 minutes at 140° C. and 80 W and then solvent is evaporated to afford [1-(2-mercapto-3-morpholin-4-yl-propyl)-piperidin-4-yl]-carbamic acid tert-butyl ester as an off-white semisolid (266 mg, 67% yield).

MS m/z (+ESI): 360.3 [M+H]$^+$.

Preparation of 3-oxo-3,4-dihydro-2H-benzo[1,4]
thiazine-6-carboxylic acid {1-[2-(7-methoxy-qui-
noxalin-2-ylsulfanyl)-3-morpholin-4-yl-propyl]-
piperidin-4-yl}-amide The title compound is prepared as a light brown lyophilizated powder following Scheme 3 and in analogy to Example 1 using 2-chloro-7-methoxy-quinoxaline, [1-(2-mercapto-3-morpholin-4-yl-propyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.63 (s, 1H), 8.60 (s, 1H), 8.18 (d, J=7.8 Hz, 1H), 7.89 (d, J=9.1 Hz, 1H), 7.30-7.43 (m, 4H), 7.22 (d, J 2.7=Hz, 1H), 4.38 (m, 1H), 3.92 (s, 3H), 3.72 (m, 1H), 3.44-3.53 (m, 10H), 3.05 (m, 2H), 2.60-2.78 (m, 4H), 2.15 (m, 2H), 1.72 (m, 2H), 1.52 (m, 2H).

MS m/z (+ESI): 609.2 [M+H]$^+$.

Example 66

(3S,4S)-3-oxo-3,4-dihydro-2H-benzo[1,4]thiazine-6-carboxylic acid {3-hydroxymethyl-1-[2-(7-methoxy-quinoxalin-2-yloxy)-ethyl]-piperidin-4-yl}-amide Preparation of (3R,4S)-4-benzyloxycarbonylamino-
1-[2-(7-methoxy-quinoxalin-2-yloxy)-ethyl]-piperi-
dine-3-carboxylic acid ethyl ester The title compound is prepared as a yellow oil following Scheme 1 and in analogy to Example 1 using (3R,4S)-4-benzyloxycarbonylamino-piperidine-3-carboxylic acid ethyl ester (prepared according to procedures described in WO2005/066176), 2-bromo-ethanol and 2-chloro-7-methoxy-quinoxaline as starting materials.

MS m/z (+ESI): 509.4 [M+H]$^+$.

Preparation of (3R,4S)-4-amino-1-[2-(7-methoxy-
quinoxalin-2-yloxy)-ethyl]-piperidine-3-carboxylic
acid ethyl ester 10% Palladium on activated carbon (188 mg, 0.18 mmol, 0.5 eq) is added at room temperature to a stirred solution of (3R,4S)-4-benzyloxycarbonylamino-1-[2-(7-methoxy-quinoxalin-2-yloxy)-ethyl]-piperidine-3-carboxylic acid ethyl ester (200 mg, 0.35 mmol, 1.0 eq) in methanol (20 mL). The mixture is hydrogenated for 4 hours, then filtered through decalite. Solvent is removed to afford (3R,4S)-4-amino-1-[2-(7-methoxy-quinoxalin-2-yloxy)-ethyl]-piperidine-3-carboxylic acid ethyl ester as a yellow oil (119 mg, 81% yield).
MS m/z (+ESI): 375.4 [M+H]$^+$.

Preparation of (3R,4S)-1-[2-(7-methoxy-quinoxalin-2-yloxy)-ethyl]-4-[(3-oxo-3,4-dihydro-2H-benzo[1,4]thiazine-6-carbonyl)-amino]-piperidine-3-carboxylic acid ethyl ester The title compound is prepared as a yellow oil (135 mg, 71% yield) following Scheme 1 and in analogy to Example 1 using (3R,4S)-4-aminol-[2-(7-methoxy-quinoxalin-2-yloxy)-ethyl]-piperidine-3-carboxylic acid ethyl ester and 3-oxo-3,4-dihydro-2H-benzo[1,4]thiazine-6-carboxylic acid as starting materials.
MS m/z (+ESI): 566.4 [M+H]$^+$.

Preparation of (3S,4S)-3-oxo-3,4-dihydro-2H-benzo[1,4]thiazine-6-carboxylic acid {3-hydroxymethyl-1-[2-(7-methoxy-quinoxalin-2-yloxy)-ethyl]-piperidin-4-yl}-amide Lithium aluminium hydride (1.0M solution in tetrahydrofuran, 80 µL, 0.08 mmol, 1.0 eq) is added dropwise at −10° C. to a stirred solution of (3R,4S)-1-[2-(7-methoxy-quinoxalin-2-yloxy)-ethyl]-4-[(3-oxo-3,4-dihydro-2H-benzo[1,4]thiazine-6-carbonyl)-amino]-piperidine-3-carboxylic acid ethyl ester (50 mg, 0.08 mmol, 1.0 eq) in tetrahydrofuran (5 mL). After 30 minutes stirring at −10° C., the reaction mixture is cautiously quenched with ice-water (2 mL). Tetrahydrofuran is evaporated and the crude is extracted with dichloromethane (3×10 mL) and water (10 mL). The combined organic layers are dried over sodium sulfate, filtered and concentrated to give a residue that is purified by preparative HPLC to afford (3S,4S)-3-oxo-3,4-dihydro-2H-benzo[1,4]thiazine-6-carboxylic acid {3-hydroxymethyl-1-[2-(7-methoxy-quinoxalin-2-yloxy)-ethyl]-piperidin-4-yl}-amide as a yellow lyophilizated powder (6 mg, 14% yield).
MS m/z (+ESI): 524.3 [M+H]$^+$.

Example 67

(3S,4R)-3-oxo-3,4-dihydro-2H-benzo[1,4]thiazine-6-carboxylic acid {3-hydroxymethyl-1-[2-(7-methoxy-quinoxalin-2-yloxy)-ethyl]-piperidin-4-yl}-amide Preparation (3S,4R)-4-benzyloxycarbonylamino-1-[2-(7-methoxy-quinoxalin-2-ylsulfanyl)-ethyl]-piperidine-3-carboxylic acid ethyl ester The title compound is prepared as an off-white solid (232 mg, 70% yield) following Scheme 3 and in analogy to Example 35 using (3S,4R)-4-benzyloxycarbonylamino-piperidine-3-carboxylic acid ethyl ester (200 mg, 0.63 mmol, 1.0 eq) (prepared according to procedures described in WO2005/066176) and (7-methoxy-quinoxalin-2-ylsulfanyl)-acetaldehyde (158 mg, 0.63 mmol 1.0 eq) as starting materials.
MS m/z (+ESI): 525.4 [M+H]$^+$.

Preparation (3S,4R)-4-amino-1-[2-(7-methoxy-quinoxalin-2-ylsulfanyl)-ethyl]-piperidine-3-carboxylic acid ethyl ester Iodotrimethylsilane (26 µL, 0.18 mmol, 2.0 eq) is added at 0° C. to a stirred solution of (3S,4R)-4-benzyloxycarbonylamino-1-[2-(7-methoxy-quinoxalin-2-ylsulfanyl)-ethyl]-piperidine-3-carboxylic acid ethyl ester (50 mg, 0.09 mmol, 1.0 eq) in dichloromethane (5 mL). After 2 hours stirring at 0° C. and 4 hours at room temperature, the reaction mixture is quenched with methanol (2 mL) and extracted with dichloromethane (3×5 mL) and a 0.1N hydrochloric acid aqueous solution (5 mL). The combined organic layers are dried over sodium sulfate, filtered and concentrated to afford (3S,4R)-4-amino-1-[2-(7-methoxy-quinoxalin-2-ylsulfanyl)-ethyl]-piperidine-3-carboxylic acid ethyl ester as a yellow oil (21 mg, 55% yield).
MS m/z (+ESI): 391.3 [M+H]$^+$.

Preparation (3S,4R)-1-[2-(7-methoxy-quinoxalin-2-ylsulfanyl)-ethyl]-4-[(3-oxo-3,4-dihydro-2H-benzo[1,4]thiazine-6-carbonyl)-amino]-piperidine-3-carboxylic acid ethyl ester The title compound is prepared as an orange semisolid (280 mg, 87% yield) following Scheme 3 and in analogy to Example 35 using (3S,4R)-4-amino-1-[2-(7-methoxy-quinoxalin-2-ylsulfanyl)-ethyl]-piperidine-3-carboxylic acid ethyl ester (216 mg, 0.50 mmol, 1.0 eq) and 3-oxo-3,4-dihydro-2H-benzo[1,4]thiazine-6-carboxylic acid (113 mg, 0.50 mmol, 1.0 eq) as starting material.
MS m/z (+ESI): 582.3 [M+H]$^+$.

Preparation of (3R,4R)-3-oxo-3,4-dihydro-2H-benzo[1,4]thiazine-6-carboxylic acid {3-hydroxymethyl-1-[2-(7-methoxy-quinoxalin-2-ylsulfanyl)-ethyl]-piperidin-4-yl}-amide The title compound is prepared as a light yellow lyophilizated powder (38 mg, 32% yield) following Scheme 3 and in analogy to Example 66 using (3S,4R)-4-amino-1-[2-(7-methoxy-quinoxalin-2-ylsulfanyl)-ethyl]-piperidine-3-carboxylic acid ethyl ester (137 mg, 0.21 mmol, 1.0 eq) as starting material.
$^1$H-NMR (400 MHz, DMSO-d$6$) δ ppm: 10.67 (s, 1H), 8.62 (s, 1H), 8.21 (d, J=7.7 Hz, 1H), 7.91 (d, J=9.0 Hz, 1H), 7.29-7.41 (m, 5H), 4.62 (m, 1H), 4.08 (m, 1H), 3.94 (s, 3H), 3.60 (m, 2H), 3.51 (s, 2H), 3.46 (m, 2H), 2.79 (m, 2H), 2.70 (m, 2H), 2.33, 2.43 (2m, 2H), 1.99 (m, 1H), 1.67, 1.76 (2m, 2H).
MS m/z (+ESI): 540.6 [M+H]$^+$.

Example 68

7-chloro-3-oxo-3,4-dihydro-2H-benzo[1,4]thiazine-6-carboxylic acid {1-[2-(7-methoxy-3-methyl-quinoxalin-2-yloxy)-ethyl]-piperidin-4-yl}-amide Preparation of 4-methoxy-benzene-1,2-diamine 10% Palladium on activated carbon (1.0 g, 9.4 mmol, 0.15 eq) is added at room temperature to a stirred solution of 4-methoxy-2-nitro-phenylamine (10.0 g, 59.5 mmol, 1.0 eq) in methanol (70 mL). The mixture is hydrogenated for 72 hours, then filtered through decalite. Solvent is removed to afford 4-methoxy-benzene-1,2-diamine as a dark brown oil (8.0 g, 97% yield).
$^1$H-NMR (400 MHz, MeOH-d$4$) δ ppm: 6.62 (d, J=8.4 Hz, 1H), 6.34 (d, J=2.8 Hz, 1H), 6.18 (dd, J=2.8, 8.4 Hz, 1H), 3.82 (s, 3H).

Preparation of 7-methoxy-3-methyl-1H-quinoxalin-2-one

Pyruvic acid (60 mL, 868 mmol, 1.2 eq) is added at room temperature to a stirred suspension of 4-methoxy-benzene-1, 2-diamine (100 g, 724 mmol, 1.0 eq) in 1.8M sulfuric acid aqueous solution (1000 mL). After 24 hours stirring at room temperature, the reaction mixture is neutralized by the addition of 1N sodium hydroxide aqueous solution. The resulting precipitate is filtered and washed with water to afford 7-methoxy-3-methyl-1H-quinoxalin-2-one as a dark purple solid (125 g, 91% yield).

$^1$H-NMR (400 MHz, DMSO-d$_6$) δ ppm: 7.54 (d, J=8.8 Hz, 1H), 6.82 (dd, J, 2.0, 8.8 Hz, 1H), 6.69 (d, J=2.0 Hz, 1H), 3.78 (s, 3H), 2.31 (s, 3H).

Preparation of
3-chloro-6-methoxy-2-methyl-quinoxaline

A solution of 7-methoxy-3-methyl-1H-quinoxalin-2-one (125 g, 631 mmol, 1.0 eq) in phosphorus oxychloride (800 mL) is heated under reflux for 1 hour. Then the reaction mixture is cooled down to room temperature and the solvent is evaporated. The residue is poured into ice water and the resulting mixture is neutralized with 20% sodium hydroxide aqueous solution. The resulting precipitate is collected by filtration, washed with water to give a crude product that is purified by column chromatography (silica gel, eluent: petroleum ether:ethyl acetate, 100:1, v/v) to afford 3-chloro-6-methoxy-2-methyl-quinoxaline as a white solid (44.4 g, 34% yield).

$^1$H-NMR (400 MHz, DMSO-d$_6$) δ ppm: 7.86 (d, J=9.2 Hz, 1H), 7.42 (dd, J=2.4, 9.2 Hz, 1H), 7.32 (d, J=2.4 Hz, 1H), 3.90 (s, 3H), 2.66 (s, 3H).

MS m/z (+ESI): 209.1 [M+H]$^+$.

Preparation of 7-chloro-3-oxo-3,4-dihydro-2H-benzo[1,4]thiazine-6-carboxylic acid {1-[2-(7-methoxy-3-methyl-quinoxalin-2-yloxy)-ethyl]-piperidin-4-yl}-amide The title compound is prepared as a light yellow lyophilizated powder following Scheme 1 and in analogy to Example 1 using 3-chloro-6-methoxy-2-methyl-quinoxaline, [1-(2-hydroxy-ethyl)-piperidin-4-yl]-carbamic acid tert-butyl ester and 7-chloro-3-oxo-3,4-dihydro-2H-benzo[1,4]thiazine-6-carboxylic acid as starting materials.

$^1$H-NMR (400 MHz, DMSO-d$_6$) δ ppm: 10.70 (s, 1H), 8.35 (d, J=7.5 Hz, 1H), 7.80 (d, J=8.8 Hz, 1H), 7.49 (s, 1H), 7.18-7.22 (m, 2H), 6.94 (s, 1H), 4.55 (t, J=5.7 Hz, 2H), 3.90 (s, 3H), 3.71 (m, 1H), 3.51 (s, 2H), 2.98 (m, 2H), 2.81 (t, J=5.7 Hz, 2H), 2.62 (s, 3H), 2.22 (m, 2H), 1.80 (m, 2H), 1.50 (m, 2H).

MS m/z (+ESI): 542.3 [M+H]$^+$.

Example 69

3-oxo-3,4-dihydro-2H-benzo[1,4]thiazine-6-carboxylic acid {1-[2-(7-methylsulfanyl-quinoxalin-2-yloxy)-ethyl]-piperidin-4-yl}-amide Preparation of 7-bromo-1H-quinoxalin-2-one Bromine (7.36 mL, 147 mmol, 1.05 eq) is added at room temperature to a stirred suspension of 1H-quinoxalin-2-one (20 g, 137 mmol, 1.0 eq) in acetic acid (400 mL). After 48 hours stirring at room temperature, the reaction mixture is poured into ice (500 mL) and the resulting precipitate is collected by filtration, washed with water and ethyl acetate to afford 7-bromo-1H-quinoxalin-2-one as a yellow solid (29.4 g, 73% yield).

$^1$H-NMR (400 MHz, DMSO-d$_6$) δ ppm: 12.44 (br, 1H), 8.17 (s, 1H), 7.69 (d, J=8.8 Hz, 1H), 7.44 (m, 2H).

MS m/z (+ESI): 225.1 [M+H]$^+$.

Preparation of
7-methylsulfanyl-1H-quinoxalin-2-one

A solution of 7-bromo-1H-quinoxalin-2-one (12.0 g, 53.3 mmol, 1.0 eq) and sodium methanethiolate (9.44 g, 133.3 mmol, 2.5 eq) in N-methylpyrrolidone is stirred at 160° C. for 1 hour. Then solvent is evaporated and the residue is dissolved in water, acidified to pH=5 with 20% hydrochloric acid aqueous solution at 0° C., and the resulting precipitate is collected by filtration, washed with water and ethyl acetate to afford 7-methylsulfanyl-1H-quinoxalin-2-one as a yellow solid (9.23 g, 54% yield).

$^1$H-NMR (400 MHz, DMSO-d$_6$) δ ppm: 12.27 (br, 1H), 8.03 (s, 1H), 7.65 (d, J=8.4 Hz, 1H), 7.15 (dd, J=2.0, 8.4 Hz, 1H), 7.06 (d, J=2.0 Hz, 1H), 2.51 (s, 3H).

MS m/z (+ESI): 193.2 [M+H]$^+$.

Preparation of
2-chloro-7-methylsulfanyl-quinoxaline

A solution of 7-methylsulfanyl-1H-quinoxalin-2-one (9.23 g, 48.0 mmol, 1.0 eq) in phosphorus oxychloride (36 mL, 384.0 mmol, 8.0 eq) is heated under reflux for 30 minutes. Then the reaction mixture is cooled down to room temperature and the solvent is evaporated. The residue is poured into ice water, the resulting mixture is basified with saturated sodium hydrogen carbonate to pH=8-9 and extracted with ethyl acetate (3×50 mL). The combined organic layers are dried over sodium sulfate, filtered and concentrated to give a crude product that is purified by column chromatography (silica gel, eluent: petroleum ether:dichloromethane, 4:1 to 1:1, v/v) to afford 2-chloro-7-methylsulfanyl-quinoxaline as a green solid (3.41 g, 33% yield).

$^1$H-NMR (400 MHz, DMSO-d$_6$) δ ppm: 8.86 (s, 1H), 7.99 (d, J=8.8 Hz, 1H), 7.72-7.75 (m, 2H), 2.63 (s, 3H).

MS m/z (+ESI): 211.1 [M+H]$^+$.

Preparation of 3-oxo-3,4-dihydro-2H-benzo[1,4]thiazine-6-carboxylic acid {1-[2-(7-methylsulfanyl-quinoxalin-2-yloxy)-ethyl]-piperidin-4-yl}-amide The title compound is prepared as a light yellow lyophilizated powder following Scheme 1 and in analogy to Example 1 using 2-chloro-7-methylsulfanyl-quinoxaline, [1-(2-hydroxy-ethyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.50 (s, 1H), 8.21 (d, J=7.7 Hz, 1H), 7.88 (d, J=8.8 Hz, 1H), 7.37-7.53 (m, 5H), 4.56 (t, J=5.7 Hz, 2H), 3.75 (m, 1H), 3.50 (s, 2H), 3.01 (m, 2H), 2.79 (t, J=5.7 Hz, 2H), 2.62 (s, 3H), 2.15 (m, 2H), 1.77 (m, 2H), 1.55 (m, 2H).

MS m/z (+ESI): 510.3 [M+H]$^+$.

Example 70

5-thiophen-2-yl-isoxazole-3-carboxylic acid {1-[2-(3-methoxy-quinolin-6-yloxy)-ethyl]-piperidin-4-yl}-amide Preparation of 3-methoxy-quinolin-6-ylamine A suspension of 3-bromo-quinolin-6-ylamine (9.0 g, 40.3 mmol, 1.0 eq), sodium methoxide (10.9 g, 201.7 mmol, 5.0 eq) and copper powder (7.7 g, 121.0 mmol, 3.0 eq) in methanol (240 mL) is heated at 135° C. for 15 hours. The reaction mixture is then filtered and the filtrate is concentrated to give a yellow residue that is purified by column chromatography (silica gel, eluent: petroleum ether:ethyl acetate:triethylamine, 2:1:0.05, v/v/v) to afford 3-methoxy-quinolin-6-ylamine as a yellow solid (4.2 g, 59% yield).

$^1$H-NMR (400 MHz, DMSO-d$_6$) δ ppm: 8.16 (d, J=2.8 Hz, 1H), 7.58 (d, J=8.8 Hz, 1H), 7.29 (d, J=2.8 Hz, 1H), 6.93 (dd, J=2.4, 8.8 Hz, 1H), 6.70 (d, J=2.4 Hz, 1H), 5.36 (s, 2H), 3.83 (s, 3H).

MS m/z (+ESI): 175.1 [M+H]$^+$.

Preparation of 3-methoxy-quinolin-6-ol

A solution of sodium nitrite (3.49 g, 50.5 mmol, 1.1 eq) in water (20 mL) is added dropwise at 0° C. to a stirred solution of 3-methoxy-quinolin-6-ylamine (8.0 g, 45.9 mmol, 1.0 eq) in hydrochloric acid (160 mL, 321.3 mmol, 7.0 eq). The mixture is stirred at 0° C. for 2 hours before its addition to a vigorously stirred solution of 10% sulfuric acid (600 mL) at 85-90° C. within 20 minutes. The resulting solution is stirred at 90° C. for 1 hour, cooled down to room temperature, neutralized with sodium carbonate and extracted with ethyl acetate (3×250 mL). The combined organic layers are dried over sodium sulfate, filtered and concentrated to give a crude product that is purified by column chromatography (silica gel, eluent: petroleum ether:ethyl acetate:triethylamine, 3:1:0.1, v/v/v) to afford 3-methoxy-quinolin-6-ol as a red solid (2.9 g, 34% yield).

$^1$H-NMR (400 MHz, DMSO-d$_6$) δ ppm: 9.91 (s, 1H), 8.35 (d, J=2.8 Hz, 1H), 7.51 (d, J=2.8 Hz, 1H), 7.35 (d, J=8.8 Hz, 1H), 7.07 (m, 2H), 3.86 (s, 3H).

MS m/z (+ESI): 176.1 [M+H]$^+$.

Preparation of 5-thiophen-2-yl-isoxazole-3-carboxylic acid {1-[2-(3-methoxy-quinolin-6-yloxy)-ethyl]-piperidin-4-yl}-amide The title compound is prepared as a brown solid following Scheme 1 and in analogy to Example 2 using 3-methoxy-quinolin-6-ol, [1-(2-hydroxy-ethyl)-piperidin-4-yl]-carbamic acid tert-butyl ester and 5-thiophen-2-yl-isoxazole-3-carboxylic acid as starting materials.

$^1$H-NMR (400 MHz, DMSO-d$_6$) δ ppm: 8.71 (d, J=8.0 Hz, 1H), 8.46 (d, J=2.8 Hz, 1H), 7.78-7.87 (m, 3H), 7.63 (d, J=2.8 Hz, 1H), 7.32 (d, J=2.4 Hz, 1H), 7.18-7.28 (m, 3H), 4.20 (t, J=5.8 Hz, 2H), 3.91 (s, 3H), 3.79 (m, 1H), 3.00 (m, 2H), 2.79 (t, J=5.8 Hz, 2H), 2.18 (m, 2H), 1.78 (m, 2H), 1.67 (m, 2H).

MS m/z (+ESI): 479.2 [M+H]$^+$.

Example 71

3-oxo-3,4-dihydro-2H-benzo[1,4]thiazine-6-carboxylic acid {1-[2-(2-methoxy-quinolin-7-yloxy)-ethyl]-piperidin-4-yl}-amide Preparation of 2-methoxy-quinolin-7-ol 2-Chloro-quinolin-7-ol (4.2 g, 23.4 mmol, 1.0 eq) is added at room temperature to a stirred solution of sodium methoxide in methanol (15% weight, 200 mL, 561.6 mmol, 24.0 eq) and the resulting mixture is heated under reflux for 20 hours. Solvent is removed, the residue is dissolved in water (50 mL) and neutralized with acetic acid, followed by extraction with ethyl acetate (3×50 mL). The combined organic layers are dried over sodium sulfate, filtered and concentrated to give a crude product that is purified by column chromatography (silica gel, eluent: petroleum ether:ethyl acetate, 6:1, v/v) to afford 2-methoxy-quinolin-7-ol as a yellow solid (3.3 g, 79% yield).

$^1$H-NMR (400 MHz, DMSO-d$_6$) δ ppm: 9.99 (s, 1H), 8.03 (d, J=8.8 Hz, 1H), 7.66 (d, J=8.4 Hz, 1H), 7.01 (d, J=3.0 Hz, 1H), 6.93 (dd, J=2.0, 8.4 Hz, 1H), 6.72 (d, J=8.8 Hz, 1H), 3.91 (s, 3H).

MS m/z (+ESI): 176.1 [M+H]$^+$.

Preparation of 3-oxo-3,4-dihydro-2H-benzo[1,4]thiazine-6-carboxylic acid {1-[2-(2-methoxy-quinolin-7-yloxy)-ethyl]-piperidin-4-yl}-amide The title compound is prepared as a white lyophilizated powder following Scheme 1 and in analogy to Example 2 using 2-methoxy-quinolin-7-ol, [1-(2-hydroxy-ethyl)-piperidin-4-yl]-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.64 (s, 1H), 8.23 (d, J=7.5 Hz, 1H), 8.12 (m, 1H), 7.76 (d, J=8.8 Hz, 1H), 7.30-7.45 (m, 3H), 7.20 (d, J=2.5 Hz, 1H), 7.07 (dd, J=2.5, 8.8 Hz, 1H), 6.83 (d, J=8.8 Hz, 1H), 4.23 (t, J=5.6 Hz, 2H), 3.96 (s, 3H), 3.75 (m, 1H), 3.49 (s, 2H), 3.00 (m, 2H), 2.78 (t, J=5.6 Hz, 2H), 2.18 (m, 2H), 1.77 (m, 2H), 1.59 (m, 2H).

MS m/z (+ESI): 493.2 [M+H]$^+$.

Example 72

7-chloro-3-oxo-3,4-dihydro-2H-benzo[1,4]thiazine-6-carboxylic acid {1-[2-(7-cyano-quinoxalin-2-yloxy)-ethyl]-piperidin-4-yl}-amide Preparation of 3-chloro-quinoxaline-6-carbonitrile A solution of 3-oxo-3,4-dihydro-quinoxaline-6-carbonitrile (5.99 g, 35 mmol, 1.0 eq) in phosphorus oxychloride (26 mL, 280 mmol, 8.0 eq) is heated under reflux for 1 hour. Then the reaction mixture is cooled down to room temperature and the solvent is evaporated. The residue is poured into ice water, the resulting mixture is neutralized with sodium carbonate and extracted with ethyl acetate (3×50 mL). The combined organic layers are dried over sodium sulfate, filtered and concentrated to give a crude product that is purified by column chromatography (silica gel, eluent: dichloromethane 100%) to afford 3-chloro-quinoxaline-6-carbonitrile as a white solid (5.27 g, 79% yield).

$^1$H-NMR (400 MHz, DMSO-d$_6$) δ ppm: 9.14 (s, 1H), 8.69 (d, J=1.6 Hz, 1H), 8.29 (d, J=8.8 Hz, 1H), 8.19 (dd, J=1.6, 8.8 Hz, 1H).

MS m/z (+ESI): 190.2 [M+H]$^+$.

Preparation of 7-chloro-3-oxo-3,4-dihydro-2H-benzo[1,4]thiazine-6-carboxylic acid {1-[2-(7-cyano-quinoxalin-2-yloxy)-ethyl]-piperidin-4-yl}-amide The title compound is prepared as a yellow lyophilizated powder following Scheme 1 and in analogy to Example 1 using 3-chloro-quinoxaline-6-carbonitrile, [1-(2-hydroxy-ethyl)-piperidin-4-yl]-carbamic acid tert-butyl ester and 7-chloro-3-oxo-3,4-dihydro-2H-benzo[1,4]thiazine-6-carboxylic acid as starting materials.

$^1$H-NMR (400 MHz, DMSO-d$_6$) δ ppm: 10.61 (s, 1H), 8.77 (s, 1H), 8.39 (d, J=1.8 Hz, 1H), 8.32 (d, J=7.8 Hz, 1H), 8.17 (d, J=8.5 Hz, 1H), 7.97 (dd, J=1.8, 8.5 Hz, 1H), 7.48 (s, 1H), 6.92 (s, 1H), 4.57 (t, J=5.7 Hz, 2H), 3.71 (m, 1H), 3.51 (s, 2H), 2.97 (m, 2H), 2.78 (t, J=5.7 Hz, 2H), 2.17 (m, 2H), 1.78 (m, 2H), 1.45 (m, 2H).

MS m/z (+ESI): 523.2 [M+H]$^+$.

Example 73

6-({1-[2-(7-fluoro-6-methoxy-quinolin-3-yloxy)-ethyl]-piperidin-4-ylamino}-methyl)-4H-benzo[1,4]thiazin-3-one Preparation of 7-fluoro-6-methoxy-quinolin-3-ol A mixture of 7-fluoro-6-methoxy-quinolin-3-ylamine (prepared according to procedures described in FR2862301, 830 mg, 4.3 mmol, 1.0 eq) and concentrated hydrochloric acid (12N, 3.0 g, 30.2 mmol, 7.0 eq) is stirred at 4° C. before the addition of sodium nitrite (313 mg, 4.7 mmol, 1.1 eq) in water (24 mL). After 2 hours stirring at 4° C., the resulting mixture is added dropwise to a stirred solution of concentrated sulfuric acid (8.2 mL) and water (24 mL) at 90° C. within 10 minutes. After 1 hour stirring at 90° C. the reaction mixture is cooled down to room temperature, neutralized with sodium hydrogen carbonate and extracted with ethyl acetate (3×80 mL). The combined organic layers are dried over sodium sulfate, filtered and concentrated to give a crude product that is recrystallized in methanol to afford 7-fluoro-6-methoxy-quinolin-3-ol as an off-white solid (0.60 g, 72% yield).

$^1$H-NMR (400 MHz, DMSO-d$_6$) δ ppm: 10.21 (s, 1H), 8.42 (d, J=2.7 Hz, 1H), 7.64 (d, J=12.5 Hz, 1H), 7.48 (d, J=2.7 Hz, 1H), 7.40 (d, J=9.3 Hz, 1H), 3.97 (s, 3H).

MS m/z (+ESI): 194.1 [M+H]$^+$.

Preparation of 6-({1-[2-(7-fluoro-6-methoxy-quinolin-3-yloxy)-ethyl]-piperidin-4-ylamino}-methyl)-4H-benzo[1,4]thiazin-3-one The title compound is prepared as an off-white lyophilizated powder following Scheme 1 and in analogy to Examples 2 and 9 using 7-fluoro-6-methoxy-quinolin-3-ol, [1-(2-hydroxy-ethyl)-piperidin-4-yl]-carbamic acid tert-butyl ester and 3-oxo-3,4-dihydro-2H-benzo[1,4]thiazine-6-carbaldehyde as starting materials.

MS m/z (+ESI): 497.2 [M+H]$^+$.

Example 74

7-methoxy-2-(2-{trans-4-[3-oxo-3,4-dihydro-2H-benzo[1,4]thiazine-6-carbonyl)-amino]-cyclohexyl}-ethoxy)-quinoline-3-carboxylic acid Preparation of 7-methoxy-2-(2-{trans-4-[(3-oxo-3,4-dihydro-2H-benzo[1,4]thiazine-6-carbonyl)-amino]-cyclohexyl}-ethoxy)-quinoline-3-carboxylic acid methyl ester The title compound is prepared as a light brown solid following Scheme 1 and in analogy to Examples 1 and 28 using 2-chloro-7-methoxy-quinoline-3-carboxylic acid, [trans-4-(2-hydroxy-ethyl)-cyclohexyl]-carbamic acid tert-butyl ester and 3-oxo-3,4-dihydro-2H-benzo[1,4]thiazine-6-carboxylic acid as starting materials.

MS m/z (+ESI): 550.3 [M+H]$^+$.

Preparation of 7-methoxy-2-(2-{trans-4-[(3-oxo-3,4-dihydro-2H-benzo[1,4]thiazine-6-carbonyl)-amino]-cyclohexyl}-ethoxy)-quinoline-3-carboxylic acid Lithium hydroxide monohydrate (18 mg, 0.42 mmol, 1.5 eq) is added at room temperature to a stirred solution of 7-methoxy-2-(2-{trans-4-[(3-oxo-3,4-dihydro-2H-benzo[1,4]thiazine-6-carbonyl)-amino]-cyclohexyl}-ethoxy)-quinoline-3-carboxylic acid methyl ester (173 mg, 0.28 mmol, 1.0 eq) in a mixture of tetrahydrofuran/water (6 mL, 2:1, v/v). After stirring at room temperature for 15 hours, solvents are evaporated and the residue is acidified to pH 5 with 0.5N hydrochloric acid aqueous solution and the resulting aqueous layer is extracted with dichloromethane (3×10 mL). The combined organic layers are dried over sodium sulfate, filtered and concentrated to give a residue that is purified by preparative HPLC to afford 7-methoxy-2-(2-{trans-4-[(3-oxo-3,4-dihydro-2H-benzo[1,4]thiazine-6-carbonyl)-amino]-cyclohexyl}-ethoxy)-quinoline-3-carboxylic acid as an off-white lyophilizated powder (11 mg, 6% yield).

$^1$H-NMR (400 MHz, DMSO-d$_6$) δ ppm: 12.85 (br, 1H), 10.63 (s, 1H), 8.62 (s, 1H), 8.18 (d, J=7.9 Hz, 1H), 7.90 (d, J=8.9 Hz, 1H), 7.36-7.44 (m, 3H), 7.16 (d, J=2.5 Hz, 1H), 7.10 (dd, J=2.5, 9.1 Hz, 1H), 4.50 (t, J=6.6 Hz, 2H), 3.91 (s, 3H), 3.72 (m, 1H), 3.49 (s, 2H), 1.85 (m, 4H), 1.70 (m, 2H), 1.48 (m, 1H), 1.32 (m, 2H), 1.11 (m, 2H).

MS m/z (+ESI): 536.3 [M+H]$^+$.

Example 75

6-({1-[2-cyclopropyl-2-(7-methoxy-quinoxalin-2-yloxy)-ethyl]-piperidin-4-ylamino}-methyl)-4H-benzo[1,4]thiazin-3-one Preparation of [1-(2-cyclopropyl-2-oxo-ethyl)-piperidin-4-yl]-carbamic acid tert-butyl ester 2-Bromo-1-cyclopropyl-ethanone (244 mg, 1.44 mmol, 1.0 eq) is added at room temperature to a stirred solution of piperidin-4-yl-carbamic acid tert-butyl ester (300 mg, 1.44 mmol, 1.0 eq) in N,N-dimethylformamide (12 mL), followed by potassium carbonate (200 mg, 1.44 mmol, 1.0 eq). After 4 hours stirring at 60° C., solvent is evaporated and the residue is extracted with dichloromethane (3×30 mL) and water (30 mL). The combined organic layers are dried over sodium sulfate, filtered and concentrated to afford [1-(2-cyclopropyl-2-oxo-ethyl)-piperidin-4-yl]-carbamic acid tert-butyl ester as a light yellow solid (425 mg, 99% yield).

$^1$H-NMR (400 MHz, DMSO-d$_6$) δ ppm: 6.76 (d, J=7.7 Hz, 1H), 4.96 (d, J=13.1 Hz, 1H), 3.22 (s, 2H), 2.75 (m, 2H), 2.27 (m, 1H), 2.03 (m, 2H), 1.68 (m, 2H), 1.42 (m, 2H), 1.38 (s, 9H), 0.87 (m, 2H), 0.80 (m, 2H).

MS m/z (+ESI): 283.3 [M+H]$^+$.

Preparation of [1-(2-cyclopropyl-2-hydroxy-ethyl)-piperidin-4-yl]-carbamic acid tert-butyl ester Lithium aluminium hydride (1.0M solution in tetrahydrofuran, 1.41 mL, 1.41 mmol, 1.0 eq) is added at 0° C. to a stirred solution of [1-(2-cyclopropyl-2-oxo-ethyl)-piperidin-4-yl]-carbamic acid tert-butyl ester (420 mg, 1.41 mmol, 1.0 eq) in tetrahydrofuran (25 mL). After 2 hours stirring at 0° C., the reaction mixture is cautiously quenched with ice-water (5 mL). Tetrahydrofuran in evaporated and the crude is extracted with dichloromethane (3×30 mL) and water (30 mL). The combined organic layers are dried over sodium sulfate, filtered and concentrated to afford [1-(2-cyclopropyl-2-hydroxy-ethyl)-piperidin-4-yl]-carbamic acid tert-butyl ester as a white solid (373 mg, 84% yield).

¹H-NMR (400 MHz, DMSO-d₆) δ ppm: 6.73 (d, J=7.8 Hz, 1H), 4.12 (d, J=4.1 Hz, 1H), 3.18 (m, 1H), 3.03 (m, 1H), 2.78 (m, 2H), 2.30 (m, 2H), 1.90, 2.00 (2m, 2H), 1.62 (m, 2H), 1.39 (s, 9H), 1.36 (m, 2H), 0.77 (m, 1H), 0.32 (m, 2H), 0.17, 0.22 (2m, 2H).

MS m/z (+ESI): 285.3 [M+H]⁺.

Preparation of 6-({1-[2-cyclopropyl-2-(7-methoxy-quinoxalin-2-yloxy)-ethyl]-piperidin-4-ylamino}-methyl)-4H-benzo[1,4]thiazin-3-one The title compound is prepared as a white lyophilized powder following Scheme 1 and in analogy to Examples 1 and 9 using 2-chloro-7-methoxy-quinoxaline, [1-(2-cyclopropyl-2-hydroxy-ethyl)-piperidin-4-yl]-carbamic acid tert-butyl ester and 3-oxo-3,4-dihydro-2H-benzo[1,4]thiazine-6-carbaldehyde as starting materials.

¹H-NMR (400 MHz, DMSO-d₆) δ ppm: 10.47 (s, 1H), 8.36 (s, 1H), 7.86 (d, J=9.0 Hz, 1H), 7.20 (m, 2H), 7.13 (d, J=2.8 Hz, 1H), 6.88 (m, 2H), 5.06 (m, 1H), 3.90 (s, 3H), 3.59 (s, 2H), 3.40 (s, 2H), 2.99 (m, 1H), 2.78 (m, 2H), 2.60 (m, 1H), 2.30 (m, 1H), 1.90, 2.07 (2m, 2H), 1.68 (m, 2H), 1.14 (m, 2H), 0.98 (m, 1H), 0.57 (m, 1H), 1.47 (m, 2H), 1.38 (m, 1H).

MS m/z (+ESI): 520.2 [M+H]⁺.

Example 76

3-oxo-3,4-dihydro-2H-benzo[1,4]thiazine-6-carboxylic acid {1-[2-(7,8-dimethoxy-quinoxalin-2-ylsulfanyl)-ethyl]-piperidin-4-yl}-amide Preparation of 3,4-dimethoxy-2-nitro-benzoic acid Potassium permanganate (0.6 g, 3.8 mmol, 2.0 eq), is added at room temperature to a stirred solution of 3,4-dimethoxy-2-nitro-benzaldehyde (0.4 g, 1.9 mmol, 1.0 eq) in acetic acid (10 mL). After stirring overnight at room temperature, the reaction mixture is quenched with saturated sodium sulfite aqueous solution and extracted with ethyl acetate (3×20 mL). The combined organic layers are dried over sodium sulfate, filtered and concentrated to afford 3,4-dimethoxy-2-nitro-benzoic acid as a white solid (0.35 g, 81% yield).

¹H-NMR (400 MHz, Acetone-d₆) δ ppm: 7.86 (d, J=8.8 Hz, 1H), 7.34 (d, J=8.8 Hz, 1H), 4.06 (s, 3H), 3.89 (s, 3H).

MS m/z (−ESI): 226.1 μM-K.

Preparation of 3,4-dimethoxy-2-nitro-phenylamine

Thionyl chloride (10 mL, 137.4 mmol, 4.98 eq) is added at room temperature to a stirred solution of 3,4-dimethoxy-2-nitro-benzoic acid (6.26 g, 27.6 mmol, 1.0 eq) in 1,2-dichloroethane (100 mL). The reaction mixture is heated at 82° C. for 2 hours, then solvent is removed and the resulting crude acid chloride is dissolved in acetone (50 mL), cooled down to 5° C. before the addition of a solution of sodium azide (10.0 g, 154.0 mmol, 5.58 eq) in water (20 mL). After 1 hour stirring, the reaction mixture is poured into water (300 ml), the resulting white precipitate of acyl azide is filtered, washed with water, dissolved in acetic acid (300 mL) and water (30 mL). The mixture is heated at 118° C. for 2 hours, then solvents are evaporated, the residue is taken in warm ethanol and filtered. The filtrate is concentrated and the residue is purified by column chromatography (silica gel, eluent: hexane:ethyl acetate, 10:1 to 5:1, v/v) to afford 3,4-dimethoxy-2-nitro-phenylamine as a red solid (3.5 g, 64% yield).

¹H-NMR (400 MHz, Acetone-d₆) δ ppm: 7.08 (d, J=8.8 Hz, 1H), 6.67 (d, J=8.8 Hz, 1H), 5.11 (br, 2H), 3.89 (s, 3H), 3.81 (s, 3H).

MS m/z (+ESI): 199.1 [M+H]⁺.

Preparation of (3,4-dimethoxy-2-nitro-phenylamino)-acetic acid

Bromoacetic acid (0.876 g, 6.31 mmol, 0.5 eq) is added portionwise to 3,4-dimethoxy-2-nitro-phenylamine (2.5 g, 12.61 mmol, 1.0 eq) and the mixture is stirred at 58° C. for 16 hours. The reaction is then quenched by 25% ammonia in water and diluted with water. The solid is filtered off and washed with 10% ammonia in water. The combined solutions are acidified by concentrated hydrochloric acid and the resulting precipitate is collected by filtration, washed with water and dried under vacuum to afford (3,4-dimethoxy-2-nitro-phenylamino)-acetic acid as a red solid (1.1 g, 34% yield).

¹H-NMR (400 MHz, MeOH-d₄) δ ppm: 7.11 (d, J=9.2 Hz, 1H), 6.44 (d, J=9.2 Hz, 1H), 3.91 (s, 2H), 3.89 (s, 3H), 3.81 (s, 3H).

MS m/z (+ESI): 257.3 [M+H]⁺.

Preparation of 7,8-dimethoxy-3,4-dihydro-1H-quinoxalin-2-one

10% Palladium on activated carbon (0.22 g, 2.06 mmol, 0.48 eq) is added at room temperature to a stirred solution of (3,4-dimethoxy-2-nitro-phenylamino)-acetic acid (1.1 g, 4.29 mmol, 1.0 eq) in methanol (30 mL). The mixture is hydrogenated for 16 hours, then filtered through decalite. Solvent is removed to afford 7,8-dimethoxy-3,4-dihydro-1H-quinoxalin-2-one as an off-white solid (0.46 g, 52% yield).

¹H-NMR (400 MHz, Acetone-d₆) δ ppm: 6.53 (d, J=8.8 Hz, 1H), 6.41 (d, J=8.8 Hz, 1H), 4.55 (br, 2H), 3.81 (s, 2H), 3.77 (s, 3H), 3.73 (s, 3H).

MS m/z (+ESI): 209.2 [M+H]⁺.

Preparation of 7,8-dimethoxy-quinoxalin-2-one

Sodium hydroxide (0.18 g, 4.42 mmol, 2.0 eq) is added at room temperature to a stirred solution of 7,8-dimethoxy-3,4-dihydro-1H-quinoxalin-2-one (0.46 g, 2.21 mmol, 1.0 eq) in water (5 mL), followed by 3% hydrogen peroxide (5 mL, 14.69 mmol, 6.65 eq). The reaction mixture is heated under reflux for 3 hours, then acidified with acetic acid to pH 5. The precipitate is collected by filtration, dried under vacuum to afford 7,8-dimethoxy-quinoxalin-2-one as a brown solid (0.3 g, 65% yield).

¹H-NMR (400 MHz, Acetone-d₆) δ ppm: 7.92 (s, 1H), 7.50 (d, J=9.2 Hz, 1H), 7.07 (d, J=9.2 Hz, 1H), 3.99 (s, 3H), 3.92 (s, 3H).

MS m/z (+ESI): 207.2 [M+H]⁺.

Preparation of 2-chloro-7,8-dimethoxy-quinoxaline

A solution of 7,8-dimethoxy-quinoxalin-2-one (5.0 g, 24.25 mmol, 1.0 eq) in phosphorus oxychloride (25 mL, 268.21 mmol, 11.06 eq) is heated under reflux for 1 hour. Then the reaction mixture is cooled down to room temperature and the solvent is evaporated. The residue is poured into ice water, the resulting mixture is neutralized with saturated sodium hydrogen carbonate and extracted with ethyl acetate (3×50 mL). The combined organic layers are dried over sodium sulfate, filtered and concentrated to give a crude product that is purified by column chromatography (silica gel, eluent: hexane:ethyl acetate, 2:1 to 1:1, v/v) to afford 2-chloro-7,8-dimethoxy-quinoxaline as a light yellow solid (4.2 g, 77% yield).

$^1$H-NMR (400 MHz, Acetone-d$_6$) δ ppm: 8.70 (s, 1H), 7.86 (d, J=9.2 Hz, 1H), 7.78 (d, J=9.2 Hz, 1H), 4.07 (s, 3H), 4.02 (s, 3H).

MS m/z (+ESI): 225.1 [M+H]$^+$.

Preparation of 3-oxo-3,4-dihydro-2H-benzo[1,4] thiazine-6-carboxylic acid {1-[2-(7,8-dimethoxy-quinoxalin-2-ylsulfanyl)-ethyl]-piperidin-4-yl}-amide The title compound is prepared as a light brown solid following Scheme 3 and in analogy to Example 35 using 2-chloro-7,8-dimethoxy-quinoxaline, 2-mercaptoethanol, piperidin-4-yl-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.64 (br, 1H), 8.61 (s, 1H), 8.22 (d, J=7.8 Hz, 1H), 7.77 (d, J=9.3 Hz, 1H), 7.60 (d, J=9.3 Hz, 1H), 7.37-7.45 (m, 3H), 3.98 (s, 3H), 3.97 (s, 3H), 3.73 (m, 1H), 3.57 (s, 2H), 3.48 (m, 2H), 2.98 (m, 2H), 2.71 (m, 2H), 2.12 (m, 2H), 1.76 (m, 2H), 1.55 (m, 2H).

MS m/z (+ESI): 540.2 [M+H]$^+$.

Example 77

3-oxo-3,4-dihydro-2H-benzo[1,4]thiazine-6-carboxylic acid {1-[2-(4-ethoxy-6-methoxy-[1,5]naphthyridin-3-yloxy)-ethyl]-piperidin-4-yl}-amide Preparation of 3-bromo-6-methoxy-[1,5]naphthyridin-4-ol N-Bromosuccinimide (263 mg, 1.48 mmol, 1.3 eq) is added at 15° C. to a stirred solution of 6-methoxy-[1,5]naphthyridin-4-ol (200 mg, 1.14 mmol, 1.0 eq) in acetic acid (3 mL). After 30 minutes stirring at 15° C., the reaction mixture is allowed to come at room temperature and the resulting cake is filtered, washed with acetic acid and dried to afford 3-bromo-6-methoxy-[1,5]naphthyridin-4-ol as an off-white solid (280 mg, 97% yield).

$^1$H-NMR (400 MHz, DMSO-d$_6$) δ ppm: 12.90 (br, 1H), 8.45 (s, 1H), 7.97 (d, J=9.2 Hz, 1H), 7.20 (d, J=9.2 Hz, 1H), 3.93 (s, 3H).

MS m/z (+ESI): 255.0 [M+H]$^+$.

Preparation of 8-benzyloxy-7-bromo-2-methoxy-[1,5]naphthyridine

Diethyl azodicarboxylate (1.37 g, 7.84 mmol, 2.0 eq) is added at room temperature to a stirred solution of 3-bromo-6-methoxy-[1,5]naphthyridin-4-ol (1.0 g, 3.92 mmol, 1.0 eq), benzyl alcohol (640 mg, 5.88 mmol, 1.5 eq) and triphenylphosphine (2.05 g, 7.84 mmol, 2.0 eq) in tetrahydrofuran (25 mL). After 15 hours stirring at room temperature, tetrahydrofuran is evaporated and the resulting crude product is purified by column chromatography (silica gel, eluent: petroleum ether: ethyl acetate, 10:1, v/v) to afford 8-benzyloxy-7-bromo-2-methoxy-[1,5]naphthyridine as a white solid (1.0 g, 74% yield).

$^1$H-NMR (400 MHz, DMSO-d$_6$) δ ppm: 8.78 (s, 1H), 8.25 (d, J=9.6 Hz, 1H), 7.45-7.60 (m, 2H), 7.24-7.40 (m, 4H), 5.84 (s, 2H), 4.03 (s, 3H).

MS m/z (+ESI): 345.0 [M+H]$^+$.

Preparation of 4-benzyloxy-6-methoxy-[1,5]naphthyridin-3-ol

Tris(dibenzylideneacetone)dipalladium(0) (36 mg, 0.039 mmol, 0.02 eq) is added at room temperature to a stirred solution of 8-benzyloxy-7-bromo-2-methoxy-[1,5]naphthyridine (680 mg, 1.97 mmol, 1.0 eq) in water (10 mL), and dioxane (20 mL), followed by 4,5-bis(diphenylphosphino)-9,9-dimethylxanthene (47 mg, 0.099 mmol, 0.05 eq) and a solution of potassium hydroxide (220 mg, 3.94 mmol, 2.0 eq) in water (10 mL). After 6 hours stirring at 90° C., the reaction mixture is quenched with a 1N hydrochloric acid aqueous solution (4 mL) and extracted with ethyl acetate (3×10 mL). The combined organic layers are dried over sodium sulfate, filtered and concentrated to give a residue that is purified by column chromatography (silica gel, eluent: petroleum ether: ethyl acetate, 4:1, v/v) to afford 4-benzyloxy-6-methoxy-[1, 5]naphthyridin-3-ol as a light yellow solid (278 mg, 53% yield).

$^1$H-NMR (400 MHz, CDCl$_3$) δ ppm: 8.59 (s, 1H), 8.21 (d, J=8.8 Hz, 1H), 7.25-7.43 (m, 5H), 7.01 (d, J=8.8 Hz, 1H), 5.86 (s, 2H), 4.08 (s, 3H).

MS m/z (+ESI): 283.1 [M+H]$^+$.

Preparation of {1-[2-(4-benzyloxy-6-methoxy-[1,5] naphthyridin-3-yloxy)-ethyl]-piperidin-4-yl}-carbamic acid tert-butyl ester Diethyl azodicarboxylate (5.48 g, 31.46 mmol, 2.0 eq) is added at room temperature to a stirred solution of 4-benzyloxy-6-methoxy-[1,5]naphthyridin-3-ol (4.44 g, 15.73 mmol, 1.0 eq), [1-(2-hydroxy-ethyl)-piperidin-4-yl]-carbamic acid tert-butyl ester (5.76 g, 23.59 mmol, 1.5 eq) and triphenylphosphine (8.25 g, 31.46 mmol, 2.0 eq) in tetrahydrofuran (150 mL). After 15 hours stirring at room temperature, tetrahydrofuran is evaporated and the resulting crude product is purified by column chromatography (silica gel, eluent: ethyl acetate:methanol, 10:0 to 9:1, v/v) to afford {1-[2-(4-benzyloxy-6-methoxy-[1,5]naphthyridin-3-yloxy)-ethyl]-piperidin-4-yl}-carbamic acid tert-butyl ester as a light brown viscous oil (9.31 g, 88% yield).

$^1$H-NMR (400 MHz, CDCl$_3$) δ ppm: 8.51 (s, 1H), 8.05 (d, J=8.8 Hz, 1H), 7.47 (m, 2H), 7.28 (m, 3H), 6.93 (d, J=8.8 Hz, 2H), 5.59 (s, 2H), 4.60 (s, 1H), 4.23 (t, J=5.6 Hz, 2H), 4.01 (s, 3H), 3.38 (m, 1H), 2.85 (m, 2H), 2.73 (m, 2H), 2.15 (m, 2H), 1.85 (m, 2H), 1.38, (m, 11H).

MS m/z (+ESI): 509.2 [M+H]$^+$.

Preparation of {1-[2-(4-hydroxy-6-methoxy-[1,5] naphthyridin-3-yloxy)-ethyl]-piperidin-4-yl}-carbamic acid tert-butyl ester 10% Palladium on activated carbon (3.45 g, 3.29 mmol, 0.18 eq) is added at room temperature to a stirred solution of {1-[2-(4-benzyloxy-6-methoxy-[1,5]naphthyridin-3-yloxy)-ethyl]-piperidin-4-yl}-carbamic acid tert-butyl ester (9.3 g, 18.28 mmol, 1.0 eq) in methanol (100 mL). The mixture is hydrogenated for 7 hours, then filtered through decalite. Solvent is removed to afford {1-[2-(4-hydroxy-6-methoxy-[1,5] naphthyridin-3-yloxy)-ethyl]-piperidin-4-yl}-carbamic acid tert-butyl ester as an off-white solid (7.1 g, 91% yield).

$^1$H-NMR (400 MHz, DMSO-d$_6$) δ ppm: 8.20 (s, 1H), 8.11 (d, J=9.0 Hz, 1H), 7.17 (d, J=9.0 Hz, 1H), 7.07 (d, J=6.7 Hz, 1H), 4.28 (t, J=4.9 Hz, 2H), 3.97 (s, 3H), 3.51 (m, 1H), 3.40 (m, 2H), 3.22 (m, 2H), 2.98 (m, 2H), 1.95 (m, 2H), 1.74 (m, 2H), 1.39 (m, 9H).

MS m/z (+ESI): 419.4 [M+H]$^+$.

Preparation of 3-oxo-3,4-dihydro-2H-benzo[1,4]thiazine-6-carboxylic acid {1-[2-(4-hydroxy-6-methoxy-[1,5]naphthyridin-3-yloxy)-ethyl]-piperidin-4-yl}-amide The title compound is prepared as a white lyophilized powder following Scheme 1 and in analogy to Example 1 using {1-[2-(4-hydroxy-6-methoxy-[1,5]naphthyridin-3-yloxy)-ethyl]-piperidin-4-yl}-carbamic acid tert-butyl ester and 3-oxo-3,4-dihydro-2H-benzo[1,4]thiazine-6-carboxylic acid as starting materials.

$^1$H-NMR (400 MHz, DMSO-d$_6$) δ ppm: 10.65 (s, 1H), 8.32 (d, J=7.2 Hz, 1H), 8.01 (d, J=9.0 Hz, 1H), 7.38-7.49 (m, 4H), 7.10 (d, J=9.0 Hz, 1H), 4.18 (m, 2H), 3.98 (s, 3H), 3.79 (m, 1H), 3.50 (s, 2H), 3.05 (m, 2H), 2.70 (t, J=5.6 Hz, 2H), 2.22 (m, 2H), 1.81 (m, 2H), 1.67 (m, 2H).

MS m/z (+ESI): 510.6 [M+H]$^+$.

Preparation of 3-oxo-3,4-dihydro-2H-benzo[1,4]thiazine-6-carboxylic acid {1-[2-(4-ethoxy-6-methoxy-[1,5]naphthyridin-3-yloxy)-ethyl]-piperidin-4-yl}-amide Ethyl iodide (13 μL, 0.16 mmol, 1.0 eq) is added at room temperature to a stirred solution of 3-oxo-3,4-dihydro-2H-benzo[1,4]thiazine-6-carboxylic acid {1-[2-(4-hydroxy-6-methoxy-[1,5]naphthyridin-3-yloxy)-ethyl]-piperidin-4-yl}-amide (90 mg, 0.16 mmol, 1.0 eq) in N,N-dimethylformamide (4 mL), followed by potassium carbonate (22 mg, 0.16 mmol, 1.0 eq). After 3 hours stirring at room temperature, solvent is evaporated and the residue is extracted with dichloromethane (3×10 mL) and water (10 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid {1-[2-(4-ethoxy-6-methoxy-[1,5]naphthyridin-3-yloxy)-ethyl]-piperidin-4-yl}-amide as a white lyophilized powder (29 mg, 32% yield).

$^1$H-NMR (400 MHz, DMSO-d$_6$) δ ppm: 10.65 (s, 1H), 8.70 (s, 1H), 8.24 (d, J=7.6 Hz, 1H), 8.18 (d, J=9.0 Hz, 1H), 7.37-7.48 (m, 3H), 7.11 (d, J=9.0 Hz, 1H), 4.56 (q, J=7.0 Hz, 2H), 4.35 (t, J=5.5 Hz, 2H), 4.01 (s, 3H), 3.72 (m, 1H), 3.50 (s, 2H), 2.99 (m, 2H), 2.76 (t, J=5.5 Hz, 2H), 2.17 (m, 2H), 1.77 (m, 2H), 1.58 (m, 2H), 1.39 (t, J=7.0 Hz, 3H).

MS m/z (+ESI): 538.6 [M+H]$^+$.

The examples listed in the following table are prepared using procedures previously described:

| Expl./ Comp. | Reference Scheme | Reference for Preparation | 1H-NMR (400 MHz, DMSO-d6) δ ppm | MS m/z (+ESI) |
| --- | --- | --- | --- | --- |
| 78 | 1 | Example 1 WO2005066176 | — | 510.3 [M + H]$^+$ |
| 79 | 1 | Example 1 WO2004058144 | — | 510.4 [M + H]$^+$ |
| 80 | 1 | Example 1 WO2004058144 | 10.64 (s, 1H), 8.39 (s, 1H), 7.87 (d, J = 8.8 Hz, 1H), 7.74 (d, J = 7.2 Hz, 1H), 7.44 (m, 2H), 7.37 (d, J = 8.0 Hz, 1H), 7.21-7.25 (m, 2H), 4.53-4.57 (m, 2H), 3.90 (s, 3H), 3.84 (m, 1H), 3.76 (m, 1H), 3.48 (s, 2H), 2.90 (m, 1H), 2.87 (m, 1H), 2.80 (m, 2H), 2.38 (m, 1H), 2.25 (m, 1H), 1.53, 1.90 (2m, 2H) | 510.3 [M + H]$^+$ |
| 81 | 1 | Example 1 WO2005066176 | 10.64 (br, 1H), 8.40 (s,1H), 8.13 (m, 1H), 7.87 (d, J = 8.8 Hz, 1H), 7.45 (m, 2H), 7.37 (d, J = 8.0 Hz, 1H), 7.23 (m, 2H), 4.55 (m, 2H), 3.90 (s, 3H), 3.57 (m, 1H), 3.52 (m, 1H), 3.48 (s, 2H), 3.09 (m, 1H), 2.90 (m, 1H), 2.80 (m, 2H), 2.07 (m, 1H), 1.93 (m, 1H), 1.44, 1.77 (2m, 2H) | 510.4 [M + H]$^+$ |
| 82 | 1 | Example 58 | — | 538.2 [M + H]$^+$ |
| 83 | 1 | Example 58 | — | 575.1 [M + H]$^+$ |
| 84 | 1 | Example 58 | 10.64 (s, 1H), 8.61 (s, 1H), 8.21 (d, J = 7.7 Hz, 1H), 8.06 (d, J = 8.9 Hz, 1H), 7.64 (d, J = 2.5 Hz, 1H), 7.35-7.50 (m, 4H), 4.58 (t, J = 5.7 Hz, 2H), 4.40 (s, 2H), 3.72 (m, 1H), 3.50 (s, 2H), 3.42 (s, 3H), 2.99 (m, 2H), 2.78 (m, 2H), 2.15 (m, 2H), 1.75 (m, 2H), 1.55 (m, 2H) | 552.1 [M + H]$^+$ |
| 85 | 1 | Example 58 | — | 664.1 [M + H]$^+$ |
| 86 | 1 | Example 58 | — | 594.2 [M + H]$^+$ |
| 87 | 1 | Example 58 | — | 550.2 [M + H]$^+$ |
| 88 | 1 | Example 58 | — | 522.2 [M + H]$^+$ |
| 89 | 1 | Example 58 | 10.65 (s, 1H), 8.43 (s, 1H), 8.21 (d, J = 7.8 Hz, 1H), 7.90 (d, J = 9.8 Hz, 1H), 7.28-7.47 (m, 7H), 6.92-7.02 (m, 3H), 4.57 (t, J = 5.7 Hz, 2H), 4.50 (m, 2H), 4.38 (m, 2H), 3.74 (m, 1H), 3.49 (s, 2H), 2.99 (m, 2H), 2.78 (t, J = 5.7 Hz, 2H), 2.14 (m, 2H), 1.76 (m, 2H), 1.53 (m, 2H) | 600.2 [M + H]$^+$ |
| 90 | 1 | Example 58 | 10.64 (s, 1H), 8.41 (s, 1H), 8.21 (d, J = 7.7 Hz, 1H), 7.88 (d, J = 9.0 Hz, 1H), 7.37-7.43 (m, 3H), 7.24 (dd, J = 2.7, 9.0 Hz, 1H), 7.18 (d, J = 2.7 Hz, 1H), 4.76 (t, J = 5.3 Hz, 1H), 4.55 (t, J = | 594.2 [M + H]$^+$ |

| Expl./Comp. | Reference Scheme | Reference for Preparation | 1H-NMR (400 MHz, DMSO-d6) δ ppm | MS m/z (+ESI) |
|---|---|---|---|---|
| | | | 5.7 Hz, 2H), 4.19 (t, J = 6.5 Hz, 2H), 4.02 (m, 2H), 3.72 (m, 3H), 3.49 (s, 2H), 2.99 (m, 2H), 2.78 (t, J = 5.7 Hz, 2H), 2.14 (m, 2H), 2.00 (m, 2H), 1.89 (m, 1H), 1.76 (m, 2H), 1.53 (m, 2H), 1.34 (m, 1H) | |
| 91 | 1 | Example 58 | 10.64 (s, 1H), 8.40 (s, 1H), 8.21 (d, J = 7.7 Hz, 1H), 7.88 (d, J = 9.0 Hz, 1H), 7.36-7.45 (m, 3H), 7.24 (dd, J = 2.7, 9.0 Hz, 1H), 7.20 (d, J = 2.5 Hz, 1H), 4.55 (m, 3H), 4.20 (t, J = 6.4 Hz, 2H), 3.75 (m, 1H), 3.60 (m, 2H), 3.50 (s, 2H), 3.00 (m, 2H), 2.79 (t, J = 5.7 Hz, 2H), 2.13 (m, 2H), 1.92 (m, 2H), 1.78 (m, 2H), 1.55 (m, 2H) | 538.2 [M + H]+ |
| 92 | 1 | Example 58 | 10.64 (s, 1H), 8.42 (s, 1H), 8.21 (d, J = 7.7 Hz, 1H), 7.90 (d, J = 9.0 Hz, 1H), 7.36-7.45 (m, 3H), 7.24 (m, 2H), 4.55 (t, J = 6.0 Hz, 2H), 4.22 (t, J = 6.0 Hz, 2H), 3.75 (m, 1H), 3.50 (s, 2H), 2.98 (m, 2H), 2.78 (t, J = 6.0 Hz, 2H), 2.69 (t, J = 7.1 Hz, 2H), 2.12 (m, 4H), 1.75 (m, 2H), 1.53 (m, 2H) | 547.2 [M + H]+ |
| 93 | 1 | Example 58 | 10.65 (s, 1H), 8.40 (s, 1H), 8.21 (d, J = 7.5 Hz, 1H), 7.88 (d, J = 9.0 Hz, 1H), 7.36-7.46 (m, 3H), 7.25 (dd, J = 2.7, 9.0 Hz, 1H), 7.19 (d, J = 2.5 Hz, 1H), 4.55 (t, J = 5.7 Hz, 2H), 4.10 (t, J = 6.5 Hz, 2H), 3.74 (m, 1H), 3.49 (s, 2H), 3.00 (m, 2H), 2.78 (t, J = 5.7 Hz, 2H), 2.13 (m, 2H), 1.78 (m, 4H), 1.55 (m, 2H), 1.02 (t, J = 7.4 Hz, 3H) | 522.2 [M + H]+ |
| 94 | 1 | Example 1 | 10.63 (s, 1H), 8.35 (s, 1H), 8.15 (d, J = 7.7 Hz, 1H), 7.87 (d, J = 8.8 Hz, 1H), 7.34-7.43 (m, 3H), 7.23 (dd, J = 3.0, 9.0 Hz, 1H), 7.19 (d, J = 2.8 Hz, 1H), 5.58 (m, 1H), 3.91 (s, 3H), 3.71 (m, 1H), 3.48 (s, 2H), 2.88, 3.08 (2m, 2H), 2.58, 2.70 (2m, 2H), 2.11 (m, 2H), 1.70 (m, 2H), 1.48 (m, 2H), 1.37 (d, J = 6.2 Hz, 3H) | 508.1 [M + H]+ 530.1 [M + Na]+ |
| 95 | 1 | Example 1 | 10.63 (s, 1H), 8.44 (s, 1H), 8.17 (d, J = 7.8 Hz, 1H), 7.90 (d, J = 9.0 Hz, 1H), 7.34-7.42 (m, 3H), 7.27 (dd, J = 2.8, 9.0 Hz, 1H), 7.19 (d, J = 2.8 Hz, 1H), 5.71, 5.78 (2m, 1H), 4.71, 4.82 (2m, 2H), 3.91 (s, 3H), 3.70 (m, 1H), 3.50 (s, 2H), 3.03 (m, 2H), 2.70 (m, 2H), 2.18 (m, 2H), 1.73 (m, 2H), 1.47 (m, 2H) | 526.1 [M + H]+ |
| 96 | 1 | Example 1 Example 9 | 10.49 (s, 1H), 8.41 (s, 1H), 7.88 (d, J = 9.0 Hz, 1H), 7.23 (m, 3H), 6.92 (m, 2H), 5.98 (m, 1H), 5.20-5.40 (m, 2H), 3.92 (s, 3H), 3.70 (m, 1H), 3.65 (s, 2H), 3.41 (s, 2H), 2.86, 2.96 (2m, 2H), 2.60, 2.72 (2m, 2H), 2.35 (m, 1H), 2.05, 2.10 (2m, 2H), 1.72 (m, 2H), 1.11, 1.21 (2m, 2H) | 506.2 [M + H]+ |
| 97 | 1 | Example 1 | 10.63 (s, 1H), 8.38 (s, 1H), 8.14 (d, J = 7.8 Hz, 1H), 7.87 (d, J = 9.0 Hz, 1H), 7.33-7.42 (m, 3H), 7.23 (dd, J = 2.7, 9.0 Hz, 1H), 7.17 (d, J = 2.7 Hz, 1H), 5.51 (m, 1H), 3.91 (s, 3H), 3.70 (m, 1H), 3.49 (s, 2H), 2.92, 3.12 (2m, 2H), 2.58, 2.70 (2m, 2H), 2.09, 2.19 (2m, 2H), 1.82 (m, 1H), 1.70 (m, 3H), 1.34, 1.48 (2m, 2H), 0.95 (t, J= 7.5 Hz, 3H) | 522.2 [M + H]+ |
| 98 | 1 | Example 1 Example 9 WO2008093737 | 10.45 (s, 1H), 8.34 (s, 1H), 7.86 (d, J = 9.0 Hz, 1H), 7.15-7.38 (m, 7H), 7.04 (d, J = 2.8 Hz, 1H), 6.89 (s, 1H), 6.82 (d, J = 8.0 Hz, 1H), 4.68 (m, 1H), 4.50 (m, 1H), 4.19 (d, J = 13.5 Hz, 1H), 3.79 (s, 3H), 3.48-3.62 (m, 2H), 3.41 (s, 2H), 3.22 (m, 2H), 2.77 (m, 1H), 2.40 (m, 2H), 2.12 (m, 2H), 1.95 (m, 1H), 1.67-1.82 (m, 2H), 1.08, 1.47 (2m, 2H) | 570.3 [M + H]+ |
| 99 | 1 | Example 66 WO2005066176 | — | 524.3 [M + H]+ |
| 100 | 2 | Example 28 | 10.64 (s, 1H), 9.99 (br, 1H), 8.48 (d, J = 8.6 Hz, 1H), 8.10 (dd, J = 2.1, 8.6 Hz, 1H), 7.37-7.59 (m, 5H), 7.20 (dd, J = 1.5, 7.5 Hz, 1H), 5.75 (s, 1H), 4.24 (d, J = 6.5 Hz, 2H), 3.76 (m, 1H), 3.47 (s, 2H), 1.90 (m, 4H), 1.80 (m, 1H), 1.40 (m, 2H), 1.25 (m, 2H) | 492.1 [M + H]+ 514.1 [M + Na]+ |
| 101 | 2 | Example 28 | — | 540.1 [M + H]+ |

| Expl./ Comp. | Reference Scheme | Reference for Preparation | 1H-NMR (400 MHz, DMSO-d6) δ ppm | MS m/z (+ESI) |
|---|---|---|---|---|
| 102 | 3 | Example 35 Example 40 | 11.08 (br, 1H), 8.69 (d, J = 2.1 Hz, 1H) 8.20 (m, 1H), 8.03 (d, J = 2.0 Hz, 1H), 7.94 (s, 1H), 7.18 (d, J = 9.0 Hz, 1H), 4.00 (s, 3H), 3.81 (s, 2H), 3.57 (s, 2H), 3.30 (m, 2H), 2.86 (m, 2H), 2.62 (t, J = 6.9 Hz, 2H), 2.42 (m, 1H), 2.01 (m, 2H), 1.80 (m, 2H), 1.30 (m, 2H) | 531.2 [M + H]+ |
| 103 | 3 | Example 35 | 11.36 (br, 1H), 8.71 (d, J = 2.2, 1H), 8.23 (d, J = 9.0 Hz, 1H), 8.05 (d, J = 2.1 Hz, 1H), 7.83 (d, J = 8.3 Hz, 1H), 7.60 (d, J = 8.0 Hz, 1H), 7.46 (d, J = 8.0 Hz, 1H), 7.18 (d, J = 9.0 Hz, 1H), 4.74 (s, 2H), 4.01 (s, 3H), 3.75 (m, 1H), 3.30 (m, 2H), 2.88 (m, 2H), 2.67 (t, J = 6.8 Hz, 2H), 2.19 (m, 2H), 1.84 (m, 2H), 1.54 (m, 2H) | 495.3 [M + H]+ |
| 104 | 3 | Example 35 | 10.66 (s, 1H), 8.59 (s, 1H), 8.42 (t, J = 5.7 Hz, 1H), 7.78 (d, J = 9.1 Hz, 1H), 7.40-7.55 (m, 4H), 7.26 (d, J = 2.8 Hz, 1H), 3.92 (s, 3H), 3.48 (s, 2H), 3.42 (m, 2H), 3.13 (m, 2H), 2.84 (m, 2H), 2.65 (m, 2H), 2.02 (m, 1H), 1.81 (m, 2H), 1.62 (m, 2H), 1.41 (m, 1H), 0.94 (m, 1H) | 524.1 [M + H]+ |
| 105 | 3 | Example 9 Example 67 WO2005066176 | 10.50 (s, 1H), 8.59 (s, 1H), 7.88 (d, J = 9.0 Hz, 1H), 7.18-7.35 (m, 3H), 6.94 (m, 2H), 3.93 (s, 3H), 3.37-3.65 (m, 9H), 2.60-2.77 (m, 4H), 2.25 (m, 2H), 1.88 (m, 1H), 1.52 (m, 2H) | 526.5 [M + H]+ |
| 106 | 1 | Example 1 Example 63 | 10.62 (s, 1H), 8.39 (s, 1H), 8.14 (d, J = 7.8 Hz, 1H), 7.88 (d, J = 9.0 Hz, 1H), 7.33-7.42 (m, 3H), 7.25 (dd, J = 2.7, 9.0 Hz, 1H), 7.18 (d, J = 2.7 Hz, 1H), 5.67 (m, 1H), 3.91 (s, 3H), 3.68 (m, 3H), 3.42-3.55 (m, 4H), 2.92, 3.07 (2m, 2H), 2.58-2.72 (m, 2H), 2.09, 2.18 (2m, 2H), 1.70 (m, 2H), 1.37, 1.48 (2m, 2H), 1.08 (t, J = 7.0 Hz, 3H) | 552.2 [M + H]+ |
| 107 | 1 | Example 1 Example 64 | 10.63 (br, 1H), 8.40 (s, 1H), 8.14 (d, J = 7.8 Hz, 1H), 7.88 (d, J = 9.0 Hz, 1H), 7.18-7.42 (m, 10H), 5.73 (m, 1H), 4.54 (q, J = 12.2 Hz, 2H), 3.91 (s, 3H), 3.63-3.80 (m, 3H), 3.49 (s, 2H), 2.95, 3.04 (2m, 2H), 2.70 (m, 2H), 2.09, 2.18 (2m, 2H), 1.70 (m, 2H), 1.38, 1.49 (2m, 2H) | 614.7 [M + H]+ |
| 108 | 1 | Example 1 Example 64 | 10.63 (br, 1H), 8.39 (s, 1H), 8.14 (d, J = 7.5 Hz, 1H), 7.88 (d, J = 9.0 Hz, 1H), 7.35-7.42 (m, 3H), 7.25 (dd, J = 2.8, 9.0 Hz, 1H), 7.18 (d, J = 2.8 Hz, 1H), 5.68 (m, 1H), 4.02 (q, J = 9.5 Hz, 2H), 3.91 (s, 3H), 3.75 (m, 2H), 3.55-3.72 (m, 5H), 3.48 (s, 2H), 2.94, 3.05 (2m, 2H), 2.65 (m, 2H), 2.09, 2.18 (2m, 2H), 1.70 (m, 2H), 1.38, 1.49 (2m, 2H) | 650.7 [M + H]+ |
| 109 | 1 | Example 1 Example 64 | 10.63 (br, 1H), 8.41 (s, 1H), 8.16 (d, J =7.7 Hz, 1H), 7.89 (d, J = 9.0 Hz, 1H), 7.33-7.44 (m, 3H), 7.26 (dd, J = 2.8, 9.0 Hz, 1H), 7.18 (d, J = 2.8 Hz, 1H), 5.68 (m, 1H), 4.15 (m, 2H), 3.97 (m, 2H), 3.91 (s, 3H), 3.71 (m, 1H), 3.48 (s, 2H), 2.94, 3.05 (2m, 2H), 2.65 (m, 2H), 2.09, 2.18 (2m, 2H), 1.70 (m, 2H), 1.38, 1.49 (2m, 2H) | 606.7 [M + H]+ |
| 110 | 1 | Example 1 Example 9 | 8.40 (s, 1H), 7.88 (d, J = 9.0 Hz, 1H), 7.20-7.33 (m, 6H), 4.52 (t, J = 5.9 Hz, 2H), 3.92 (s, 3H, 3.80 (S, 2H), 2.90 (m, 2H), 2.75 (t, J = 5.9 Hz, 2H), 2.45 (m, 1H), 2.06 (m, 2H), 1.82 (m, 2H), 1.16-1.30 (m, 11H) | 449.3 [M + H]+ |
| 111 | 1 | Example 1 | 10.92 (s, 1H), 8.40 (m, 2H), 7.89 (d, J = 9.0 Hz, 1H), 7.73 (s, 1H), 7.25 (m, 2H), 6.99 (s, 1H), 4.55 (t, J = 5.7 Hz, 2H), 3.94 (s, 3H), 3.71 (m, 1H), 3.47 (s, 2H), 2.96 (m, 2H), 2.79 (t, J = 5.7 Hz, 2H), 2.17 (m, 2H), 1.77 (m, 2H), 1.40-1.50 (m, 2H) | 562.3 [M + H]+ |
| 112 | 1 | Example 1 | 8.42 (s, 1H), 8.35 (d, J = 7.7 Hz, 1H), 8.11 (d, J = 0.5 Hz, 1H), 7.89 (d, J = 9.0 Hz, 1H), 7.83 (d, J =5.3 Hz, 1H), 7.48 (dd, J = 0.5, 5.3 Hz, 1H), 7.26 (m, 2H), 4.57 (t, J = 5.8 Hz, 2H), 3.94 (s, 3H), 3.75 (m, 1H), 3.02 (m, 2H), 2.81 (t, J = 5.8 Hz, 2H), 2.18 (m, 2H), 1.81 (m, 2H), 1.50-1.62 (m, 2H) | 469.3 [M + H]+ |
| 113 | 2 | Example 29 | — | 437.5 [M + H]+ |
| 114 | 2 | Example 29 | — | 473.2 [M + H]+ |

-continued

| Expl./Comp. | Reference Scheme | Reference for Preparation | 1H-NMR (400 MHz, DMSO-d6) δ ppm | MS m/z (+ESI) |
|---|---|---|---|---|
| 115 | 2 | Example 29 | 9.13 (d, J = 2.0 Hz, 1H), 8.87 (d, J = 2.0 Hz, 1H), 7.99 (d, J = 8.8 Hz, 1H), 7.68 (m, 2H), 7.53 (dd, J = 2.8, 8.8 Hz, 1H), 7.46 (d, J = 12.0 Hz, 1H), 7.38 (d, J = 8.0 Hz, 1H), 4.15 (d, J = 6.4 Hz, 2H), 3.90 (s, 3H), 3.82 (s, 2H), 2.31 (m, 1H), 1.83-1.95 (m, 4H), 1.65-1.80 (m, 1H), 1.07 (m, 4H) | 491.4 [M + H]+ |
| 116 | 2 | Example 29 | 9.14 (d, J = 2.0 Hz, 1H), 8.87 (d, J = 2.0 Hz, 1H), 7.99 (d, J = 9.2 Hz, 1H), 7.64 (d, J = 2.8 Hz, 1H), 7.48 (dd, J = 2.8, 9.2 Hz, 1H), 7.38 (m, 2H), 7.29 (m, 2H), 7.19 (t, J = 7.2 Hz, 1H), 6.50 (d, J = 16.4 Hz, 1H), 6.29-6.34 (m, 1H), 4.17 (d, J = 6.4 Hz, 2H), 3.90 (s, 3H), 3.38 (m, 2H), 2.39 (m, 1H), 1.81-1.94 (m, 4H), 1.73 (m, 1H), 1.07 (m, 4H) | 431.3 [M + H]+ |
| 117 | 2 | Example 29 | 9.13 (d, J = 2.0 Hz, 1H), 8.88 (d, J = 2.0 Hz, 1H), 8.00 (d, J = 9.2 Hz, 1H), 7.63 (d, J = 2.4 Hz, 1H), 7.55 (dd, J = 2.8, 9.2 Hz, 1H), 7.25 (m, 2H), 7.14 (m, 2H), 4.17 (d, J = 6.8 Hz, 2H), 3.90 (s, 3H), 3.82 (m, 2H), 2.48 (m, 1H), 2.27 (s, 3H), 1.85-2.01 (m, 4H), 1.75 (m, 1H), 1.07-1.19 (m, 4H) | 419.2 [M + H]+ |
| 118 | 2 | Example 29 | — | 461.1 [M + H]+ |
| 119 | 2 | Example 29 | 9.13 (d, J = 1.6 Hz, 1H), 8.86 (d, J = 1.6 Hz, 1H), 7.99 (d, J = 9.2 Hz, 1H), 7.83 (m, 4H), 7.63 (d, J = 2.8 Hz, 1H), 7.42-7.54 (m, 4H), 4.15 (d, J = 6.8 Hz, 2H), 3.90 (s, 3H), 2.39 (m, 1H), 1.83-2.00 (m, 4H), 1.70 (m, 1H), 1.05-1.12 (m, 4H) | 455.3 [M + H]+ |
| 120 | 2 | Example 29 | 9.14 (d, J = 2.0 Hz, 1H), 8.87 (d, J = 2.0 Hz, 1H), 7.99 (d, J = 9.2 Hz, 1H), 7.64 (s, 1H), 7.53 (dd, J = 2.8, 9.2 Hz, 1H), 7.14-7.27 (m, 5H), 4.17 (d, J = 6.8 Hz, 2H), 3.90 (s, 3H), 2.58 (m, 4H), 2.38 (m, 1H), 1.83-1.90 (m, 4H), 1.69 (m, 3H), 1.02-1.12 (m, 4H) | 433.3 [M + H]+ |
| 121 | 2 | Example 29 | 9.29 (d, J = 2.0 Hz, 1H), 8.72 (d, J = 2.0 Hz, 1H), 8.04 (d, J = 9.6 Hz, 1H), 7.61 (s, 1H), 7.59 (d, J = 11.2 Hz, 1H), 7.46 (m, 2H), 7.29 (s, 1H), 7.17 (s, 1H), 6.74 (s, 1H), 4.22 (d, J = 6.8 Hz, 2H), 3.95 (s, 3H), 3.93 (s, 2H), 2.57 (m, 1H), 1.93-2.05 (m, 4H), 1.80-1.88 (m, 1H), 1.13-1.25 (m, 4H) | 445.2 [M + H]+ |
| 122 | 3 | Example 35 | 8.62 (s, 1H), 7.98 (d, J = 7.8 Hz, 1H), 7.90 (d, J = 9.1 Hz, 1H), 7.35 (dd, J = 2.8, 9.1 Hz, 1H), 7.28 (d, J = 2.8 Hz, 1H), 7.00 (d, J = 1.6 Hz, 1H), 6.93 (m, 2H), 6.19 (br, 1H), 3.94 (s, 3H), 3.73 (m, 1H), 3.48 (m, 4H), 3.00 (m, 4H), 2.72 (t, J = 6.8 Hz, 2H), 2.14 (m, 2H), 1.76 (m, 2H), 1.58 (m, 2H) | 496.3 [M + H]+ |
| 123 | 1 | Example 1 Example 9 | 8.40 (s, 1H), 7.89 (d, J = 9.0 Hz, 1H), 7.25 (d, J = 9.0 Hz, 1H), 7.22 (s, 1H), 6.91 (s, 1H), 6.78 (m, 2H), 5.97 (s, 2H), 4.52 (t, J = 5.6 Hz, 2H), 3.92 (s, 3H), 3.61 (s, 2H), 2.88 (m, 2H), 2.74 (t, J = 5.6 Hz, 2H), 2.32 (m, 1H), 2.02 (m, 2H), 1.76 (m, 2H), 1.24 (m, 2H) | 437.3 [M + H]+ |

Anti-Microbial Activity Assay.

The antibacterial activity of compounds is determined by the minimal inhibitory concentration (MIC) method. MICs for all bacteria except pneumococci and *Haemophilus influenzae* are obtained by broth microdilution with cation-adjusted Mueller-Hinton broth (CAMHB; BBL), according to CLSI guidelines (National Committee for Clinical Laboratory Standards. 2003. Methods for dilution antimicrobial susceptibility tests for bacteria that grow aerobically, 5$^{th}$ ed.; approved standard M7-A6. National Committee for Clinical Laboratory Standards, Wayne, Pa.), with the following modifications: (i) for pneumococci CAMHB is supplemented with 5% (v/v) horse serum; (ii) for *Haemophilus influenzae* CAMHB is supplemented with 5% (v/v) Fildes enrichment (BBL) (Pankuch, G. A., Hoellman, D. B., Lin, G., Bajaksouzian, S., Jacobs, M. R., and Appelbaum, P. C. 1998. Activity of HMR 3647 compared to those of five agents against *Haemophilus influenzae* and *Moraxella catarrhalis* by MIC determination and time-kill assay. Antimicrob. Agents Chemother. 42:3032-3034). Microtiter plates are incubated at 35° C. in ambient air for 20 to 24 h, then inspected using an illuminated microtiter plate reader fitted with a magnifying mirror (MIC 2000; Cooke Laboratory Products, Alexandria, Va.). Compounds of the present invention are tested against several bacteria strains comprising some *Acinetobacter baumannii, Enterococcus faecalis, Enterococcus faecium, Escherichia coli, Haemophilus influenzae, Klebsiella pneumoniae, Pseudomonas aeruginosa, Staphylococcus aureus, Staphylococcus epidermidis* and *Streptococcus pneumoniae*. The MIC values (in mg/L) for the Examples 1 to 56 are presented in Table 2.

TABLE 2

| Example/ Compound | Staphylococcus aureus ATCC29213 MIC (mg/L) | Staphylococcus epidermidis ATCC14990 MIC (mg/L) | Streptococcus pneumoniae ATCC49619 MIC (mg/L) | Escherichia coli UB1005 MIC (mg/L) |
|---|---|---|---|---|
| 1 | ≤2 | ≤2 | 4 | 8 |
| 2 | 2 | ≤2 | ≤2 | >32 |
| 3 | ≤2 | ≤2 | 16 | >32 |
| 4 | ≤2 | ≤2 | >32 | >32 |
| 5 | ≤2 | ≤2 | ≤2 | >32 |
| 6 | ≤2 | ≤2 | 4 | >32 |
| 7 | ≤2 | >32 | >32 | >32 |
| 8 | ≤2 | 4 | 16 | 16 |
| 9 | ≤2 | 4 | ≤2 | 4 |
| 10 | 4 | 8 | 8 | >32 |
| 11 | 4 | 4 | 4 | 16 |
| 12 | 4 | 4 | 16 | ≥32 |
| 13 | 4 | >32 | >32 | >32 |
| 14 | ≤2 | 8 | 8 | >32 |
| 15 | ≤2 | ≤2 | 8 | 4 |
| 16 | ≤2 | 4 | 8 | 8 |
| 17 | ≤2 | 4 | 16 | >32 |
| 18 | ≤2 | ≤2 | 4 | 8 |
| 19 | ≤2 | ≤2 | 8 | 4 |
| 20 | ≤2 | ≤2 | >32 | >32 |
| 21 | 8 | 16 | >32 | ≥32 |
| 22 | 4 | 4 | 32 | 16 |
| 23 | 4 | 4 | 16 | 16 |
| 24 | 8 | 8 | 16 | 4 |
| 25 | 8 | 16 | 16 | 8 |
| 26 | 4 | 16 | 8 | >32 |
| 27 | 8 | 32 | 32 | 16 |
| 28 | ≤2 | ≤2 | >32 | >32 |
| 29 | ≤2 | ≤2 | 4 | >32 |
| 30 | ≤2 | 4 | >32 | >32 |
| 31 | ≤2 | 4 | 8 | >32 |
| 32 | 8 | 16 | 32 | >32 |
| 33 | 4 | 8 | 8 | >32 |
| 34 | 8 | >32 | >32 | >32 |
| 35 | ≤2 | ≤2 | ≤2 | >32 |
| 36 | ≤2 | ≤2 | ≤2 | 4 |
| 37 | ≤2 | ≤2 | ≤2 | ≤2 |
| 38 | ≤2 | ≤2 | ≤2 | 16 |
| 39 | ≤2 | ≤2 | ≤2 | ≥32 |
| 40 | ≤2 | ≤2 | ≤2 | ≤2 |
| 41 | ≤2 | ≤2 | ≤2 | 8 |
| 42 | ≤2 | ≤2 | ≤2 | 8 |
| 43 | ≤2 | ≤2 | ≤2 | 16 |
| 44 | ≤2 | ≤2 | 4 | 4 |
| 45 | ≤2 | ≤2 | ≤2 | ≤2 |
| 46 | ≤2 | ≤2 | ≤2 | ≤2 |
| 47 | ≤2 | ≤2 | ≤2 | 32 |
| 48 | ≤2 | ≤2 | ≤2 | ≤2 |
| 49 | ≤2 | ≤2 | ≤2 | 4 |
| 50 | ≤2 | ≤2 | ≤2 | 4 |
| 51 | ≤2 | ≤2 | 4 | 4 |
| 52 | ≤2 | ≤2 | ≤2 | 16 |
| 53 | ≤2 | ≤2 | ≤2 | 4 |
| 54 | ≤2 | ≤2 | 4 | 4 |
| 55 | ≤2 | ≤2 | ≤2 | 16 |
| 56 | ≤2 | 4 | 16 | 4 |

The other described example compounds have a MIC for *Staphylococcus aureus* ATCC29213 of less or equal to 8 mg/L.

What is claimed is:

1. A compound of formula I

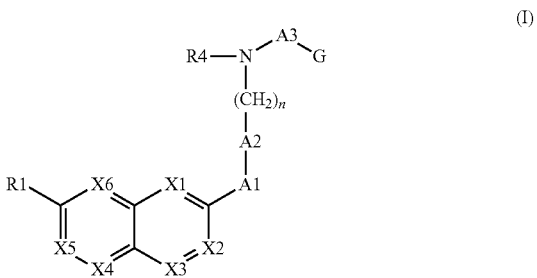

wherein

X1, X3; X4 and X6, each independently of the others, represents a nitrogen atom or CR2, with the proviso that at least one of X1, X3; X4 and X6 represents a nitrogen atom;

X2 represents C—H, C—(C1-C6alkyl), C—(C1-C6alkoxy), C-halogen, C—COOH;

X5 represents C—H or C—(C1-C6alkyl), C-halogen;

R1 and R2, independently of one another, represent hydrogen or a substituent selected from hydroxy, halogen, carboxy, amino, C1-C6alkylamino, di(C1-C6alkyl)amino, mercapto, cyano, nitro, C1-C6alkyl, C1-C6alkoxy, C1-C6alkylthio, C1-C6alkylamino-carbonyloxy, C2-C6alkenyl, C2-C6alkynyl, C1-C6alkylcarbonyloxy, C1-C6alkyl-sulfonyloxy, C1-C6heteroalkylcarbonyloxy, $C_5$-$C_6$heterocyclylcarbonyloxy, C1-C6heteroalkyl, C1-C6heteroalkoxy, wherein heteroalkyl, heteroalkoxy groups or heterocyclyl comprise 1, 2 or 3 heteroatoms selected from nitrogen, oxygen and sulphur, in which substituents the alkyl moieties are unsubstituted or further substituted by halogeno, cyano, hydroxy, C1-C4alkoxy, C1-C4alkylcarbonyl, C1-C4alkoxycarbonyl, unsubstituted or substituted phenoxy or phenylcarbonyl, unsubstituted or substituted C5-C6heterocyclyl or carboxy;

A1 represents a divalent group of one of the formulae —O—$(CH_2)_m$—$(CH_2)$—, —S—$(CH_2)_m$—$(CH_2)$— or —(C═O)O—$(CH_2)_m$—$(CH_2)$—, wherein the $(CH_2)_m$ moiety is optionally substituted by C1-C4alkyl, C2-C4alkenyl, C3-C6cycloalkyl, C3-C6cycloalkylmethyl, morpholinomethyl, halogen, carboxy, hydroxy, C1-C4alkoxy;

C1-C4alkoxyC1-C4alkyl, C1-C4alkoxy(C1-C4alkylenoxy)C1-C4alkyl, benzyloxyC1-C4alkyl, amino, mono- or di-(C1-C4alkyl)amino or acylamino, in which substituents the alkyl moieties can be further substituted by i or more fluoro atoms m is 0, 1 or 2, provided that the number of atoms in the direct chain between the two terminal valencies of A1 is at least 3, which group A1 is linked to A2 via the terminal $(CH_2)$-moiety;

A2 is a group selected from C3-C8cycloalkylene; saturated and unsaturated 4 to 8-membered heterocyclodiyl with 1, 2 or 3 heteroatoms selected from nitrogen, oxygen and sulphur, which group A2 is unsubstituted or substituted by one or more substituents selected from the group consisting of carboxy, amino, mono- or di(C1-C4alkyl)amino, halogeno, cyano, hydroxy, mercapto, C1-C4alkoxy, C1-C4alkylcarbonyl, C1-C4alkoxycarbonyl, unsubstituted phenoxy or phenylcarbonyl, unsubstituted C5-C6heterocyclyl, ═O, ═S, ═NH and $NO_2$;

R4 represents hydrogen or C1-C4alkyl;

A3 represents C1-C4alkylene, C2-C4alkenylene, >C=O, —C(O)C1-C3alkylene-, —C(=O)NH—, or a group selected from —C₂H₄NH—, —C₂H₄O—, and —C₂H₄S— being linked to the adjacent NR₄-group via the carbon atom; and G represents benzo[1,4]thiazine or pyrido[1,4]thiazine which are unsubstituted or substituted by one or more substituents selected from the group consisting of alkyl, fluorine, chlorine, bromine or iodine, carboxy, alkoxy, NH2, mono- or di(C1-C4alkyl)amino, OH, cyano and NO₂, =O, SH, =S and =NH; and n is 0, 1 or 2;

or a pharmaceutically acceptable salt, a hydrate or solvate thereof.

2. The compound of claim 1, wherein either X1 alone, X3 alone, X4 alone or X6 alone or either X3 and X1 or X3 and X6 or X1 and X4 represent nitrogen.

3. The compound of claim 1, wherein

R1 is selected from hydrogen, hydroxy, mercapto, cyano, nitro, C1-C6alkylsulfonyloxy, C1-C6alkylcarbonyloxy, C1-C6heteroalkylcarbonyloxy, C5-C6heteroarylcarbonyloxy and, more preferably from halogen, in particular fluoro, and C1-C6alkoxy, preferably C1-C4alkoxy, in particular methoxy.

4. The compound of claim 1, wherein

A2 represents a group selected from C5-C6cycloalkylene and saturated or unsaturated 4 to 6-membered heterocyclodiyl with one or two nitrogen atoms as the heteroatom(s), in particular unsubstitued C5-C6cycloalkylene and saturated 4 to 6-membered heterocyclodiyl with one nitrogen atom as the heteroatom.

5. The compound of claim 4 wherein

A2 is selected from the group consisting of:

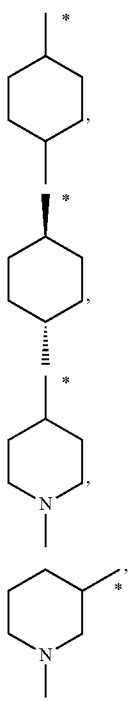

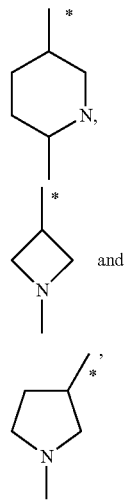

wherein

* indicates the bond to the (CH₂)ₙ group in formula (I).

6. The compound of claim 1 wherein

A1 represents —O—(CH₂)ₘ—(CH₂)— or —S—(CH₂)ₘ—(CH₂)— and m is as claimed in claim 1.

7. The compound of claim 6 wherein m is 1.

8. The compound of claim 1 wherein n is 0 or 1.

9. The compound of claim 1, wherein

G is selected from a group of formula:

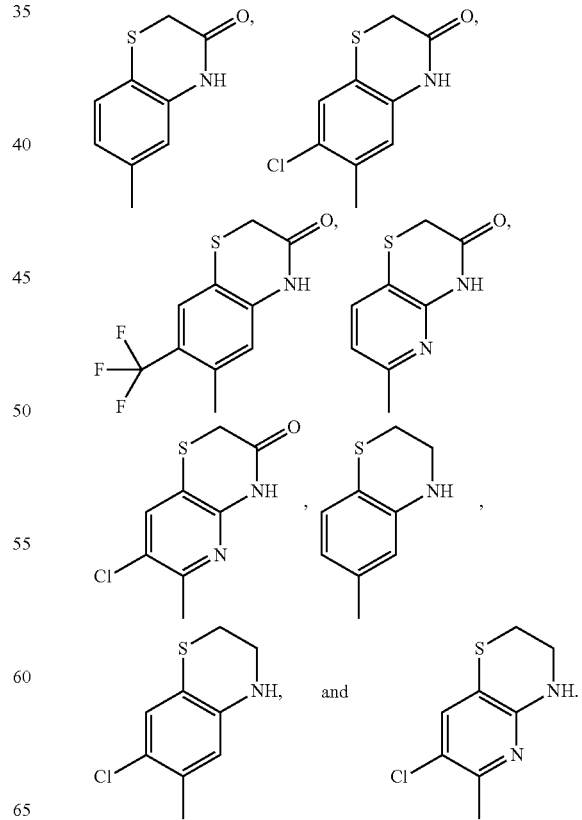

10. The compound of claim 1, wherein R2 is selected from hydrogen, hydroxy, halogen, C1-C6alkyl, C1-C6alkoxy, carboxy.

11. The compound of claim 4 wherein A2 is unsubstituted or substituted with a group selected from hydroxy, C1-C4alkyl and carboxy.

12. The compound of claim 7 wherein $(CH_2)_m$ is unsubstituted of substituted with groups selected from C1-C6alkyl and C1-C6alkenyl.

13. A pharmaceutical composition comprising a compound of claim 1 or a pharmaceutically acceptable salt, a hydrate or a solvate thereof.

14. A pharmaceutical composition as claimed in claim 13 for treatment of bacterial infections.

15. The pharmaceutical composition of claim 13 further comprising a pharmaceutically acceptable carrier.

16. The compound of claim 1 which is 3-oxo-3,4-dihydro-2H-benzo[1,4]thiazine-6-carboxylic acid {trans-4-[2-(6-methoxy-[1,5]naphthyridin-3-yloxy)-ethyl-cyclohexyl}-amide or a pharmaceutically acceptable salt, a hydrate or solvate thereof.

17. The compound of claim 1 which is 7-chloro-3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-amide or a pharmaceutically acceptable salt, a hydrate or solvate thereof.

18. The compound of claim 1 which is 3-oxo-3,4-dihydro-2H-pyrido[3,2-b][1,4]thiazine-6-carboxylic acid {1-[2-(7-methoxy-quinoxalin-2-ylsulfanyl)-ethyl]piperidin-4-yl}-amide or a pharmaceutically acceptable salt, a hydrate or solvate thereof.

19. The compound of claim 1 which is 3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide or a pharmaceutically acceptable salt, a hydrate or solvate thereof.

20. The compound of claim 1 which is 3-oxo-3,4-dihydro-2H-pyrido[3,2-b][1,4]thiazine-6-carboxylic acid {1-[2-(6-methoxy-quinolin-3-ylsulfanyl)-ethyl]-piperidin-4-yl}-amide or a pharmaceutically acceptable salt, a hydrate or solvate thereof.

21. The compound of claim 1 which is 3-oxo-3,4-dihydro-2H-benzo[1,4]thiazine-6-carboxylic acid {(R)-3-hydroxy-1-[2-(7-methoxy-quinoxalin-2-yloxy)-ethyl]-piperidin-4-yl}-amide or a pharmaceutically acceptable salt, a hydrate or solvate thereof.

22. The compound of claim 1 which is 3-oxo-3,4-dihydro-2H-benzo[1,4]thiazine-6-carboxylic acid {1-[2-(7-methoxy-quinoxalin-2-ylsulfanyl)-ethyl]-piperidin-3-ylmethyl}-amide or a pharmaceutically acceptable salt, a hydrate or solvate thereof.

23. The compound of claim 1, wherein said compound is selected from the group consisting of 3-oxo-3,4-dihydro-2H-benzo[1,4]thiazine-6-carboxylic acid {1-[2-(7-methoxy-quinoxalin-2-yloxy)-ethyl]-piperidin-4-yl}-amide;

3-oxo-3,4-dihydro-2H-benzo[1,4]thiazine-6-carboxylic acid {trans-4-[2-(6-methoxy-[1,5]naphthyridin-3-yloxy)-ethyl]-cyclohexyl}-amide;

3-oxo-3,4-dihydro-2H-benzo[1,4]thiazine-6-carboxylic acid {trans-4[-2-(7-methoxy-quinoxalin-2-yloxy)-ethyl]-cyclohexyl}-amide;

3-oxo-3,4-dihydro-2H-benzo[1,4]thiazine-6-carboxylic acid {trans-4[-2-(7-fluoro-quinoxalin-2-yloxy)-ethyl]-cyclohexyl}-amide;

3-oxo-3,4-dihydro-2H-benzo[1,4]thiazine-6-carboxylic acid {1-[3-(7-methoxy-quinoxalin-2-yloxy)-propyl]-azetidin-3-yl}-amide;

3-oxo-3,4-dihydro-2H-benzo[1,4]thiazine-6-carboxylic acid {1-[3,3,3-trifluoro-2-(7-methoxy-quinoxalin-2-yloxy)-propyl]-piperidin-4-yl}-amide;

7-chloro-3-oxo-3,4-dihydro-2H-benzo[1,4]thiazine-6-carboxylic acid {1-[2-(7-methoxy-quinoxalin-2-yloxy)-ethyl]-piperidin-4-yl}-amide;

7-chloro-3-oxo-3,4-dihydro-2H-benzo[1,4]thiazine-6-carboxylic acid {1-[2-(6-methoxy-[1,5]naphthyridin-3-yloxy)-ethyl]-piperidin-4-yl}-amide;

3-oxo-3,4-dihydro-2H-pyrido[3,2-b][1,4]thiazine-6-carboxylic acid {1-[2-(7-methoxy-quinolin-2-yloxy)-ethyl]-piperidin-4-yl}-amide;

3-oxo-3,4-dihydro-2H-benzo[1,4]thiazine-6-carboxylic acid {1-[2-(7-methoxy-[1,5]naphthyridin-2-yloxy)-ethyl]-piperidin-4-yl}-amide;

7-chloro-3-oxo-3,4-dihydro-2H-benzo[1,4]thiazine-6-carboxylic acid {1-[2-(7-methoxy-[1,5]naphthyridin-2-yloxy)-ethyl]-piperidin-4-yl}-amide;

3-oxo-3,4-dihydro-2H-pyrido[3,2-b][1,4]thiazine-6-carboxylic acid {1-[2-(7-methoxy-quinoxalin-2-yloxy)-ethyl]-piperidin-4-yl}-amide;

6-methoxy-quinoline-3-carboxylic acid trans-4-[(3-oxo-3,4-dihydro-2H-benzo[1,4]thiazine-6-carbonyl)-amino]-cyclohexylmethyl ester;

7-chloro-3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-amide;

7-chloro-3,4-dihydro-2H-benzo[1,4]thiazine-6-carboxylic acid {1-[2-(7-methoxy-quinoxalin-2-ylsulfanyl)-ethyl]-piperidin-4-yl}-amide;

6-({1-[2-(7-methoxy-quinoxalin-2-ylsulfanyl)-ethyl]-piperidin-4-ylamino}-methyl)-4H-benzo[1,4]thiazin-3-one;

7-chloro-6-({1-[2-(7-methoxy-quinoxalin-2-ylsulfanyl)-ethyl]-piperidin-4-ylamino}-methyl)-4H-benzo[1,4]thiazin-3-one;

(7-chloro-3,4-dihydro-2H-benzo[1,4]thiazin-6-ylmethyl)-[1-[2-(7-methoxy-quinoxalin-2-ylsulfanyl)-ethyl]-piperidin-4-yl]-amine;

3-oxo-3,4-dihydro-2H-pyrido[3,2-b][1,4]thiazine-6-carboxylic acid {1-[2-(7-methoxy-quinoxalin-2-ylsulfanyl)-ethyl]-piperidin-4-yl}-amide;

7-chloro-3-oxo-3,4-dihydro-2H-pyrido[3,2-b][1,4]thiazine-6-carboxylic acid {1-[2-(7-methoxy-quinoxalin-2-ylsulfanyl)-ethyl]-piperidin-4-yl}-amide;

3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-methyl-amide;

3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide;

7-chloro-3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide;

3-oxo-3,4-dihydro-2H-pyrido[3,2-b][1,4]thiazine-6-carboxylic acid {1-[2-(6-methoxy-quinolin-3-ylsulfanyl)-ethyl]-piperidin-4-yl}-amide and 7-chloro-3-oxo-3,4-dihydro-2H-pyrido[3,2-b][1,4]thiazine-6-carboxylic acid {1-[2-(6-methoxy-quinolin-3-ylsulfanyl)-ethyl]-piperidin-4-yl}-amide or a pharmaceutically acceptable salt, a hydrate or solvate thereof.

24. The compound of claim 1, wherein said compound is selected from the group consisting of 3-oxo-3,4-dihydro-2H-benzo[1,4]thiazine-6-carboxylic acid {trans-4-[2-(6-methoxy-[1,5]naphthyridin-3-yloxy)-ethyl]-cyclohexyl}-amide;

7-chloro-3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-amide;

6-({1-[2-(7-methoxy-quinoxalin-2-ylsulfanyl)-ethyl]-piperidin-4-ylamino}-methyl)-4H-benzo[1,4]thiazin-3-one;

7-chloro-6-({1-[2-(7-methoxy-quinoxalin-2-ylsulfanyl)-ethyl]-piperidin-4-ylamino}-methyl)-4H-benzo[1,4]thiazin-3-one;

(7-chloro-3,4-dihydro-2H-benzo[1,4]thiazin-6-ylmethyl)-{1-[2-(7-methoxy-quinoxalin-2-ylsulfanyl)-ethyl]-piperidin-4-yl}-amine;

3-oxo-3,4-dihydro-2H-pyrido[3,2-b][1,4]thiazine-6-carboxylic acid {1-[2-(7-methoxy-quinoxalin-2-ylsulfanyl)-ethyl]-piperidin-4-yl}-amide;

3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-methyl-amide;

3-oxo-3,4-dihydro-2H-benzo[1,4]thiazine-6-carboxylic acid {1-[2-(6-methoxy-quinolin-3-ylsulfanyl)-ethyl]piperidin-4-yl}-amide and 3-oxo-3,4-dihydro-2H-pyrido[3,2-b][1,4]thiazine-6-carboxylic acid {1-[2-(6-methoxy-quinolin-3-ylsulfanyl)-ethyl]-piperidin-4-yl}-amide or a pharmaceutically acceptable salt, a hydrate or solvate thereof.

25. The compound of claim 1, wherein said compound is selected from the group consisting of 7-chloro-3-oxo-3,4-dihydro-2H-benzo[1,4]thiazine-6-carboxylic acid {1-[2-(7-methoxy-quinoxalin-2-ylsulfanyl)-ethyl]-piperidin-4-yl}-amide;

7-chloro-3,4-dihydro-2H-benzo[1,4]thiazine-6-carboxylic acid {1-[2-(7-methoxy-quinoxalin-2-ylsulfanyl)-ethyl]-piperidin-4-yl}-amide;

6-({1-[2-(7-methoxy-quinoxalin-2-ylsulfanyl)-ethyl]-piperidin-4-ylamino}-methyl)-4H-benzo[1,4]thiazin-3-one;

7-chloro-6-({1-[2-(7-methoxy-quinoxalin-2-ylsulfanyl)-ethyl]-piperidin-4-ylamino}-methyl)-4H-benzo[1,4]thiazin-3-one;

(7-chloro-3,4-dihydro-2H-benzo[1,4]thiazin-6-ylmethyl)-[1-[2-(7-methoxy-quinoxalin-2-ylsulfanyl)-ethyl]-piperidin-4-yl]-amine;

3-oxo-3,4-dihydro-2H-pyrido[3,2-b][1,4]thiazine-6-carboxylic acid {1-[2-(7-methoxy-quinoxalin-2-ylsulfanyl)-ethyl]-piperidin-4-yl}-amide;

7-chloro-3-oxo-3,4-dihydro-2H-pyrido[3,2-b][1,4]thiazine-6-carboxylic acid {1-[2-(7-methoxy-quinoxalin-2-ylsulfanyl)-ethyl]-piperidin-4-yl}-amide;

3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide and 7-chloro-3-oxo-3,4-dihydro-2H-benzo[1,4]thiazine-6-carboxylic acid {1-[2-(6-methoxy-quinolin-3-ylsulfanyl)-ethyl]-piperidin-4-yl}-amide or a pharmaceutically acceptable salt, a hydrate or solvate thereof.

26. The compound of claim 1, wherein said compound is selected from the group consisting of 3-oxo-3,4-dihydro-2H-benzo[1,4]thiazine-6-carboxylic acid {1-[2-(7-ethoxy-quinoxalin-2-yloxy)-ethyl]-piperidin-4-yl}-amide;

3-oxo-3,4-dihydro-2H-benzo[1,4]thiazine-6-carboxylic acid {1-[2-(7-difluoromethoxy-quinoxalin-2-yloxy)-ethyl]-piperidin-4-yl}-amide;

3-oxo-3,4-dihydro-2H-benzo[1,4]thiazine-6-carboxylic acid {1-[3-methoxy-2-(7-methoxy-quinoxalin-2-yloxy)-propyl]-piperidin-4-yl}-amide;

(3S,4R)-3-oxo-3,4-dihydro-2H-benzo[1,4]thiazine-6-carboxylic acid {3-hydroxymethyl-1-[2-(7-methoxy-quinoxalin-2-yloxy)-ethyl]-piperidin-4-yl}-amide;

3-oxo-3,4-dihydro-2H-benzo[1,4]thiazine-6-carboxylic acid {1-[2-(2-methoxy-quinolin-7-yloxy)-ethyl]-piperidin-4-yl}-amide;

6-({1-[2-(7-fluoro-6-methoxy-quinolin-3-yloxy)-ethyl]-piperidin-4-ylamino}-methyl)-4H-benzo[1,4]thiazin-3-one;

3-oxo-3,4-dihydro-2H-benzo[1,4]thiazine-6-carboxylic acid {1-[2-(7,8-dimethoxy-quinoxalin-2-ylsulfanyl)-ethyl]-piperidin-4-yl}-amide;

(3R,4R)-3-oxo-3,4-dihydro-2H-benzo[1,4]thiazine-6-carboxylic acid {3-hydroxy-1-[2-(7-methoxy-quinoxalin-2-yloxy)-ethyl]-piperidin-4-yl}-amide;

(3S,4R)-3-oxo-3,4-dihydro-2H-benzo[1,4]thiazine-6-carboxylic acid {3-hydroxy-1-[2-(7-methoxy-quinoxalin-2-yloxy)-ethyl]-piperidin-4-yl}-amide;

(3R,4S)-3-oxo-3,4-dihydro-2H-benzo[1,4]thiazine-6-carboxylic acid {3-hydroxy-1-[2-(7-methoxy-quinoxalin-2-yloxy)-ethyl]-piperidin-4-yl}-amide;

(3S,4S)-3-oxo-3,4-dihydro-2H-benzo[1,4]thiazine-6-carboxylic acid {3-hydroxy-1-[2-(7-methoxy-quinoxalin-2-yloxy)-ethyl]-piperidin-4-yl}-amide;

3-oxo-3,4-dihydro-2H-benzo[1,4]thiazine-6-carboxylic acid {1-[2-(7-methoxy-quinoxalin-2-yloxy)-propyl]-piperidin-4-yl}-amide;

3-oxo-3,4-dihydro-2H-benzo[1,4]thiazine-6-carboxylic acid {1-[3-fluoro-2-(7-methoxy-quinoxalin-2-yloxy)-propyl]-piperidin-4-yl}-amide;

2-chloro-6-methoxy-quinoline-3-carboxylic acid trans-4-[(3-oxo-3,4-dihydro-2H-benzo[1,4]thiazine-6-carbonyl)-amino]-cyclohexylmethyl ester;

7-Chloro-6-({1-[2-(6-methoxy-[1,5]naphthyridin-3-ylsulfanyl)-ethyl]piperidin-4-ylamino}-methyl)-4H-pyrido[3,2-b][1,4]thiazin-3-one;

3-oxo-3,4-dihydro-2H-benzo[1,4]thiazine-6-carboxylic acid {1-[2-(7-methoxy-quinoxalin-2-ylsulfanyl)-ethyl]-piperidin-3-yl}-amide;

6-({3-hydroxymethyl-1-[2-(7-methoxy-quinoxalin-2-ylsulfanyl)-ethyl]-piperidin-4-ylamino}-methyl)-4H-benzo[1,4]thiazin-3-one; and 3,4-dihydro-2H-benzo[1,4]thiazine-6-carboxylic acid {1-[2-(7-methoxy-quinoxalin-2-ylsulfanyl)-ethyl]-piperidin-4-yl}-amide or a pharmaceutically acceptable salt, a hydrate or solvate thereof.

27. The compound of claim 1, wherein said compound is selected from the group consisting of (3S,4R)-3-oxo-3,4-dihydro-2H-benzo[1,4]thiazine-6-carboxylic acid {3-hydroxymethyl-1-[2-(7-methoxy-quinoxalin-2-yloxy)-ethyl]-piperidin-4-yl}-amide;

(3R,4R)-3-oxo-3,4-dihydro-2H-benzo[1,4]thiazine-6-carboxylic acid {3-hydroxy-1-[2-(7-methoxy-quinoxalin-2-yloxy)-ethyl]-piperidin-4-yl}-amide;

(3S,4S)-3-oxo-3,4-dihydro-2H-benzo[1,4]thiazine-6-carboxylic acid {3-hydroxy-1-[2-(7-methoxy-quinoxalin-2-yloxy)-ethyl]-piperidin-4-yl}-amide;

3-oxo-3,4-dihydro-2H-benzo[1,4]thiazine-6-carboxylic acid {1-[3-fluoro-2-(7-methoxy-quinoxalin-2-yloxy)-propyl]-piperidin-4-yl}-amide;

7-Chloro-6-({1-[2-(6-methoxy-[1,5]naphthyridin-3-ylsulfanyl)-ethyl]piperidin-4-ylamino}-methyl)-4H-pyrido[3,2-b][1,4]thiazin-3-one;

3-oxo-3,4-dihydro-2H-benzo[1,4]thiazine-6-carboxylic acid {1-[2-(7-methoxy-quinoxalin-2-ylsulfanyl)-ethyl]-piperidin-3-yl}-amide;

6-({3-hydroxymethyl-1-[2-(7-methoxy-quinoxalin-2-ylsulfanyl)-ethyl]-piperidin-4-ylamino}-methyl)-4H-benzo[1,4]thiazin-3-one and 3,4-dihydro-2H-benzo[1,4]thiazine-6-carboxylic acid {1-[2-(7-methoxy-quinoxalin-2-ylsulfanyl)-ethyl]-piperidin-4-yl}-amide or a pharmaceutically acceptable salt, a hydrate or solvate thereof.

28. The compound of claim 1, wherein said compound is 7-Chloro-6-({1-[2-(6-methoxy-[1,5]naphthyridin-3-ylsulfanyl)-ethyl]-piperidin-4-ylamino}-methyl)-4H-pyrido[3,2-b][1,4]thiazin-3-one or a pharmaceutically acceptable salt, a hydrate or solvate thereof.

29. The compound of claim 9, wherein X3 and X6 or X3 and X1 are nitrogen.

* * * * *